US010196697B2

(12) United States Patent
Walker et al.

(10) Patent No.: US 10,196,697 B2
(45) Date of Patent: Feb. 5, 2019

(54) PROSTATE CANCER CLASSIFICATION

(71) Applicant: Almac Diagnostics Limited, Craigavon (GB)

(72) Inventors: Steven Walker, Craigavon (GB); Andrena McCavigan, Lurgan (GB); Timothy Davison, Hillsborough (GB); Richard Kennedy, Belfast (GB); Paul Harkin, Dromore (GB); Laura Hill, Lisburn (GB)

(73) Assignee: ALMAC DIAGNOSTICS LIMITED (GB)

( * ) Notice: Subject to any disclaimer, the term of this patent is extended or adjusted under 35 U.S.C. 154(b) by 0 days.

(21) Appl. No.: 15/103,770

(22) PCT Filed: Dec. 12, 2014

(86) PCT No.: PCT/GB2014/053694
§ 371 (c)(1),
(2) Date: Jun. 10, 2016

(87) PCT Pub. No.: WO2015/087088
PCT Pub. Date: Jun. 18, 2015

(65) Prior Publication Data
US 2016/0312294 A1 Oct. 27, 2016

(30) Foreign Application Priority Data
Dec. 12, 2013 (GB) .................................. 1322034.8

(51) Int. Cl.
*C12Q 1/6886* (2018.01)
*A61K 31/337* (2006.01)
*C07K 16/18* (2006.01)
*C07K 16/40* (2006.01)

(52) U.S. Cl.
CPC .......... *C12Q 1/6886* (2013.01); *A61K 31/337* (2013.01); *C07K 16/18* (2013.01); *C07K 16/40* (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS 5,437,975 A 8/1995 Mcclelland et al.
6,410,276 B1 6/2002 Burg et al.
2003/0092900 A1 5/2003 Iruela-Arispe et al.
2003/0108963 A1 6/2003 Schlegel et al.
2003/0175736 A1 9/2003 Chinnaiyan et al.
2004/0029151 A1 2/2004 Mahadevappa et al.
2004/0223970 A1 11/2004 Afar et al.
2005/0032065 A1 2/2005 Afar et al.
2005/0186571 A1 8/2005 Ullrich et al.
2005/0259483 A1 11/2005 Nakamura et al.
2006/0246495 A1 11/2006 Garrett et al.
2007/0048738 A1 3/2007 Donkena et al.
2007/0059753 A1 3/2007 Vener et al.
2007/0065856 A1 3/2007 Belacel et al.
2008/0181894 A1 7/2008 Mink et al.
2008/0213791 A1 9/2008 Freije et al.
2009/0233279 A1 9/2009 Glinskii
2009/0298082 A1 12/2009 Klee et al.
2010/0055705 A1 3/2010 Wilson et al.
2010/0113290 A1 5/2010 Klass et al.
2010/0130377 A1 5/2010 Vasmatzis et al.
2010/0233691 A1 9/2010 Bankaitis-Davis et al.
2011/0045464 A1 2/2011 Reddy et al.
2011/0071032 A1 3/2011 Zeillinger et al.
2011/0076280 A1 3/2011 Nakamura
2011/0136683 A1 6/2011 Davicioni
2011/0159498 A1 6/2011 Kao et al.
2011/0236903 A1 9/2011 McClelland et al.

(Continued)

FOREIGN PATENT DOCUMENTS

CN 103146688 A 6/2013
JP 2008271979 A 11/2008

(Continued)

OTHER PUBLICATIONS

Jiang L, et al in "PDRG1, a novel tumor marker for multiple malignancies that is selectively regulated by genotoxic stress." Cancer Biol Ther, Mar. 15, 2011.*
Cross et al., "Purification of CpG islands using a methylated DNA binding column", Article, Nature Genetics, vol. 6, Mar. 1994, 9 pages, Nature Publishing Group.
Furuichi et al., "Chemical modification of tRNA-Tyr-yeast with bisulfite. A new method to modify isopentenyladenosine residue", Biochemical and Biophysical Research Communications, vol. 41, No. 5, Oct. 19, 1970, 7 pages.

(Continued)

*Primary Examiner* — Catherine S Hibbert
(74) *Attorney, Agent, or Firm* — Finnegan, Henderson, Farabow, Garrett & Dunner LLP

(57) ABSTRACT

A method is provided for characterizing and/or prognosing prostate cancer in a subject comprising determining the expression level of at least one of CREM, ERRFI1, SRSF5, PDK4, HJURP, PDRG1, TRPM3, PDE4D, FI2, ADAMTS1, ADAMTS9, B3GNT5, CD38, CEBPD, CENPF, DKK1, EMP1, F3, IL1R1, IL8, JUNB, KLFIO, KLF4, LDLR, LGALS3, LPARI, MALAT1, MTUS1, MYBPC1, NFIL3, NR4A3, OAT, PI15, PTGS2, RHOBTB3, RIN2, RNFT2, SELE, SLC15A2, SOCS2, SOCS3, SSTR1, ST6GAL1, TSC22D1, XBP1 and ZFP36 in a sample from the subject. The method may be used to predict the likelihood of metastasis. Also disclosed are methods for diagnosing and selecting treatment for prostate cancer, together with corresponding methods of treatment. Systems, kits and computer programs for performing the methods are also provided.

10 Claims, 8 Drawing Sheets

Specification includes a Sequence Listing.

(56) References Cited

U.S. PATENT DOCUMENTS

2011/0265197 A1 10/2011 Depinho et al.
2012/0009581 A1 1/2012 Bankaitis-Davis et al.
2012/0028264 A1 2/2012 Shak et al.
2012/0041274 A1 2/2012 Stone et al.
2012/0053253 A1 3/2012 Stone et al.
2012/0065148 A1 3/2012 Hoffmann et al.
2012/0214684 A1 8/2012 Vieweg et al.
2012/0245235 A1 9/2012 Rhodes et al.
2013/0064840 A1 3/2013 Nakamura et al.
2013/0079241 A1* 3/2013 Luo ..................... C12Q 1/6874 506/9
2013/0196321 A1 8/2013 Shak et al.
2013/0288967 A1 10/2013 Freije et al.
2013/0302242 A1 11/2013 Stone et al.

FOREIGN PATENT DOCUMENTS

JP 2012529021 A 11/2012
WO WO 1990/006995 6/1990
WO WO 1997/046705 12/1997
WO WO-0231209 A2 4/2002
WO WO 02/44418 A2 6/2002
WO WO 2004/067726 8/2004
WO WO 2006/091776 A2 8/2006
WO WO-08067065 A2 6/2008
WO WO-09151503 A2 12/2009
WO WO-10131194 A1 11/2010
WO WO 2010/139711 A1 12/2010
WO WO 2011/094233 A1 8/2011
WO WO 2011/106709 A2 9/2011
WO WO 2011/153287 A2 12/2011
WO WO 2012/018609 A2 2/2012
WO WO-12149245 A2 11/2012
WO WO 2013/003384 A1 1/2013
WO WO-13041731 A1 3/2013
WO WO-13096837 A1 6/2013
WO WO 2013/142939 A1 10/2013
WO WO-13149039 A1 10/2013

OTHER PUBLICATIONS

Jones et al., "Replacing the complementarity-determining regions in a human antibody with those from a mouse", Laboratory of Molecular Biology, Medical Research Council, Cambridge, UK, 4 pages, Nature Publishing Group.

Kattan et al., "Postoperative Nomogram for Disease Recrrence After Radical Prostatectomy for Prostate Cancer", Journal of Clinical Oncology, vol. 17, No. 5, May 1, 1999, 10 pages, American Society of Clinical Oncology.

Laird, "The Power and the Promise of DNA Methylation Markers", Reviews, vol. 3, Apr. 2003, University of Southern California, Norris Comprehensive Cancer Center, DOI: 10.1038/nrc 1045, 14 pages, Nature Publishing Group.

Affymetrix: "GeneChip TM Human Genome Arrays," Retrieved from the internet, URL:http://www.osa.sunysb.edu/udmf/ArraySheets/human_datasheet.pdf, Retrieved Oct. 13, 2016.

Anonymous: "Information for probe set 207630_s_at (HG-U133_Plus_2)" Jan. 2, 2014, Retrieved from the Internet, URL: http://genecards.weizmann.ac.il/cgi-bin/geneannot/GA_search.pl?array=HG-U133_Plus_2&keyword_type=probe_set_list&keyword=207630_s_at&target=integrated&submit=Submit+Query , Retrieved Oct. 13, 2016.

Gautrey, H. et al., "Regulation of Mcl-1 by SRSF1 and SRSF5 in cancer cells," PLoS One, 2012; 7(12);e51497.

Hu, Z. et al., "The expression level of HJURP has an independent prognostic impact and predicts the sensitivity to radiotherapy in breast cancer," Breast Cancer Res. 2010;12(2):R18.

International Search Report for Internationai Application No. PCT/GB2014/053694, dated Aug. 6, 2015 (12 pages).

Jackson, W. et al., "Gleason pattern 5 is the strongest pathologic predictor of recurrence, metastasis, and prostate cancer-specific death in patients receiving salvage radiation therapy following radical prostatectomy," Cancer Sep. 15, 2013;119(18):3287-94.

Jiang, L. et al., "PDRG1, a novel tumor marker for multiple malignancies that is selectively regulated by genotoxic stress," Cancer Biol Ther. Mar. 15, 2011;11(6):567-73.

Kamarajugadda, S. et al., "Glucose oxidation modulates anoikis and tumor metastasis,"0 Mol Cell Biol. May 2012; 32(10):1893-907.

LaTulippe, E. et al., "Comprehensive gene expression analysis of prostate cancer reveals distinct transcriptional programs associated with metastatic, disease," Cancer Res. Aug. 1, 2002; 62(15):4499-506.

Memin, E. et al., "ICER reverses tumorigenesis of rat prostate tumor cells without affecting cell growth," Prostate Nov. 1, 2002;53(3):225-31.

Mengual, L. et al., "Gene expression profiles in prostate cancer: identification of candidate non-invasive diagnostic markers," Actas Urol Esp. Apr. 2014; 38(3):143-9.

Saigusa, S. et al., "Gene expression profiles of tumor regression grade in locally advanced rectal cancer after neoadjuvant chemoradiotherapy," Oncol Rep. Sep. 2012;28(3):855-61.

Tannock, I. et al., "Docetaxel plus prednisone or mitoxantrone plus prednisone for advanced prostate cancer," N Engl J Med. Oct. 7, 2004; 351(15):1502-12.

Wang, Y. et al, "Low expression of cyclic AMP response element modulator-1 can increase the migration and invasion of esophageal squamous cell carcinoma," Tumor Biol, Dec. 2013; 34(6):3649-57.

Written Opinion of the International Searching Authority for International Application No. PCT/GB2014/053694, dated Jul. 28, 2015 (26 pages).

Yehia, G., et al., "The expression of inducibie cAMP early repressor (ICER) is altered in prostate cancer cells and reverses the transformed phenotype of the LNCaP prostate tumor cell line," Cancer Res, Aug. 15, 2001;61(16):6055-9.

Jones PT et al., "Replacing the complementarity-determining regions in a human antibody with those from a mouse," Nature May 29-Jun. 4, 1986; 321 (6069):522-5.

Roguska MA et al., "A comparison of two murine monoclonal antibodies humanized by CDR-grafting and variable domain resurfacing," Protein Engineering, 1996, 9(10):895-904.

Studnicka GM et al., "Human-engineered monoclonal antibodies retain full specific binding activity by preserving non-CDR complementarity-modulating residues." Protein Engineering, 1994, vol. 7, p. 805-814.

Zeschinigk et al., "A novel real-time PCR assay for quantitative analysis of methylated alleles (QAMA): analysis of the retinoblastoma locus," Nucleic Acids Research, 2004, p. e125, vol. 32 (5 pages).

Melnikov AA, et al. (2005)"MSRE-PCR for analysis of gene-specific DNA methylation," Nucleic Acids Res 2005, 33:e93.

Eads CA et al., "MethyLight: a high-throughput assay to measure DNA methylation," Nucleic Acids Res. Apr. 15, 2000;28(8):E32.

Rand K et al., "Conversion-specific detection of DNA methylation using real-time polymerase chain reaction (ConLight-MSP) to avoid false positives," Methods. Jun. 2002;27(2):114-20.

Sasaki M et al., "Bisulfite conversion-specific and methylation-specific PCR: a sensitive technique for accurate evaluation of CpG methylation," Biochem Biophys Res Commun. Sep. 19, 2003;309(2):305-9.

Akey DT, et al., "Assaying DNA methylation based on high-throughput melting curve approaches," Genomics. Oct. 2002;80(4):376-84.

Cottrell SE, et al., "A real-time PCR assay for DNA-methylation using methylation-specific blockers," Nucleic Acids Res. Jan. 13, 2004;32(1):e10.

Rein T, et al., "Identifying 5-methylcytosine and related modifications in DNA genomes," Nucleic Acids Res. May 15, 1998;26(10):2255-64.

Laird PW, "The power and the promise of DNA methylation markers," Nat Rev Cancer.2003;3(4):253-66.

Auerkan EI, "Methylation of tumor suppressor genes p16(INK4a), p27(Kip1) and E-cadherin in carcinogenesis," Oral Oncol. Jan. 2006;42(1):5-13. Epub Jun. 22, 2005.

Cross SH et al., "Purification of CpG islands using a methylated DNA binding column," Nat Genet. Mar. 1994;6(3):236-44.

(56) References Cited

OTHER PUBLICATIONS

Shiraishi M st al., "Tight interaction between densely methylated DNA fragments and the methyl-CpG binding domain of the rat MeCP2 protein attached to a solid support," Biol Chem. Sep. 1999;380(9):1127-31.
Jorgensen HF, et al., "Engineering a high-affinity methyl-CpG-binding protein," Nucleic Acids Res. Aug. 7, 2006;34(13):e96.
Furuichi Y, "Chemical modification of tRNA-Tyr-yeast with bisulfite. A new method to modify isopentenyladenosine residue," Biochem Biophys Res Commun. Dec. 9, 1970;41(5):1185-91.
Tibshirani R, et al., "Estimating the number of clusters in a data set via the GAP statistic," J. R. Statist. Soc. B. 2001; 63(2):411-423.
Kennedy RD et al., "Development and independent validation of a prognostic assay for stage II colon cancer using formalin-fixed paraffin-embedded tissue," J Clin Oncol. Dec. 10, 2011;29(35):4620-6.
Albertsen PC, et al., "Prostate cancer and the Will Rogers phenomenon," J Natl Cancer Inst, Sep. 7, 2005;97(17):1248-53.
Alterkruse SF, et al., "Spatial patterns of localized-stage prostate cancer incidence among white and black men in the southeastern United States, 1999-2001," Cancer Epidemiol Biomarkers Prev. Jun. 2010;19(6):1460-7. doi: 10.1158/1055-9965.EPI-09-1310. Epub May 25, 2010.
Babbio F, et al., "The SRA protein UHRF1 promotes epigenetic crosstalks and is involved in prostate cancer progression," Oncogene. Nov. 15, 2012;31(46):4878-87. doi: 10.1038/onc.2011.641. Epub Feb. 13, 2012.
Bertucci F, et al., "Gene expression profiling of colon cancer by DNA microarrays and correlation with histoclinical parameters," Oncogene, Feb. 19, 2004;23(7):1377-91.
Bostick M, et al., "UHRF1 plays a role in maintaining DNA methylation in mammalian cells," Science. Sep. 21, 2007;317(5845):1760-4. Epub Aug. 2, 2007.
Chen X, et al., "The forkhead transcription factor FOXM1 controls cell cycle-dependent gene expression through an atypical chromatin binding mechanism," Mol Cell Biol. Jan. 2013;33(2):227-36. doi: 10.1128/MCB.00881-12. Epub Oct. 29, 2012.
Howlader N et al., "SEER Cancer Statistics Review," 1975-2009, National Cancer Institute. Bethesda, MD, http://seer.cancer.gov/csr/1975_2009/_ pops09/.
Kattan MW, et al., "Postoperative nomogram for disease recurrence after radical prostatectomy for prostate cancer," J Clin Oncol. May 1999;17(5):1499-507.
Makarov DV, et al., "Gleason score 7 prostate cancer on needle biopsy: is the prognostic difference in Gleason scores 4+3 and 3+4 independent of the number of involved cores?" J Urol. Jun. 2002; 167(6):2440-2.
Perou CM, et al., "Molecular portraits of human breast tumours," Nature. Aug. 17, 2000;406(6797):747-52.
Pound CR, et al., "Natural history of progression after PSA elevation following radical prostatectomy," JAMA May 5, 1999;281(17):1591-7.
Rasiah KK, et al., "Prognostic significance of Gleason pattern in patients with Gleason score 7 prostate carcinoma," Cancer. Dec. 15, 2003;98(12):2560-5.
Sanders DA, et al., "Genome-wide mapping of FOXM1 binding reveals co-binding with estrogen receptor alpha in breast cancer cells," Genome Biol. Jan. 24, 2013;14(1):R6. doi 10.1186/gb-2013-14-1-r6.
Sharif J, et al., "The SRA protein Np95 mediates epigenetic inheritance by recruiting Dnmt1 to methylated DNA," Nature. Dec. 6, 2007;450(7171):908-12. Epub Nov. 11, 2007.
Smith EB, et al., "Gleason scores of prostate biopsy and radical prostatectomy specimens over the past 10 years: is there evidence for systematic upgrading?"Cancer. Apr. 15, 2002;94(8):2262-7.
Sun Y, et al., "Optimizing molecular signatures for predicting prostate cancer recurrence," Prostate. Jul. 1, 2009;69(10):1119-27. doi: 10.1002/pros.20961.
Tusher VG, et al., "Significance analysis of microarrays applied to the ionizing radiation response," Proc Natl Acad Sci U S A. Apr. 24, 2001;98(9):5116-21, Epub Apr. 17, 2001.
Taylor BS, et al., "Integrative genomic profiling of human prostate cancer," Cancer Cell, Jul. 13, 2010;18(1):11-22. doi: 10.1016/j.ccr.2010.05.026. Epub Jun. 24, 2010.
Unoki M, et al., "UHRF1 is a novel molecular marker for diagnosis and the prognosis of bladder cancer," Br J Cancer. Jul. 7, 2009;101(1):98-105. doi: 10.1038/sj.bjc.6605123. Epub Jun. 2, 2009.
Van't Veer LJ, et al., "Gene expression profiling predicts clinical outcome of breast cancer," Nature. Jan. 31, 2002;415(6871):530-6.
Xu K. et al., "EZH2 oncogenic activity in castration-resistant prostate cancer cells is Polycomb-Independent," Science. Dec. 14, 2012;336(6113):1465-9. doi: 10.1126/science.1227604.
European Office Action dated Jul. 12, 2017, issued in corresponding European Patent Application No. 14 814 697.0 (8 pages).
Kamarajugadda et al., "Glucose Oxidation Modulates Anoikis and Tumor Metastasis," Molecular and Cellular Biology, May 15, 2012, vol. 32 No. 10, pp. 1893-1907.
Tannock et al., "Docetaxel plus Prednisone or Mitoxantrone plus Prednisone for Advanced Prostate Cancer," The New England Journal of Medicine, Oct. 7, 2004, vol. 351 No. 15, pp. 1502-1512.
Kamarajugadda et al., "Glucose Oxidation Modulates Anoikis and Tumor Metastasis," Molecular and Cellular Biology, May 2012, vol. 32, No. 10, pp. 1393-1907, 15 pages.
Official Communication, Office Action from the Japanese Patent Office dated Oct. 2, 2018, issued in corresponding Japanese Application No. 2016-538689 12 pages.

* cited by examiner

PROSTATE CANCER CLASSIFICATION

CROSS REFERENCE TO RELATED APPLICATIONS

This application is the national stage entry under 35 U.S.C. § 371 of International Application No. PCT/GB2014/053694, filed Dec. 12, 2014, which claims priority to Great Britain Application No. 1322034.8, filed Dec. 12, 2013. The contents of these applications are each incorporated herein by reference in their entirety.

SEQUENCE LISTING

The instant application contains a Sequence Listing which has been submitted electronically in ASCII format and is hereby incorporated by reference in its entirety. Said ASCII copy, created on Jun. 6, 2016, is named SequenceListing.txt and is 42,823 bytes in size.

FIELD OF THE INVENTION

The present invention relates to prostate cancer. Provided are methods for characterising and prognosing prostate cancer which rely upon biomarkers. Antibodies, kits and systems useful in the methods are also described.

BACKGROUND OF THE INVENTION

Prostate cancer is the most common malignancy in men with a lifetime incidence of 15.3% (Howlader 2012). Based upon data from 1999-2006 approximately 80% of prostate cancer patients present with early disease clinically confined to the prostate (Altekruse et al 2010) of which around 65% are cured by surgical resection or radiotherapy (Kattan et al 1999, Pound et al 1999). 35% will develop PSA recurrence of which approximately 35% will develop local or metastatic recurrence, which is non-curable. At present it is unclear which patients with early prostate cancer are likely to develop recurrence and may benefit from more intensive therapies. Current prognostic factors such as tumour grade as measured by Gleason score have prognostic value but a significant number of those considered lower grade (7 or less) still recur and a proportion of higher-grade tumours do not. Additionally there is significant heterogeneity in the prognosis of Gleason 7 tumours (Makarov et al 2002, Rasiah et al 2003). Furthermore it has become evident that the grading of Gleason score has changed leading to changes in the distribution of Gleason scores over time (Albertsen et al 2005, Smith et al 2002).

It is now clear that most solid tumours originating from the same anatomical site represent a number of distinct entities at a molecular level (Perou et al 2000). DNA microarray platforms allow the analysis of tens of thousands of transcripts simultaneously from archived paraffin embedded tissues and are ideally suited for the identification of molecular subgroups. This kind of approach has identified primary cancers with metastatic potential in solid tumours such as breast (van't Veer et al 2002) and colon cancer (Bertucci et al 2004).

DESCRIPTION OF THE INVENTION

The present invention is based upon the identification and verification of prostate cancer biomarkers.

The present inventors have identified a group of primary prostate cancers that are similar to metastatic disease at a molecular level. These tumours are defined by loss of expression of several genes and defined pathways; furthermore this group is defined by activation of the proto-oncogene FOXM1 that leads to increased expression of genes involved in mitosis. A series of biomarkers that can identify tumours within this subgroup have been defined which have multivariate prognostic power and can be used to prospectively assess if a tumour is at increased likelihood of recurrence and/or metastatic development.

Thus, in a first aspect the invention provides a method for characterising and/or prognosing prostate cancer in a subject comprising:

determining the expression level of at least one of FOXM1, TRPM3, PDRG1, SRSF5, PDE4D, F12, PDK4, ADAMTS1, ADAMTS9, B3GNT5, CD38, CEBPD, CENPF, CREM, DKK1, EMP1, ERRFI1, F3, HJURP, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, RNFT2, SELE, SLC15A2, SOCS2, SOCS3, SSTR1, ST6GAL1, TSC22D1, XBP1 and ZFP36 in a sample from the subject wherein the determined expression level is used to provide a characterisation of and/or a prognosis for the prostate cancer.

According to all aspects of the invention the prostate cancer may be a primary prostate cancer.

According to a further aspect of the invention there is provided a method for diagnosing a prostate cancer with an increased metastatic potential in a subject comprising:

determining the expression level of at least one of FOXM1, TRPM3, PDRG1, SRSF5, PDE4D, F12, PDK4, ADAMTS1, ADAMTS9, B3GNT5, CD38, CEBPD, CENPF, CREM, DKK1, EMP1, ERRFI1, F3, HJURP, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, RNFT2, SELE, SLC15A2, SOCS2, SOCS3, SSTR1, ST6GAL1, TSC22D1, XBP1 and ZFP36 in a sample from the subject wherein the determined expression level is used to identify whether a subject has a prostate cancer with increased metastatic potential.

In yet a further aspect, the present invention relates to a method for diagnosing a prostate cancer with an increased metastatic potential in a subject comprising:

determining the expression level of at least one of TRPM3, PDRG1, SRSF5, PDE4D, F12 and PDK4 in a sample from the subject wherein the determined expression level is used to identify whether a subject has a prostate cancer with increased metastatic potential.

The invention also relates to a method for characterising and/or prognosing prostate cancer in a subject comprising:

determining the expression level of at least one of FOXM1, TRPM3, PDRG1, SRSF5, PDE4D, F12, PDK4, ADAMTS1, ADAMTS9, B3GNT5, CD38, CEBPD, CENPF, CREM, DKK1, EMP1, ERRFI1, F3, HJURP, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, RNFT2, SELE, SLC15A2, SOCS2, SOCS3, SSTR1, ST6GAL1, TSC22D1, XBP1 and ZFP36 in a sample from the subject in order to identify the presence or absence of cells characteristic of an increased likelihood of recurrence and/or metastasis wherein the determined presence or absence of the cells is used to provide a characterisation of and/or a prognosis for the prostate cancer.

In a further aspect, the present invention relates to a method for characterising and/or prognosing prostate cancer in a subject comprising:

a) obtaining a sample from the subject b) applying an antibody specific for the protein product of at least one of FOXM1, TRPM3, PDRG1, SRSF5, PDE4D, F12, PDK4, ADAMTS1, ADAMTS9, B3GNT5, CD38, CEBPD, CENPF, CREM, DKK1, EMP1, ERRFI1, F3, HJURP, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, RNFT2, SELE, SLC15A2, SOCS2, SOCS3, SSTR1, ST6GAL1, TSC22D1, XBP1 and ZFP36 to the sample from the subject c) applying a detection agent that detects the antibody-protein complex d) using the detection agent to determine the level of the protein d) wherein the determined level of the protein is used to provide a characterisation of and/or a prognosis for the prostate cancer.

The characterization, prognosis or diagnosis of the prostate cancer can also be used to guide treatment.

Accordingly, in a further aspect, the present invention relates to a method for selecting a treatment for prostate cancer in a subject comprising:

(a) determining the expression level of at least one of

FOXM1, TRPM3, PDRG1, SRSF5, PDE4D, F12, PDK4, ADAMTS1, ADAMTS9, B3GNT5, CD38, CEBPD, CENPF, CREM, DKK1, EMP1, ERRFI1, F3, HJURP, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, RNFT2, SELF, SLC15A2, SOCS2, SOCS3, SSTR1, ST6GAL1, TSC22D1, XBP1 and ZFP36 in a sample from the subject wherein the determined expression level is used to provide a characterisation of and/or a prognosis for the prostate cancer and (b) selecting a treatment appropriate to the characterisation of and/or prognosis for the prostate cancer.

In yet a further aspect, the present invention relates to a method for selecting a treatment for prostate cancer in a subject comprising:

(a) determining the expression level of at least one of

FOXM1, TRPM3, PDRG1, SRSF5, PDE4D, F12, PDK4, ADAMTS1, ADAMTS9, B3GNT5, CD38, CEBPD, CENPF, CREM, DKK1, EMP1, ERRFI1, F3, HJURP, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, RNFT2, SELE, SLC15A2, SOCS2, SOCS3, SSTR1, ST6GAL1, TSC22D1, XBP1 and ZFP36 in a sample from the subject wherein the determined expression level is used to provide a characterisation of and/or a prognosis for the prostate cancer (b) selecting a treatment appropriate to the characterisation of and/or prognosis for the prostate cancer and (c) treating the subject with the selected treatment.

The invention also relates to a method of treating prostate cancer comprising administering a chemotherapeutic agent or radiotherapy, optionally extended radiotherapy, preferably extended-field radiotherapy, to a subject or carrying out surgery on a subject wherein the subject is selected for treatment on the basis of a method as described herein.

In a further aspect, the present invention relates to a chemotherapeutic agent for use in treating prostate cancer in a subject, wherein the subject is selected for treatment on the basis of a method as described herein.

In yet a further aspect, the present invention relates to method of treating prostate cancer comprising administering a chemotherapeutic agent or radiotherapy, optionally extended radiotherapy, preferably extended-field radiotherapy to a subject or carrying out surgery on a subject wherein the subject has an increased expression level of at least one of HJURP, PDRG1, TRPM3, F12, CENPF, RNFT2, and SSTR1 and/or a decreased expression level of at least one of CREM, ERRFI1, SRSF5, PDK4, PDE4D, ADAMTS1, ADAMTS9, B3GNT5, CD38, CEBPD, DKK1, EMP1, F3, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, SELF, SLC15A2, SOCS2, SOCS3, ST6GAL1, TSC22D1, XBP1 and ZFP36.

The invention also relates to a chemotherapeutic agent for use in treating prostate cancer in a subject, wherein the subject has an increased expression level of at least one of HJURP, PDRG1, TRPM3, F12, CENPF, RNFT2, and SSTR1 and/or a decreased expression level of at least one of CREM, ERRFI1, SRSF5, PDK4, PDE4D, ADAMTS1, ADAMTS9, B3GNT5, CD38, CEBPD, DKK1, EMP1, F3, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, SELE, SLC15A2, SOCS2, SOCS3, ST6GAL1, TSC22D1, XBP1 and ZFP36.

In certain embodiments the chemotherapeutic agent comprises, consists essentially of or consists of a) an anti-hormone treatment, preferably bicalutamide and/or abiraterone b) a cytotoxic agent c) a biologic, preferably an antibody and/or a vaccine, more preferably Sipuleucel-T and/or d) a targeted therapeutic agent Suitable therapies and therapeutic agents are discussed in further detail herein.

The genes FOXM1, TRPM3, PDRG1, SRSF5, PDE4D, F12, PDK4, ADAMTS1, ADAMTS9, B3GNT5, CD38, CEBPD, CENPF, CREM, DKK1, EMP1, ERRFI1, F3, HJURP, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, RNFT2, SELE, SLC15A2, SOCS2, SOCS3, SSTR1, ST6GAL1, TSC22D1, XBP1 and ZFP36 and their protein products are described and defined in further detail in Table A below. The genes may also be referred to, interchangeably, as biomarkers.

TABLE A

| Gene | Previous names and symbols and Synonyms (HGNC database) | Uniprot number | Protein |
|---|---|---|---|
| FOXM1 | FKHL16, HFH-11, HNF-3, INS-1, “M-phase phosphoprotein 2”, MPHOSPH2, MPP2, TGT3, trident | Q08050 | forkhead box M1 |

TABLE A-continued

| Gene | Previous names and symbols and Synonyms (HGNC database) | Uniprot number | Protein |
|---|---|---|---|
| TRPM3 | GON-2, KIAA1616, LTRPC3, "melastatin 2" | Q9HCF6 | Transient receptor potential cation channel subfamily M member 3 |
| PDRG1 | C20orf126, "chromosome 20 open reading frame 126", dJ310O13.3 | Q9NUG6 | p53 and DNA damage-regulated protein 1 |
| SRSF5 | SFRS5, "splicing factor, arginine/serine-rich 5", HRS, "SR splicing factor 5", SRP40 | Q13243 | Serine/arginine-rich splicing factor 5 |
| PDE4D | DPDE3, "phosphodiesterase 4D, cAMP-specific (dunce (*Drosophila*)-homolog phosphodiesterase E3)" | Q08499 | cAMP-specific 3',5'-cyclic phosphodiesterase 4D |
| F12 | N/A | P00748 | Coagulation factor XII |
| PDK4 | "pyruvate dehydrogenase kinase, isoenzyme 4" | Q16654 | [Pyruvate dehydrogenase [lipoamide]] kinase isozyme 4, mitochondrial |
| ADAMTS1 | "a disintegrin-like and metalloprotease (reprolysin type) with thrombospondin type 1 motif, 1", C3-C5, KIAA1346, METH1 | Q9UHI8 | A disintegrin and metalloproteinase with thrombospondin motifs 1 |
| ADAMTS9 | KIAA1312 | Q9P2N4 | A disintegrin and metalloproteinase with thrombospondin motifs 9 |
| B3GNT5 | B3GN-T5, beta3Gn-T5, "lactosylceramide 1,3-N-acetyl-beta-D-glucosaminyltransferase | "Q9BYG0 | Lactosylceramide 1,3-N-acetyl-beta-D-glucosaminyltransferase |
| CD38 | "CD38 antigen (p45)", "ADP-ribosyl cyclase 1", "NAD(+) nucleosidase" | P28907 | ADP-ribosyl cyclase 1 |
| CEBPD | C/EBP-delta, CELF, CRP3, NF-IL6-beta | P49716 | CCAAT/enhancer-binding protein delta |
| CENPF | "centromere protein F, 350/400 kDa (mitosin)", hcp-1, "mitosin" | P49454 | Centromere protein F |
| CREM | hCREM-2 | Q03060 | CAMP-responsive element modulator |
| DKK1 | "dickkopf (*Xenopus laevis*) homolog 1", "dickkopf 1 homolog (*Xenopus laevis*)", DKK-1, SK | O94907 | Dickkopf-related protein 1 |
| EMP1 | CL-20, TMP | P54849 | Epithelial membrane protein 1 |
| ERRFI1 | GENE-33, MIG-6, RALT | Q9UJM3 | ERBB receptor feedback inhibitor 1 |
| F3 | CD142 | P13726 | Tissue factor |
| HJURP | DKFZp762E1312, FAKTS, hFLEG1, URLC9 | Q8NCD3 | Holliday junction recognition protein |
| ILIR1 | IL1R, IL1RA, CD121A, D2S1473 | P14778 | Interleukin-1 receptor type 1 |
| IL8 | 3-10C, "alveolar macrophage chemotactic factor I", AMCF-I, b-ENAP, "beta endothelial cell-derived neutrophil activating peptide", "chemokine (C—X—C motif) ligand 8", CXCL8, GCP-1, GCP1, "granulocyte chemotactic protein 1", IL-8, K60, LECT, LUCT, "lung giant cell carcinoma-derived chemotactic protein", "lymphocyte derived neutrophil activating peptide", LYNAP, MDNCF, MONAP, "monocyte-derived neutrophil chemotactic factor", "monocyte-derived neutrophil-activating peptide", NAF, NAP-1, NAP1, "neutrophil-activating peptide 1", SCYB8, TSG-1, "tumor necrosis factor-induced gene 1" | P10145 | Interleukin-8 |
| JUNB | N/A | P17275 | Transcription factor jun-B |
| KLF10 | "TGFB inducible early growth response", TIEG, EGRA, TIEG1 | Q13118 | Krueppel-like factor 10 |
| KLF4 | EZF, GKLF | O43474 | Krueppel-like factor 4 |
| LDLR | "familial hypercholesterolemia", LDLCQ2 | P01130 | Low-density lipoprotein receptor |
| LGALS3 | LGALS2, "galectin 3", GALIG, MAC-2 | P17931 | Galectin-3 |

TABLE A-continued

| Gene | Previous names and symbols and Synonyms (HGNC database) | Uniprot number | Protein |
|---|---|---|---|
| LPAR1 | EDG2, "endothelial differentiation, lysophosphatidic acid G-protein-coupled receptor, 2", edg-2, Gper26, GPR26, LPA1, Mrec1.3, rec.1.3, vzg-1 | Q92633 | Lysophosphatidic acid receptor 1 |
| MALAT1 | HCN, "hepcarcin", LINC00047, "long intergenic non-protein coding RNA 47", MALAT-1, "metastasis associated in lung adenocarcinoma transcript 1", NCRNA00047, NEAT2, "non-protein coding RNA 47", "nuclear enriched abundant transcript 2", "nuclear paraspeckle assembly transcript 2 (non-protein coding)", PRO1073 | Q9UHZ2 | Metastasis-associated lung adenocarcinoma transcript 1 |
| MTUS1 | "mitochondrial tumor suppressor 1", "AT2 receptor-interacting protein", "AT2R binding protein", ATBP, ATIP1, DKFZp586D1519, FLJ14295, ICIS, KIAA1288, "mitochondrial tumor suppressor gene 1", MP44, MTSG1 | Q9ULD2 | Microtubule-associated tumor suppressor 1 |
| MYBPC1 | "myosin-binding protein C, slow-type" | Q00872 | Myosin-binding protein C, slow-type |
| NFIL3 | IL3BP1, E4BP4, NF-IL3A, NFIL3A | Q16649 | Nuclear factor interleukin-3-regulated protein |
| NR4A3 | CHN, CSMF, MINOR, NOR1 | Q92570 | Nuclear receptor subfamily 4 group A member 3 |
| OAT | "gyrate atrophy", HOGA, "Ornithine aminotransferase", "ornithine aminotransferase precursor" | P04181 | Ornithine aminotransferase, mitochondrial |
| PI15 | "protease inhibitor 15", P25TI | O43692 | Peptidase inhibitor 15 |
| PTGS2 | COX2 | P35354 | Prostaglandin G/H synthase 2 |
| RHOBTB3 | KIAA0878 | O94955 | Rho-related BTB domain-containing protein 3 |
| RIN2 | RASSF4 | Q8WYP3 | Ras and Rab interactor 2 |
| RNFT2 | TMEM118, "transmembrane protein 118", FLJ14627 | Q96EX2 | RING finger and transmembrane domain-containing protein 2 |
| SELE | ELAM, ELAM1, "endothelial adhesion molecule 1", CD62E, ESEL | P16581 | E-selectin |
| SLC15A2 | "solute carrier family 15 (H+/peptide transporter), member 2", PEPT2 | Q16348 | Solute carrier family 15 member 2 |
| SOCS2 | CIS2, Cish2, SOCS-2, SSI-2, SSI2, "STAT-induced STAT inhibitor-2", STATI2 | O14508 | Suppressor of cytokine signaling 2 |
| SOCS3 | CIS3, Cish3, SOCS-3, SSI-3 | O14543 | Suppressor of cytokine signaling 3 |
| SSTR1 | N/A | P30872 | Somatostatin receptor type 1 |
| ST6GAL1 | "sialyltransferase 1 (beta-galactoside alpha-2,6-sialytransferase)", SIAT1, "ST6Gal I" | P15907 | Beta-galactoside alpha-2,6-sialyltransferase 1 |
| TSC22D1 | TGFB1I4, "transforming growth factor beta 1 induced transcript 4", MGC17597, TSC22 | Q15714 | TSC22 domain family protein 1 |
| XBP1 | XBP2 | P17861 | X-box-binding protein 1 |
| ZFP36 | "zinc finger protein 36, C3H type, homolog (mouse)", G0S24, NUP475, RNF162A, TIS11, tristetraprolin, TTP | P26651 | Tristetraprolin |

In certain embodiments the expression level of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45 or 46 of TRPM3, PDRG1, SRSF5, PDE4D, F12, PDK4, ADAMTS1, ADAMTS9, B3GNT5, CD38, CEBPD, CENPF, CREM, DKK1, EMP1, ERRFI1, F3, HJURP, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, RNFT2, SELE, SLC15A2, SOCS2, SOCS3, SSTR1, ST6GAL1, TSC22D1, XBP1 and ZFP36 is determined. FOXM1 may be added to the panel in some embodiments.

Alternatively, the expression level of at least one of a group of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45 or 46 of TRPM3, PDRG1, SRSF5, PDE4D, F12, PDK4, ADAMTS1, ADAMTS9, B3GNT5, CD38, CEBPD, CENPF, CREM, DKK1, EMP1, ERRFI1, F3, HJURP, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, RNFT2, SELE, SLC15A2, SOCS2, SOCS3, SSTR1, ST6GAL1, TSC22D1, XBP1 and ZFP36 is determined. FOXM1 may be included in the group in some embodiments.

In certain embodiments the expression level of at least one of

TRPM3, PDRG1, SRSF5, PDE4D, PDK4, F12, F3, HJURP, CENPF, MYBPC1, SELE, CEBPD, and XBP1 is determined.

In certain embodiments the expression level of at least 2, 3, 4, 5, 6, 7, 8, 9, 10, 11, 12, or 13 of TRPM3, PDRG1, SRSF5, PDE4D, PDK4, F12, F3, HJURP, CENPF, MYBPC1, SELE, CEBPD, and XBP1 is determined.

By characterisation is meant classification and/or evaluation of the prostate cancer. Prognosis refers to predicting the likely outcome of the prostate cancer for the subject. By diagnosis is meant identifying the presence of prostate cancer.

According to all aspects of the invention the characterisation of and/or prognosis for the prostate cancer may comprise, consist essentially of or consist of predicting an increased likelihood of recurrence. The characterisation of and/or prognosis for the prostate cancer may comprise, consist essentially of or consist of predicting a reduced time to recurrence. Recurrence may be clinical recurrence or biochemical recurrence. By biochemical recurrence is meant a rise in the level of PSA in a subject after treatment for prostate cancer. Biochemical recurrence may indicate that the prostate cancer has not been treated effectively or has recurred.

The characterisation of and/or prognosis for the prostate cancer may comprise, consist essentially of or consist of predicting an increased likelihood of metastasis.

Metastasis, or metastatic disease, is the spread of a cancer from one organ or part to another non-adjacent organ or part. The new occurrences of disease thus generated are referred to as metastases.

Characterisation of and/or prognosis for the prostate cancer may also comprise, consist essentially of or consist of determining whether the prostate cancer has a poor prognosis. A poor prognosis may be a reduced likelihood of cause-specific, i.e. cancer-specific, or long term survival. Cause- or Cancer-specific survival is a net survival measure representing cancer survival in the absence of other causes of death. Cancer survival may be for 6, 7, 8, 9, 10, 11, 12 months or 1, 2, 3, 4, 5 etc. years. Long-term survival may be survival for 1 year, 5 years, 10 years or 20 years following diagnosis. A prostate cancer with a poor prognosis may be aggressive, fast growing, and/or show resistance to treatment.

In certain embodiments an increased expression level of at least one of TRPM3, PDRG1, F12, CENPF, HJURP, RNFT2, and SSTR1 or of FOXM1 indicates an increased likelihood of recurrence and/or metastasis and/or a poor prognosis. In further embodiments a decreased expression level of at least one of SRSF5, PDE4D, PDK4, ADAMTS1, ADAMTS9, B3GNT5, CD38, CEBPD, CREM, DKK1, EMP1, ERRFI1, F3, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, SELE, SLC15A2, SOCS2, SOCS3, ST6GAL1, TSC22D1, XBP1 and ZFP36 indicates an increased likelihood of recurrence and/or metastasis and/or a poor prognosis.

In certain embodiments the methods described herein may comprise determining the expression level of at least one of TRPM3, PDRG1, F12, CENPF, HJURP, RNFT2, and SSTR1 or FOXM1 and at least one of SRSF5, PDE4D, PDK4, ADAMTS1, ADAMTS9, B3GNT5, CD38, CEBPD, CREM, DKK1, EMP1, ERRFI1, F3, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, SELE, SLC15A2, SOCS2, SOCS3, ST6GAL1, TSC22D1, XBP1 and ZFP36. Thus, the methods may rely upon a combination of an up-regulated marker and a down-regulated marker.

In certain embodiments the methods described herein comprise comparing the expression level to a reference value or to the expression level in one or more control samples or to the expression level in one or more control cells in the same sample. The control cells may be normal (i.e. cells characterised by an independent method as non-cancerous) cells. The one or more control samples may consist of non-cancerous cells or may include a mixture of prostate cancer cells and non-cancerous cells. The expression level may be compared to the expression level of the same gene in one or more control samples or control cells.

The reference value may be a threshold level of expression of at least one gene set by determining the level or levels in a range of samples from subjects with and without prostate cancer. The prostate cancer may be prostate cancer with or without an increased likelihood of recurrence and/or metastasis and/or a poor prognosis. Suitable methods for setting a threshold are well known to those skilled in the art. The threshold may be mathematically derived from a training set of patient data. The score threshold thus separates the test samples according to presence or absence of the particular condition. The interpretation of this quantity, i.e. the cut-off threshold may be derived in a development or training phase from a set of patients with known outcome. The threshold may therefore be fixed prior to performance of the claimed methods from training data by methods known to those skilled in the art.

The reference value may also be a threshold level of expression of at least one gene set by determining the level of expression of the at least one gene in a sample from a subject at a first time point. The determined levels of expression at later time points for the same subject are then compared to the threshold level. Thus, the methods of the invention may be used in order to monitor progress of disease in a subject, namely to provide an ongoing characterization and/or prognosis of disease in the subject. For example, the methods may be used to identify a prostate cancer that has developed into a more aggressive or potentially metastatic form. This may be used to guide treatment decisions as discussed in further detail herein.

For genes whose expression level does not differ between normal cells and cells from a prostate cancer that does not have an increased likelihood of recurrence and/or metastasis and/or a poor prognosis the expression level of the same gene in normal cells in the same sample can be used as a control.

Accordingly, in specific embodiments the expression level of at least one of

TRPM3, PDRG1, SRSF5, PDE4D, F12, and PDK4 in the prostate cancer cells in a sample is compared to the expression level of the same gene in the normal cells in the same sample.

In specific embodiments if the determined expression level of at least one of

TRPM3, PDRG1, SRSF5, PDE4D, F12, and PDK4 is not different in the prostate cancer cells in a sample as compared to the normal cells in the same sample then the prostate cancer does not have an increased likelihood of recurrence and/or metastasis and/or a poor prognosis.

Different may be statistically significantly different. By statistically significant is meant unlikely to have occurred by chance alone. A suitable statistical assessment may be performed according to any suitable method.

In specific embodiments if the gene is TRPM3, PDRG1 or F12 and the expression level is increased in the prostate cancer cells in a sample relative to the normal cells in the same sample then the prostate cancer has an increased likelihood of recurrence and/or metastasis and/or a poor prognosis.

In specific embodiments if the gene is SRSF5, PDE4D or PDK4 and the expression level is decreased in the prostate cancer cells in a sample relate to the normal cells in the sample then the prostate cancer has an increased likelihood of recurrence and/or metastasis and/or a poor prognosis.

The methods described herein may further comprise determining the expression level of a reference gene. A reference gene may be required if the target gene expression level differs between normal cells and cells from a prostate cancer that does not have an increased likelihood of recurrence and/or metastasis and/or a poor prognosis.

In certain embodiments the expression level of at least one of

ADAMTS1, ADAMTS9, B3GNT5, CD38, CEBPD, CENPF, CREM, DKK1, EMP1, ERRFI1, F3, HJURP, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, RNFT2, SELE, SLC15A2, SOCS2, SOCS3, SSTR1, ST6GAL1, TSC22D1, XBP1 and ZFP36 is compared to the expression level of a reference gene.

The reference gene may be any gene with minimal expression variance across all prostate cancer samples. Thus, the reference gene may be any gene whose expression level does not vary with likelihood of recurrence and/or metastasis and/or a poor prognosis. The skilled person is well able to identify a suitable reference gene based upon these criteria. In particular, the reference gene may be TPT1, RPS14 or RPL37A. The expression level of the reference gene may be determined in the same sample as the expression level of at least one of ADAMTS1, ADAMTS9, B3GNT5, CD38, CEBPD, CENPF, CREM, DKK1, EMP1, ERRFI1, F3, HJURP, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, RNFT2, SELE, SLC15A2, SOCS2, SOCS3, SSTR1, ST6GAL1, TSC22D1, XBP1 and ZFP36.

The expression level of the reference gene may be determined in a different sample. The different sample may be a control sample as described above. The expression level of the reference gene may be determined in normal and/or prostate cancer cells in a sample.

The expression level of the at least one gene in the sample from the subject may be analysed using a statistical model. In specific embodiments where the expression level of at least 2 genes is measured the genes may be weighted. As used herein, the term "weight" refers to the relative importance of an item in a statistical calculation. The weight of each gene may be determined on a data set of patient samples using analytical methods known in the art. An overall score may be calculated and used to provide a characterisation of and/or prognosis for the prostate cancer.

Methods for determining the expression levels of the markers are described in greater detail herein. Typically, the methods may involve contacting a sample obtained from a subject with a detection agent, such as primers/probes/antibodies (as discussed in detail herein) specific for the marker and detecting expression products. A comparison is made against expression levels determined in a control sample to provide a characterization and/or a prognosis for the prostate cancer.

According to all aspects of the invention the expression level of the gene or genes may be measured by any suitable method. In certain embodiments the expression level is determined at the level of protein, RNA or epigenetic modification. The epigenetic modification may be DNA methylation.

The expression level may be determined by immunohistochemistry. By Immunohistochemistry is meant the detection of proteins in cells of a tissue sample by using a binding reagent such as an antibody or aptamer that binds specifically to the proteins. Thus, the expression level as determined by immunohistochemistry is a protein level. The sample may be a prostate tissue sample and may comprise prostate cancer (tumour) cells, prostatic intraepithelial neoplasia (PIN) cells, normal prostate epithelium, stroma and, optionally, infiltrating immune cells. In some embodiments the expression level of the at least one gene in the prostate cancer (tumour) cells in a sample is compared to the expression level of the same gene (and/or a reference gene) in the normal cells in the same sample. In some embodiments the expression level of the at least one gene in the prostate cancer (tumour) cells in a sample is compared to the expression level of the same gene (and/or a reference gene) in the normal cells in a control sample. The normal cells may comprise, consist essentially of or consist of normal (non-cancer) prostate epithelial cells. In certain embodiments the normal cells do not comprise PIN cells and/or stroma cells. In certain embodiments the prostate cancer (tumour) cells do not comprise PIN cells and/or stroma cells. In further embodiments the expression level of the at least one gene in the prostate cancer (tumour) cells in a sample is (additionally) compared to the expression level of a reference gene in the same cells or in the prostate cancer cells in a control sample. The reference gene may be TPT1, RPS14 or RPL37A. In yet further embodiments the expression level of the at least one gene in the prostate cancer (tumour) cells in a sample is scored using a method based on intensity, proportion and/or localisation of expression in the prostate cancer (tumour) cells (without comparison to normal cells). The scoring method may be derived in a development or training phase from a set of patients with known outcome.

Accordingly, in a further aspect, the present invention relates to an antibody or aptamer that binds specifically to a protein product of at least one of FOXM1, TRPM3, PDRG1, SRSF5, PDE4D, F12, PDK4, ADAMTS1, ADAMTS9, B3GNT5, CD38, CEBPD, CENPF, CREM, DKK1, EMP1, ERRFI1, F3, HJURP, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, RNFT2, SELE, SLC15A2, SOCS2, SOCS3, SSTR1, ST6GAL1, TSC22D1, XBP1 and ZFP36.

The antibody may be of monoclonal or polyclonal origin. Fragments and derivative antibodies may also be utilised, to include without limitation Fab fragments, ScFv, single domain antibodies, nanoantibodies, heavy chain antibodies, aptamers etc. which retain peptide-specific binding function and these are included in the definition of "antibody". Such antibodies are useful in the methods of the invention. They may be used to measure the level of a particular protein, or in some instances one or more specific isoforms of a protein. The skilled person is well able to identify epitopes that permit specific isoforms to be discriminated from one another.

Methods for generating specific antibodies are known to those skilled in the art. Antibodies may be of human or non-human origin (e.g. rodent, such as rat or mouse) and be humanized etc. according to known techniques (Jones et al., Nature (1986) May 29-June 4; 321(6069):522-5; Roguska et al., Protein Engineering, 1996, 9(10):895-904; and Studnicka et al., Humanizing Mouse Antibody Frameworks While Preserving 3-D Structure. Protein Engineering, 1994, Vol. 7, pg 805).

In certain embodiments the expression level is determined using an antibody or aptamer conjugated to a label. By label is meant a component that permits detection, directly or indirectly. For example, the label may be an enzyme, optionally a peroxidase, or a fluorophore.

A label is an example of a detection agent. By detection agent is meant an agent that may be used to assist in the detection of the antibody-protein complex. Where the antibody is conjugated to an enzyme the detection agent may be comprise a chemical composition such that the enzyme catalyses a chemical reaction to produce a detectable product. The products of reactions catalyzed by appropriate enzymes can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers. In certain embodiments the detection agent may comprise a secondary antibody. The expression level is then determined using an unlabeled primary antibody that binds to the target protein and a secondary antibody conjugated to a label, wherein the secondary antibody binds to the primary antibody.

The invention also relates to use of an antibody as described above for characterising and/or prognosing a prostate cancer in a subject.

Additional techniques for determining expression level at the level of protein include, for example, Western blot, immunoprecipitation, immunocytochemistry, mass spectrometry, ELISA and others (see ImmunoAssay: A Practical Guide, edited by Brian Law, published by Taylor & Francis, Ltd., 2005 edition). To improve specificity and sensitivity of an assay method based on immunoreactivity, monoclonal antibodies are often used because of their specific epitope recognition. Polyclonal antibodies have also been successfully used in various immunoassays because of their increased affinity for the target as compared to monoclonal antibodies.

Suitable antibodies which may be used in the methods of the invention or included in the kits of the invention are listed in Table B below:

TABLE B examples of Antibodies binding to markers of the invention

| Gene ID | Antibody Supplier | Antibody Reference |
|---|---|---|
| ADAMTS1 | Source Bioscience | LS-A1643 |
| | Source Bioscience | LS-A1642 |
| | Source Bioscience | LS-A1649 |
| ADAMTS9 | Novus | NBP1-82915 |
| | Novus | NBP1-82916 |
| | Sigma | HPA028577 |
| B3GNT5 | Novus | NBP1-88954 |
| CD38 | Source Bioscience | LS-A9696 |
| | Source Bioscience | LS-A9697 |
| | Leica Novocastra | CD38-290-L-CE |
| CEBPD | No suitable antibody | |
| CENPF | Source Bioscience | LS-B2992 |
| | Source Bioscience | LS-B3157 |
| | Novus | NB500-101 |
| CREM | Sigma | HPA001818 |
| DKK1 | Source Bioscience | LS-A2867 |
| | Source Bioscience | LS-A2865 |
| | Source Bioscience | LS-A2868 |
| | Novus | NBP1-95560 |
| EMP1 | Sigma | HPA056250 |
| ERRFI1 | Novus | NBP1-81835 |
| | Sigma | HPA027206 |
| F12 | Source Bioscience | LS-B2649 |
| | Source Bioscience | LS-B3044 |
| | Sigma | HPA003825 |
| F3 | Novus | NBP2-15139 |
| FOXM1 | Source Bioscience | LS-B3073 |
| | Sigma | HPA029974 |
| | Novus | NBP1-84671 |
| HJURP | Sigma | HPA008436 |
| IL1R1 | Source Bioscience | LS-B2859 |
| | Novus | NBP1-30929 |
| IL8 | Source Bioscience | LS-B6427 |
| JUNB | Source Bioscience | LS-C176087 |
| | Novus | NBP1-89544 |
| KLF10 | Source Bioscience | LS-C119009 |
| KLF4 | Source Bioscience | LS-B5641 |
| | Novus | NBP2-24749 |
| LDLR | Source Bioscience | LS-B1598 |
| | Source Bioscience | LS-B8088 |
| | Sigma | HPA009647 |
| LGALS3 | Source Bioscience | LS-B5661 |
| | Source Bioscience | LS-B1671 |
| | Sigma | HPA003162 |
| LPAR1 | Source Bioscience | LS-A212 |
| | Source Bioscience | LS-A211 |
| MALAT1 | NA | NA |
| MTUS1 | Novus | NBP1-82197 |
| MYBPC1 | Novus | NBP1-86427 |
| NR4A3 | Source Bioscience | LS-A2341 |
| | Source Bioscience | LS-A2328 |
| | Novus | NBP1-92198 |
| OAT | Source Bioscience | LS-B4188 |
| | Novus | NBP1-83239 |
| PDE4D | Source Bioscience | LS-C185640 |
| | Source Bioscience | LS-B8230 |
| | Novus | NBP1-31131 |
| PDK4 | Source Bioscience | LS-B3459 |
| PDRG1 | Source Bioscience | LS-C163501 |
| | Novus | NBP2-01854 |
| PI15 | Source Bioscience | LS-C163698 |
| PTGS2 | Source Bioscience | LS-B3296 |
| | Source Bioscience | LS-B2145 |
| | Novus | NB110-1948 |
| RHOBTB3 | Source Bioscience | LS-C120337 |
| | Source Bioscience | NBP1-82954 |
| RIN2 | Sigma | HPA034641 |
| SELE | Source Bioscience | LS-B2323 |
| SOCS2 | Source Bioscience | LS-B1257 |
| SOCS3 | Source Bioscience | LS-B3373 |
| | Source Bioscience | NBP2-00850 |
| SRSF5 | Source Bioscience | LS-B3091 |
| | Novus | NBP1-92381 |
| SSTR1 | Source Bioscience | LS-A994 |
| ST6GAL1 | Source Bioscience | LS-B6041 |
| | Novus | NBP1-68447 |
| TRPM3 | Novus | NBP1-46344 |

TABLE B-continued examples of Antibodies binding to markers of the invention

| Gene ID | Antibody Supplier | Antibody Reference |
|---|---|---|
| TSC22D1 | Source Bioscience | LS-B8419 |
| XBP1 | Source Bioscience | LS-B3178 |
| | Source Bioscience | LS-B188 |
| | Novus | NBP1-95395 |
| ZFP36 | Source Bioscience | LS-B5606 |

Measuring mRNA in a biological sample may be used as a surrogate for detection of the level of the corresponding protein in the biological sample. Thus, the expression level of any of the genes described herein can also be detected by detecting the appropriate RNA.

Accordingly, in specific embodiments the expression level is determined by microarray, northern blotting, RNA-seq (RNA sequencing), in situ RNA detection or nucleic acid amplification. Nucleic acid amplification includes PCR and all variants thereof such as real-time and end point methods and qPCR. Other nucleic acid amplification techniques are well known in the art, and include methods such as NASBA, 3SR and Transcription Mediated Amplification (TMA). Other suitable amplification methods include the ligase chain reaction (LCR), selective amplification of target polynucleotide sequences (U.S. Pat. No. 6,410,276), consensus sequence primed polymerase chain reaction (U.S. Pat. No. 4,437,975), arbitrarily primed polymerase chain reaction (WO 90/06995), invader technology, strand displacement technology, and nick displacement amplification (WO 2004/067726). This list is not intended to be exhaustive; any nucleic acid amplification technique may be used provided the appropriate nucleic acid product is specifically amplified. Design of suitable primers and/or probes is within the capability of one skilled in the art. Various primer design tools are freely available to assist in this process such as the NCBI Primer-BLAST tool. Primers and/or probes may be at least 15, 16, 17, 18, 19, 20, 21, 22, 23, 24 or 25 (or more) nucleotides in length. mRNA expression levels may be measured by reverse transcription quantitative polymerase chain reaction (RT-PCR followed with qPCR). RT-PCR is used to create a cDNA from the mRNA. The cDNA may be used in a qPCR assay to produce fluorescence as the DNA amplification process progresses. By comparison to a standard curve, qPCR can produce an absolute measurement such as number of copies of mRNA per cell. Northern blots, microarrays, Invader assays, and RT-PCR combined with capillary electrophoresis have all been used to measure expression levels of mRNA in a sample. See Gene Expression Profiling: Methods and Protocols, Richard A. Shimkets, editor, Humana Press, 2004.

RNA-seq uses next-generation sequencing to measure changes in gene expression. RNA may be converted into cDNA or directly sequenced. Next generation sequencing techniques include pyrosequencing, SOLiD sequencing, Ion Torrent semiconductor sequencing, Illumina dye sequencing, single-molecule real-time sequencing or DNA nanoball sequencing.

In situ RNA detection involves detecting RNA without extraction from tissues and cells. In situ RNA detection includes In situ hybridization (ISH) which uses a labeled (e.g. radio labelled, antigen labelled or fluorescence labelled) probe (complementary DNA or RNA strand) to localize a specific RNA sequence in a portion or section of tissue, or in the entire tissue (whole mount ISH), or in cells. The probe labeled with either radio-, fluorescent- or antigen-labeled bases (e.g., digoxigenin) may be localized and quantified in the tissue using either autoradiography, fluorescence microscopy or immunohistochemistry, respectively. ISH can also use two or more probes to simultaneously detect two or more transcripts. A branched DNA assay can also be used for RNA in situ hybridization assays with single molecule sensitivity. This approach includes ViewRNA assays. Samples (cells, tissues) are fixed, then treated to allow RNA target accessibility (RNA un-masking). Target-specific probes hybridize to each target RNA. Subsequent signal amplification is predicated on specific hybridization of adjacent probes (individual oligonucleotides that bind side by side on RNA targets). A typical target-specific probe will contain 40 oligonucleotides. Signal amplification is achieved via a series of sequential hybridization steps. A pre-amplifier molecule hybridizes to each oligo pair on the target-specific RNA, then multiple amplifier molecules hybridize to each pre-amplifier. Next, multiple label probe oligonucleotides (conjugated to an enzyme such as alkaline phosphatase or directly to fluorophores) hybridize to each amplifier molecule. Separate but compatible signal amplification systems enable multiplex assays. The signal can be visualized by measuring fluorescence or light emitted depending upon the detection system employed. Detection may involve using a high content imaging system, or a fluorescence or brightfield microscope in some embodiments.

Thus, in a further aspect the present invention relates to a kit for (in situ) characterising and/or prognosing prostate cancer in a subject comprising one or more oligonucleotide probes specific for an RNA product of at least one of FOXM1, TRPM3, PDRG1, SRSF5, PDE4D, F12, PDK4, ADAMTS1, ADAMTS9, B3GNT5, CD38, CEBPD, CENPF, CREM, DKK1, EMP1, ERRFI1, F3, HJURP, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, RNFT2, SELE, SLC15A2, SOCS2, SOCS3, SSTR1, ST6GAL1, TSC22D1, XBP1 and ZFP36.

The kit may further comprise one or more of the following components:

a) A blocking probe b) A PreAmplifier c) An Amplifier and/or d) A Label molecule The components of the kit may be suitable for conducting a viewRNA assay (https://www.panomics.com/products/rna-in-situ-analysis/view-rna-overview).

The components of the kit may be nucleic acid based molecules, optionally DNA (or RNA). The blocking probe is a molecule that acts to reduce background signal by binding to sites on the target not bound by the target specific probes (probes specific for the RNA product of the at least one gene of the invention). The PreAmplifier is a molecule capable of binding to a (a pair of) target specific probe(s) when target bound. The Amplifier is a molecule capable of binding to the PreAmplifier. Alternatively, the Amplifier may be capable of binding directly to a (a pair of) target specific probe(s) when target bound. The Amplifier has binding sites for multiple label molecules (which may be label probes).

The invention also relates to use of the kit for characterising and/or prognosing prostate cancer.

RNA expression may be determined by hybridization of RNA to a set of probes. The probes may be arranged in an array. Microarray platforms include those manufactured by companies such as Affymetrix, Illumina and Agilent. Examples of microarray platforms manufactured by Affymetrix include the U133 Plus2 array, the Almac proprietary Xcel™ array and the Almac proprietary Cancer DSAs®, including the Prostate Cancer DSA®.

In specific embodiments, expression of the at least one gene may be determined using one or more probes selected from those in Table C below:

TABLE C list of probes used to measure expression levels of the genes on an array.

| Gene | Probeset ID | SEQ ID No |
|---|---|---|
| ADAMTS1 | PC3P.3828.C1_s_at | 30 |
| | PCHP.1595_s_at | 75 |
| ADAMTS9 | PC3P.17014.C1_s_at | 24 |
| | PC3SNGnh.5879_at | 53 |
| | PCADA.974_s_at | 62 |
| B3GNT5 | PCRS2.398_s_at | 81 |
| CD38 | 3Snip.8317-94a_s_at | 6 |
| | PC3P.16779.C1_s_at | 23 |
| CEBPD | >PCHP.407_s_at_1160 | 89 |
| | >PC3P.4961.C1_s_at_156 | 90 |
| CENPF | PC3P.14957.C1_s_at | 19 |
| | PCADA.11788_at | 55 |
| CREM | PC3P.8627.C1_at | 48 |
| | PC3P.8627.C1_s_at | 49 |
| DKK1 | 3Snip.431-44a_s_at | 4 |
| EMP1 | PC3P.10147.C1_at | 9 |
| ERRFI1 | PC3P.3363.C1-522a_s_at | 29 |
| | PCADA.5865_at | 58 |
| | PCADA.5865_x_at | 59 |
| | PCRS2.6810_s_at | 83 |
| F12 | PCADNP.16711_at | 63 |
| F3 | 3Snip.8552-9072a_s_at | 7 |
| | PC3P.8519.C1_s_at | 46 |
| | PC3P.8519.C2_s_at | 47 |
| | PCHP.1022_s_at | 70 |
| FOXM1 | PCHP.1211_s_at | 87 |
| HJURP | PCADA.12835_s_at | 56 |
| IL1R1 | PCADA.9303_s_at | 61 |
| IL8 | PCHP.274_s_at | 76 |
| KLF10 | PCRS2.574_s_at | 82 |
| KLF4 | PC3P.14562.C1_s_at | 18 |
| LDLR | PCHP.101_s_at | 69 |
| LGALS3 | 3Snip.6331-2a_s_at | 5 |
| LPAR1 | PC3P.4497.C1_at | 34 |
| | PCADA.11416_s_at | 54 |
| | PCADA.5036_s_at | 57 |
| | PCRS2.2781_s_at | 80 |
| MALAT1 | 3Snip.3677-484a_s_at | 3 |
| | PC3P.2436.C1_s_at | 25 |
| MTUS1 | PCRS2.6884_s_at | 84 |
| MYBPC1 | PC3P.13654.C1_at | 16 |
| | PC3P.13654.C1_x_at | 17 |
| | PC3P.3003.C1_s_at | 27 |
| | PC3P.7685.C1_at | 40 |
| | PC3P.7685.C1_x_at | 41 |
| | PC3P.7685.C1-693a_s_at | 42 |
| NFIL3 | >PC3P.9419.C1-398a_s_at_365 | 88 |
| NR4A3 | PC3P.11087.C1_x_at | 11 |
| | PC3P.13257.C1_at | 15 |
| OAT | PC3P.2802.C1_s_at | 26 |
| PDE4D | PC3P.11285.C1_at | 12 |
| | PCADNP.1679_s_at | 64 |
| PDK4 | PC3P.16300.C1_at | 20 |
| | PC3P.16300.C1_x_at | 21 |
| | PC3P.8159.C1_s_at | 43 |
| | PC3P.8159.C1-773a_s_at | 44 |
| | PC3SNGnh.4912_at | 50 |
| | PC3SNGnh.4912_x_at | 51 |
| | PC3SNGnh.5369_x_at | 52 |
| | PCADNP.18913_s_at | 66 |
| | PCEM.2221_at | 68 |
| | PCPD.29484.C1_at | 78 |
| PDRG1 | >PC3P.15830.C1_s_at_353 | 93 |
| PI15 | 3Snip.2873-1277a_at | 2 |
| | PC3P.7245.C1_at | 38 |
| | PC3P.7245.C1_x_at | 39 |

TABLE C-continued list of probes used to measure expression levels of the genes on an array.

| Gene | Probeset ID | SEQ ID No |
|---|---|---|
| | PC3P.8311.C1-482a_s_at | 45 |
| | PCADNP.17332_s_at | 65 |
| PTGS2 | 3Snip.950-71a_x_at | 8 |
| | PC3P.16654.C1_s_at | 22 |
| RHOBTB3 | PC3P.12138.C1_at | 13 |
| | PC3P.12138.C1_x_at | 14 |
| | PC3P.5195.C1_s_at | 35 |
| RIN2 | PC3P.7127.C1_s_at | 37 |
| RNFT2 | PCADNP.401_s_at | 67 |
| SELE | PCHP.1458_s_at | 74 |
| SLC15A2 | 3Snip.1826-385a_s_at | 1 |
| | PC3P.10260.C1_at | 10 |
| | PC3P.3316.C1_at | 28 |
| | PCRS2.7997_s_at | 86 |
| SOCS2 | PC3P.5499.C1_at | 36 |
| | PCHP.128_s_at | 73 |
| SOCS3 | PCHP.491_s_at | 77 |
| SRSF5 | PC3P.394.CB1_s_at | 32 |
| SSTR1 | >PCHP.841_s_at_4070 | 91 |
| | >PC3P.12563.C1_s_at_327 | 92 |
| ST6GAL1 | PCRS2.699_s_at | 85 |
| TRPM3 | PCADA.7751_s_at | 60 |
| TSC22D1 | PC3P.41.CB2_s_at | 33 |
| | PCHP.112_s_at | 71 |
| XBP1 | PC3P.3909.C1-403a_s_at | 31 |
| | PCPD.59444.C1_at | 79 |
| ZFP36 | PCHP.1147_s_at | 72 |

These probes may also be incorporated into the kits of the invention. The probe sequences may also be used in order to design primers for detection of expression, for example by RT-PCR. Such primers may also be included in the kits of the invention.

Increased rates of DNA methylation at or near promoters have been shown to correlate with reduced gene expression levels. DNA methylation is the main epigenetic modification in humans. It is a chemical modification of DNA performed by enzymes called methyltransferases, in which a methyl group (m) is added to specific cytosine (C) residues in DNA. In mammals, methylation occurs only at cytosine residues adjacent to a guanosine residue, i.e. at the sequence CG or at the CpG dinucleotide.

Accordingly, in yet a further aspect, the present invention relates to a method for characterising and/or prognosing prostate cancer in a subject comprising:

determining the methylation status of at least one of

ADAMTS9, EMP1, F3, LDLR, LGALS3, MALAT1, MTUS1, NR4A3, PTGS2, RIN2, SLC15A2, SOCS3 and TSC22D1 in a sample from the subject wherein the determined methylation status is used to provide a characterisation of and/or a prognosis for the prostate cancer.

In certain embodiments if at least one of

ADAMTS9, EMP1, F3, LDLR, LGALS3, MALAT1, MTUS1, NR4A3, PTGS2, RIN2, SLC15A2, SOCS3 and TSC22D1 is (hyper)methylated the likelihood of recurrence and/or metastasis is increased.

Determination of the methylation status may be achieved through any suitable means. Suitable examples include bisulphite genomic sequencing and/or by methylation specific PCR. Various techniques for assessing methylation status are known in the art and can be used in conjunction with the present invention: sequencing, methylation-specific PCR (MS-PCR), melting curve methylation-specific PCR (McMS-PCR), MLPA with or without bisulphite treatment, QAMA (Zeschnigk et al, 2004), MSRE-PCR (Melnikov et al, 2005), MethyLight (Eads et al., 2000), ConLight-MSP (Rand et al., 2002), bisulphite conversion-specific methylation-specific PCR (BS-MSP) (Sasaki et al., 2003), COBRA (which relies upon use of restriction enzymes to reveal methylation dependent sequence differences in PCR products of sodium bisulphite-treated DNA), methylation-sensitive single-nucleotide primer extension conformation (MS-SNuPE), methylation-sensitive single-strand conformation analysis (MS-SSCA), Melting curve combined bisulphite restriction analysis (McCOBRA) (Akey et al., 2002), PyroMethA, HeavyMethyl (Cottrell et al. 2004), MALDI-TOF, MassARRAY, Quantitative analysis of methylated alleles (QAMA), enzymatic regional methylation assay (ERMA), QBSUPT, MethylQuant, Quantitative PCR sequencing and oligonucleotide-based microarray systems, Pyrosequencing, Meth-DOP-PCR. A review of some useful techniques for DNA methylation analysis is provided in Nucleic acids research, 1998, Vol. 26, No. 10, 2255-2264, Nature Reviews, 2003, Vol. 3, 253-266; Oral Oncology, 2006, Vol. 42, 5-13.

Techniques for assessing methylation status are based on distinct approaches. Some include use of endonucleases. Such endonucleases may either preferentially cleave methylated recognition sites relative to non-methylated recognition sites or preferentially cleave non-methylated relative to methylated recognition sites. Some examples of the former are Acc III, Ban I, BstN I, Msp I, and Xma I. Examples of the latter are Acc II, Ava I, BssH II, BstU I, Hpa II, and Not I. Differences in cleavage pattern are indicative for the presence or absence of a methylated CpG dinucleotide. Cleavage patterns can be detected directly, or after a further reaction which creates products which are easily distinguishable. Means which detect altered size and/or charge can be used to detect modified products, including but not limited to electrophoresis, chromatography, and mass spectrometry.

Alternatively, the identification of methylated CpG dinucleotides may utilize the ability of the methyl binding domain (MBD) of the MeCP2 protein to selectively bind to methylated DNA sequences (Cross et al, 1994; Shiraishi et al, 1999). The MBD may also be obtained from MBP, MBP2, MBP4, poly-MBD (Jorgensen et al., 2006) or from reagents such as antibodies binding to methylated nucleic acid. The MBD may be immobilized to a solid matrix and used for preparative column chromatography to isolate highly methylated DNA sequences. Variant forms such as expressed His-tagged methyl-CpG binding domain may be used to selectively bind to methylated DNA sequences. Eventually, restriction endonuclease digested genomic DNA is contacted with expressed His-tagged methyl-CpG binding domain. Other methods are well known in the art and include amongst others methylated-CpG island recovery assay (MIRA). Another method, MB-PCR, uses a recombinant, bivalent methyl-CpG-binding polypeptide immobilized on the walls of a PCR vessel to capture methylated DNA and the subsequent detection of bound methylated DNA by PCR.

Further approaches for detecting methylated CpG dinucleotide motifs use chemical reagents that selectively modify either the methylated or non-methylated form of CpG dinucleotide motifs. Suitable chemical reagents include hydrazine and bisulphite ions. The methods of the invention may use bisulphite ions, in certain embodiments. The bisulphite conversion relies on treatment of DNA samples with sodium bisulphite which converts unmethylated cytosine to uracil, while methylated cytosines are maintained (Furuichi et al., 1970). This conversion finally results in a change in the sequence of the original DNA. It is general knowledge that the resulting uracil has the base pairing behaviour of thymidine which differs from cytosine base pairing behaviour. This makes the discrimination between methylated and non-methylated cytosines possible. Useful conventional techniques of molecular biology and nucleic acid chemistry for assessing sequence differences are well known in the art and explained in the literature. See, for example, Sambrook, J., et al., Molecular cloning: A laboratory Manual, (2001) 3rd edition, Cold Spring Harbor, NY; Gait, M. J. (ed.), Oligonucleotide Synthesis, A Practical Approach, IRL Press (1984); Hames B. D., and Higgins, S. J. (eds.), Nucleic Acid Hybridization, A Practical Approach, IRL Press (1985); and the series, Methods in Enzymology, Academic Press, Inc.

Some techniques use primers for assessing the methylation status at CpG dinucleotides. Two approaches to primer design are possible. Firstly, primers may be designed that themselves do not cover any potential sites of DNA methylation. Sequence variations at sites of differential methylation are located between the two primers and visualisation of the sequence variation requires further assay steps. Such primers are used in bisulphite genomic sequencing, COBRA, Ms-SnuPE and several other techniques. Secondly, primers may be designed that hybridize specifically with either the methylated or unmethylated version of the initial treated sequence. After hybridization, an amplification reaction can be performed and amplification products assayed using any detection system known in the art. The presence of an amplification product indicates that a sample hybridized to the primer. The specificity of the primer indicates whether the DNA had been modified or not, which in turn indicates whether the DNA had been methylated or not. If there is a sufficient region of complementarity, e.g., 12, 15, 18, or 20 nucleotides, to the target, then the primer may also contain additional nucleotide residues that do not interfere with hybridization but may be useful for other manipulations. Examples of such other residues may be sites for restriction endonuclease cleavage, for ligand binding or for factor binding or linkers or repeats. The oligonucleotide primers may or may not be such that they are specific for modified methylated residues.

A further way to distinguish between modified and unmodified nucleic acid is to use oligonucleotide probes. Such probes may hybridize directly to modified nucleic acid or to further products of modified nucleic acid, such as products obtained by amplification. Probe-based assays exploit the oligonucleotide hybridisation to specific sequences and subsequent detection of the hybrid. There may also be further purification steps before the amplification product is detected e.g. a precipitation step. Oligonucleotide probes may be labeled using any detection system known in the art. These include but are not limited to fluorescent moieties, radioisotope labeled moieties, bioluminescent moieties, luminescent moieties, chemiluminescent moieties, enzymes, substrates, receptors, or ligands.

In the MSP approach, DNA may be amplified using primer pairs designed to distinguish methylated from unmethylated DNA by taking advantage of sequence differences as a result of sodium-bisulphite treatment (WO 97/46705). For example, bisulphite ions modify non-methylated cytosine bases, changing them to uracil bases. Uracil bases hybridize to adenine bases under hybridization conditions. Thus an oligonucleotide primer which comprises adenine bases in place of guanine bases would hybridize to the bisulphite-modified DNA, whereas an oligonucleotide primer containing the guanine bases would hybridize to the non-modified (methylated) cytosine residues in the DNA.

Amplification using a DNA polymerase and a second primer yield amplification products which can be readily observed, which in turn indicates whether the DNA had been methylated or not. Whereas PCR is a preferred amplification method, variants on this basic technique such as nested PCR and multiplex PCR are also included within the scope of the invention.

As mentioned earlier, one embodiment for assessing the methylation status of the relevant gene requires amplification to yield amplification products. The presence of amplification products may be assessed directly using methods well known in the art. They simply may be visualized on a suitable gel, such as an agarose or polyacrylamide gel. Detection may involve the binding of specific dyes, such as ethidium bromide, which intercalate into double-stranded DNA and visualisation of the DNA bands under a UV illuminator for example. Another means for detecting amplification products comprises hybridization with oligonucleotide probes. Alternatively, fluorescence or energy transfer can be measured to determine the presence of the methylated DNA.

A specific example of the MSP technique is designated real-time quantitative MSP (QMSP), and permits reliable quantification of methylated DNA in real time or at end point. Real-time methods are generally based on the continuous optical monitoring of an amplification procedure and utilise fluorescently labelled reagents whose incorporation in a product can be quantified and whose quantification is indicative of copy number of that sequence in the template. One such reagent is a fluorescent dye, called SYBR Green I that preferentially binds double-stranded DNA and whose fluorescence is greatly enhanced by binding of double-stranded DNA. Alternatively, labelled primers and/or labelled probes can be used for quantification. They represent a specific application of the well-known and commercially available real-time amplification techniques such as TAQMAN®, MOLECULAR BEACONS®, AMPLIFLUOR® and SCORPION®, DzyNA®, Plexor™ etc. In the real-time PCR systems, it is possible to monitor the PCR reaction during the exponential phase where the first significant increase in the amount of PCR product correlates to the initial amount of target template.

Real-Time PCR detects the accumulation of amplicon during the reaction. Real-time methods do not need to be utilised, however. Many applications do not require quantification and Real-Time PCR is used only as a tool to obtain convenient results presentation and storage, and at the same time to avoid post-PCR handling. Thus, analyses can be performed only to confirm whether the target DNA is present in the sample or not. Such end-point verification is carried out after the amplification reaction has finished.

According to all aspects of the invention determining the expression level of at least one of FOXM1, TRPM3, PDRG1, SRSF5, PDE4D, F12, PDK4, ADAMTS1, ADAMTS9, B3GNT5, CD38, CEBPD, CENPF, CREM, DKK1, EMP1, ERRFI1, F3, HJURP, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, RNFT2, SELF, SLC15A2, SOCS2, SOCS3, SSTR1, ST6GAL1, TSC22D1, XBP1 and ZFP36 may involve determining the level of all or a selection of the transcripts and/or proteins isoforms produced from the gene. Examples of transcripts and corresponding protein isoforms that may be detected for each gene are shown in Table D below:

TABLE D representative transcripts and corresponding protein isoforms that may be detected in the invention

| Gene ID | Ensembl Transcript IDs detected by Almac probeset | Ensembl Protein ID |
|---|---|---|
| TRPM3 | ENST00000377111 | ENSP00000366315 |
| | ENST00000423814 | ENSP00000389542 |
| | ENST00000357533 | ENSP00000350140 |
| | ENST00000354500 | Non-protein coding |
| | ENST00000377110 | ENSP00000366314 |
| PDRG1 | ENST00000202017 | ENSP00000202017 |
| SRSF5 | ENST00000553635 | ENSP00000451391 |
| | ENST00000554465 | Non-protein coding |
| | ENST00000556184 | Non-protein coding |
| | ENST00000557154 | ENSP00000451088 |
| | ENST00000394366 | ENSP00000377892 |
| | ENST00000557460 | Non-protein coding |
| | ENST00000556587 | Non-protein coding |
| | ENST00000555547 | Non-protein coding |
| | ENST00000556330 | Non-protein coding |
| | ENST00000554929 | Non-protein coding |
| | ENST00000553521 | ENSP00000452123 |
| PDE4D | ENST00000507116 | ENSP00000424852 |
| | ENST00000502575 | ENSP00000425917 |
| | ENST00000502484 | ENSP00000423094 |
| | ENST00000340635 | ENSP00000345502 |
| | ENST00000546160 | ENSP00000442734 |
| | ENST00000505453 | ENSP00000421013 |
| | ENST00000360047 | ENSP00000353152 |
| | ENST00000405053 | Non-protein coding |
| | ENST00000405755 | ENSP00000384806 |
| | ENST00000309641 | Non-protein coding |
| | ENST00000514231 | Non-protein coding |
| PDK4 | ENST00000473796 | Non-protein coding |
| | ENST00000005178 | ENSP00000005178 |
| ADAMTS1 | ENST00000284984 | ENSP00000284984 |
| | ENST00000464589 | Non-protein coding |
| ADAMTS9 | ENST00000482490 | Non-protein coding |
| | ENST00000295903 | ENSP00000295903 |
| | ENST00000481060 | ENSP00000417521 |
| | ENST00000498707 | ENSP00000418735 |
| B3GNT5 | ENST00000460419 | ENSP00000420778 |
| | ENST00000326505 | ENSP00000316173 |
| CEBPD | ENST00000408965 | ENSP00000386165 |
| CENPF | ENST00000366955 | ENSP00000355922 |
| CREM | ENST00000464475 | ENSP00000418450 |
| | ENST00000488328 | ENSP00000417460 |
| | ENST00000490460 | Non-protein coding |
| | ENST00000479070 | ENSP00000420511 |
| | ENST00000463314 | ENSP00000418336 |
| | ENST00000374734 | ENSP00000363866 |
| | ENST00000484283 | ENSP00000417165 |
| | ENST00000463960 | ENSP00000419684 |
| | ENST00000460270 | ENSP00000420437 |
| | ENST00000473940 | ENSP00000420681 |
| | ENST00000469517 | Non-protein coding |
| | ENST00000342105 | ENSP00000341875 |
| | ENST00000461968 | Non-protein coding |
| | ENST00000374728 | ENSP00000363860 |
| | ENST00000395887 | ENSP00000379225 |
| | ENST00000495960 | Non-protein coding |
| | ENST00000429130 | ENSP00000393538 |
| | ENST00000348787 | ENSP00000345384 |
| | ENST00000337656 | ENSP00000337138 |
| | ENST00000333809 | ENSP00000333055 |
| | ENST00000487132 | ENSP00000418798 |
| | ENST00000374721 | ENSP00000363853 |
| | ENST00000439705 | ENSP00000409220 |
| | ENST00000344351 | ENSP00000344365 |
| | ENST00000345491 | ENSP00000265372 |
| | ENST00000474362 | ENSP00000419018 |
| | ENST00000361599 | ENSP00000354593 |
| | ENST00000395895 | ENSP00000379232 |
| | ENST00000354759 | ENSP00000346804 |
| | ENST00000487763 | ENSP00000417807 |
| | ENST00000356917 | ENSP00000349387 |
| DKK1 | ENST00000476752 | Non-protein coding |
| | ENST00000373970 | ENSP00000363081 |

TABLE D-continued representative transcripts and corresponding protein isoforms that may be detected in the invention

| Gene ID | Ensembl Transcript IDs detected by Almac probeset | Ensembl Protein ID |
|---|---|---|
| EMP1 | ENST00000256951 | ENSP00000256951 |
| | ENST00000537612 | ENSP00000445319 |
| ERRFI1 | ENST00000487559 | ENSP00000467030 |
| | ENST00000474874 | ENSP00000466958 |
| | ENST00000377482 | ENSP00000366702 |
| | ENST00000467067 | ENSP00000465100 |
| | ENST00000469499 | ENSP00000466454 |
| HJURP | ENST00000441687 | ENSP00000401944 |
| | ENST00000411486 | ENSP00000414109 |
| | ENST00000432087 | ENSP00000407208 |
| | ENST00000433484 | Non-protein coding |
| IL1R1 | ENST00000422532 | Non-protein coding |
| | ENST00000409929 | ENSP00000386776 |
| | ENST00000233946 | ENSP00000233946 |
| | ENST00000409288 | ENSP00000386478 |
| | ENST00000413623 | Non-protein coding |
| | ENST00000409589 | ENSP00000386555 |
| | ENST00000424272 | ENSP00000415366 |
| | ENST00000409329 | ENSP00000387131 |
| | ENST00000428279 | ENSP00000410461 |
| | ENST00000410023 | ENSP00000386380 |
| JUNB | ENST00000302754 | ENSP00000303315 |
| KLF10 | ENST00000285407 | ENSP00000285407 |
| | ENST00000395884 | ENSP00000379222 |
| KLF4 | ENST00000497048 | Non-protein coding |
| | ENST00000493306 | Non-protein coding |
| | ENST00000374672 | ENSP00000363804 |
| LDLR | ENST00000252444 | ENSP00000252444 |
| | ENST00000560628 | Non-protein coding |
| LGALS3 | ENST00000254301 | ENSP00000254301 |
| | ENST00000556438 | Non-protein coding |
| LPAR1 | ENST00000358883 | ENSP00000351755 |
| | ENST00000541779 | ENSP00000445697 |
| | ENST00000374430 | ENSP00000363552 |
| | ENST00000374431 | ENSP00000363553 |
| MALAT1 | ENST00000534336 | Non-protein coding |
| MTUS1 | ENST00000517413 | Non-protein coding |
| | ENST00000381861 | ENSP00000371285 |
| | ENST00000520196 | Non-protein coding |
| | ENST00000381869 | ENSP00000371293 |
| | ENST00000262102 | ENSP00000262102 |
| | ENST00000400046 | ENSP00000382921 |
| | ENST00000544260 | ENSP00000445738 |
| | ENST00000297488 | ENSP00000297488 |
| MYBPC1 | ENST00000541119 | ENSP00000442847 |
| | ENST00000551300 | ENSP00000447116 |
| | ENST00000361466 | ENSP00000354849 |
| | ENST00000547509 | ENSP00000447362 |
| | ENST00000552198 | Non-protein coding |
| | ENST00000547405 | ENSP00000448175 |
| | ENST00000441232 | ENSP00000388989 |
| | ENST00000452455 | ENSP00000400908 |
| | ENST00000550270 | ENSP00000449702 |
| | ENST00000392934 | ENSP00000376665 |
| | ENST00000545503 | ENSP00000440034 |
| | ENST00000550514 | ENSP00000447404 |
| | ENST00000550501 | Non-protein coding |
| | ENST00000553190 | ENSP00000447900 |
| | ENST00000360610 | ENSP00000353822 |
| | ENST00000361685 | ENSP00000354845 |
| | ENST00000549145 | ENSP00000447660 |
| | ENST00000536007 | ENSP00000446128 |
| NFIL3 | ENST00000534336 | ENSP00000297689 |
| NR4A3 | ENST00000395097 | ENSP00000378531 |
| | ENST00000330847 | ENSP00000333122 |
| PI15 | ENST00000260113 | ENSP00000260113 |
| | ENST00000523773 | ENSP00000428567 |
| PTGS2 | ENST00000490885 | Non-protein coding |
| | ENST00000559627 | Non-protein coding |
| | ENST00000367468 | ENSP00000356438 |
| | ENST00000466691 | Non-protein coding |
| RHOBTB3 | ENST00000510313 | ENSP00000424844 |
| | ENST00000379982 | ENSP00000369318 |
| | ENST00000504179 | ENSP00000422360 |
| RIN2 | ENST00000484638 | Non-protein coding |
| | ENST00000255006 | ENSP00000255006 |
| RNFT2 | ENST00000319176 | ENSP00000321405 |
| | ENST00000547718 | Non-protein coding |
| | ENST00000551251 | Non-protein coding |
| | ENST00000407967 | ENSP00000385669 |
| | ENST00000392549 | ENSP00000376332 |
| | ENST00000257575 | ENSP00000257575 |
| SELE | ENST00000367777 | ENSP00000356751 |
| | ENST00000367775 | ENSP00000356749 |
| | ENST00000367781 | ENSP00000356755 |
| | ENST00000333360 | ENSP00000331736 |
| | ENST00000367776 | ENSP00000356750 |
| | ENST00000367779 | ENSP00000356753 |
| | ENST00000367780 | ENSP00000356754 |
| | ENST00000367782 | ENSP00000356756 |
| SLC15A2 | ENST00000469422 | Non-protein coding |
| | ENST00000295605 | ENSP00000295605 |
| | ENST00000489711 | ENSP00000417085 |
| SOCS2 | ENST00000549206 | ENSP00000448815 |
| | ENST00000549122 | ENSP00000447161 |
| | ENST00000548537 | ENSP00000448709 |
| | ENST00000551883 | ENSP00000474805 |
| | ENST00000340600 | ENSP00000339428 |
| SOCS3 | ENST00000330871 | ENSP00000330341 |
| SSTR1 | ENST00000267377 | ENSP00000267377 |
| ST6GAL1 | ENST00000470633 | Non-protein coding |
| | ENST00000457772 | ENSP00000412221 |
| | ENST00000169298 | ENSP00000169298 |
| | ENST00000448044 | ENSP00000389337 |
| TSC22D1 | ENST00000261489 | ENSP00000261489 |
| | ENST00000458659 | ENSP00000397435 |
| | ENST00000501704 | ENSP00000437414 |
| XBP1 | ENST00000216037 | ENSP00000216037 |
| | ENST00000405219 | ENSP00000384295 |
| | ENST00000344347 | ENSP00000343155 |
| | ENST00000403532 | ENSP00000385162 |
| | ENST00000482720 | Non-protein coding |
| ZFP36 | ENST00000594442 | ENSP00000471239 |
| | ENST00000248673 | ENSP00000248673 |
| | ENST00000597629 | ENSP00000469647 |
| F12 | ENST00000510358 | Non-protein coding |
| | ENST00000514943 | Non-protein coding |
| | ENST00000502854 | Non-protein coding |
| | ENST00000504406 | Non-protein coding |
| | ENST00000253496 | ENSP00000253496 |
| CD38 | ENST00000226279 | ENST00000226279 |
| | ENST00000502843 | Non-protein coding |
| F3 | ENST00000370207 | ENSP00000359226 |
| | ENST00000334047 | ENSP00000334145 |
| | ENST00000480356 | Non-protein coding |
| IL8 | ENST00000307407 | ENSP00000306512 |
| OAT | ENST00000471127 | Non-protein coding |
| | ENST00000368845 | ENSP00000357838 |
| | ENST00000539214 | ENSP00000439042 |
| FOXM1 | ENST00000342628 | ENSP00000342307 |
| | ENST00000536066 | Non-protein coding |
| | ENST00000361953 | ENSP00000354492 |
| | ENST00000359843 | ENSP00000352901 |

The methods described herein may further comprise extracting total nucleic acid or RNA from the sample. Suitable methods are known in the art and include use of commercially available kits such as Rneasy and GeneJET RNA purification kit.

In certain embodiments the methods may further comprise obtaining the sample from the subject. Typically the methods are in vitro methods performed on an isolated sample.

According to all aspects of the invention samples may be of any suitable form. The sample may comprise, consist essentially of or consist of prostate cells and often a prostate tissue sample. The prostate cells or tissue may comprise prostate cancer cells. In specific embodiments the sample comprises, consists essentially of or consists of a formalin-fixed paraffin-embedded biopsy sample. The tissue sample may be obtained by any suitable technique. Examples include a biopsy procedure, optionally a fine needle aspirate biopsy procedure. Body fluid samples may also be utilised. Suitable sample types include blood, to encompass whole blood, serum and plasma samples, urine and semen.

The methods of the invention may comprise selecting a treatment for prostate cancer in a subject and optionally performing the treatment. In certain embodiments if the characterisation of and/or prognosis for the prostate cancer is an increased likelihood of recurrence and/or metastasis and/or a poor prognosis the treatment selected is one or more of a) an anti-hormone treatment
b) a cytotoxic agent
c) a biologic
d) radiotherapy
e) targeted therapy
f) surgery By anti-hormone treatment (or hormone therapy) is meant a form of treatment which reduces the level and/or activity of selected hormones, in particular testosterone. The hormones may promote tumour growth and/or metastasis. The anti-hormone treatment may comprise a luteinizing hormone blocker, such as goserelin (also called Zoladex), buserelin, leuprorelin (also called Prostap), histrelin (Vantas) and triptorelin (also called Decapeptyl). The anti-hormone treatment may comprise a gonadotrophin release hormone (GnRH) blocker such as degarelix (Firmagon) or an anti-androgen such as flutamide (also called Drogenil) and bicalutamide (also called Casodex). In specific embodiments the anti-hormone treatment may be bicalutamide and/or abiraterone.

The cytotoxic agent may be a platinum based agent and/or a taxane. In specific embodiments the platinum based agent is selected from cisplatin, carboplatin and oxaliplatin. The taxane may be paclitaxel, cabazitaxel or docetaxel. The cytotoxic agent may also be a vinca alkaloid, such as vinorelbine or vinblastine. The cytotoxic agent may be a topoisomerase inhibitor such as etoposide or an anthracycline (antibiotic) such as doxorubicin. The cytotoxic agent may be an alkylating agent such as estramustine.

By biologic is meant a medicinal product that is created by a biological process. A biologic may be, for example, a vaccine, blood or blood component, cells, gene therapy, tissue, or a recombinant therapeutic protein. Optionally the biologic is an antibody and/or a vaccine. The biologic may be Sipuleucel-T.

In certain embodiments the radiotherapy is extended radiotherapy, preferably extended-field radiotherapy.

Surgery may comprise radical prostatectomy. By radical prostatectomy is meant removal of the entire prostate gland, the seminal vesicles and the vas deferens. In further embodiments surgery comprises tumour resection i.e. removal of all or part of the tumour.

By targeted therapy is meant treatment using targeted therapeutic agents which are directed towards a specific drug target for the treatment of prostate cancer. In specific embodiments this may mean inhibitors directed towards targets such as PARP, AKT, MET, VEGFR etc. PARP inhibitors are a group of pharmacological inhibitors of the enzyme poly ADP ribose polymerase (PARP). Several forms of cancer are more dependent on PARP than regular cells, making PARP an attractive target for cancer therapy. Examples (in clinical trials) include iniparib, olaparib, rucaparib, veliparib, CEP 9722, MK 4827, BMN-673 and 3-aminobenzamide. AKT, also known as Protein Kinase B (PKB), is a serine/threonine-specific protein kinase that plays a key role in multiple cellular processes such as glucose metabolism, apoptosis, cell proliferation, transcription and cell migration. AKT is associated with tumor cell survival, proliferation, and invasiveness. Examples of AKT inhibitors include VQD-002, Perifosine, Miltefosine and AZD5363. MET is a proto-oncogene that encodes hepatocyte growth factor receptor (HGFR). The hepatocyte growth factor receptor protein possesses tyrosine-kinase activity. Examples of kinase inhibitors for inhibition of MET include K252a, SU11274, PHA-66752, ARQ197, Foretinib, SGX523 and MP470. MET activity can also be blocked by inhibiting the interaction with HGF. Many suitable antagonists including truncated HGF, anti-HGF antibodies and uncleavable HGF are known. VEGF receptors are receptors for vascular endothelial growth factor (VEGF). Various inhibitors are known such as lenvatinib, motesanib, pazopanib and regorafenib.

The methods of the present invention can guide therapy selection as well as selecting patient groups for enrichment strategies during clinical trial evaluation of novel therapeutics. For example, when evaluating a putative anti-cancer agent or treatment regime, the methods disclosed herein may be used to select individuals for clinical trials that have prostate cancer characterized as having an increased likelihood of recurrence and/or metastasis and/or a poor prognosis.

The invention also relates to a system or device for performing a method as described herein.

In a further aspect, the present invention relates to a system or test kit for characterising and/or prognosing prostate cancer in a subject, comprising:

a) one or more testing devices for determining the expression level of at least one of FOXM1, TRPM3, PDRG1, SRSF5, PDE4D, F12, PDK4, ADAMTS1, ADAMTS9, B3GNT5, CD38, CEBPD, CENPF, CREM, DKK1, EMP1, ERRFI1, F3, HJURP, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, RNFT2, SELE, SLC15A2, SOCS2, SOCS3, SSTR1, ST6GAL1, TSC22D1, XBP1 and ZFP36 in a sample from the subject
b) a processor; and
c) storage medium comprising a computer application that, when executed by the processor, is configured to:
(i) access and/or calculate the determined expression levels of the at least one of
FOXM1, TRPM3, PDRG1, SRSF5, PDE4D, F12, PDK4, ADAMTS1, ADAMTS9, B3GNT5, CD38, CEBPD, CENPF, CREM, DKK1, EMP1, ERRFI1, F3, HJURP, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, RNFT2, SELE, SLC15A2, SOCS2, SOCS3, SSTR1, ST6GAL1, TSC22D1, XBP1 and ZFP36 in the sample on the one or more testing devices
(ii) calculate whether there is an increased or decreased level of the at least one of
FOXM1, TRPM3, PDRG1, SRSF5, PDE4D, F12, PDK4, ADAMTS1, ADAMTS9, B3GNT5, CD38, CEBPD, CENPF, CREM, DKK1, EMP1, ERRFI1, F3, HJURP, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, RNFT2, SELE, SLC15A2, SOCS2, SOCS3, SSTR1, ST6GAL1, TSC22D1, XBP1 and ZFP36 in the sample; and (iii) output from the processor the characteristaion of and/or prognosis for the prostate cancer.

By testing device is meant a combination of components that allows the expression level of a gene to be determined. The components may include any of those described above with respect to the methods for determining expression level at the level of protein, RNA or epigenetic modification. For example the components may be antibodies, primers, detection agents and so on. Components may also include one or more of the following: microscopes, microscope slides, x-ray film, radioactivity counters, scintillation counters, spectrophotometers, colorimeters, fluorometers, luminometers, and densitometers.

In certain embodiments the system or test kit further comprises a display for the output from the processor.

The invention also relates to a computer application or storage medium comprising a computer application as defined above.

In certain example embodiments, provided is a computer-implemented method, system, and a computer program product for characterising and/or prognosing prostate cancer in a subject, in accordance with the methods described herein. For example, the computer program product may comprise a non-transitory computer-readable storage device having computer-readable program instructions embodied thereon that, when executed by a computer, cause the computer to characterise and/or prognose prostate cancer in a subject as described herein. For example, the computer executable instructions may cause the computer to:

(i) access and/or calculate the determined expression levels of the at least one of FOXM1, TRPM3, PDRG1, SRSF5, PDE4D, F12, PDK4, ADAMTS1, ADAMTS9, B3GNT5, CD38, CEBPD, CENPF, CREM, DKK1, EMP1, ERRFI1, F3, HJURP, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, RNFT2, SELE, SLC15A2, SOCS2, SOCS3, SSTR1, ST6GAL1, TSC22D1, XBP1 and ZFP36 in a sample on one or more testing devices;

(ii) calculate whether there is an increased or decreased level of the at least one of FOXM1, TRPM3, PDRG1, SRSF5, PDE4D, F12, PDK4, ADAMTS1, ADAMTS9, B3GNT5, CD38, CEBPD, CENPF, CREM, DKK1, EMP1, ERRFI1, F3, HJURP, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, RNFT2, SELE, SLC15A2, SOCS2, SOCS3, SSTR1, ST6GAL1, TSC22D1, XBP1 and ZFP36 in the sample; and, (iii) provide an output regarding the characterization of and/or prognosis for the prostate cancer.

In certain example embodiments, the computer-implemented method, system, and computer program product may be embodied in a computer application, for example, that operates and executes on a computing machine and a module. When executed, the application may characterise and/or prognose prostate cancer in a subject, in accordance with the example embodiments described herein.

As used herein, the computing machine may correspond to any computers, servers, embedded systems, or computing systems. The module may comprise one or more hardware or software elements configured to facilitate the computing machine in performing the various methods and processing functions presented herein. The computing machine may include various internal or attached components such as a processor, system bus, system memory, storage media, input/output interface, and a network interface for communicating with a network, for example. The computing machine may be implemented as a conventional computer system, an embedded controller, a laptop, a server, a customized machine, any other hardware platform, such as a laboratory computer or device, for example, or any combination thereof. The computing machine may be a distributed system configured to function using multiple computing machines interconnected via a data network or bus system, for example.

The processor may be configured to execute code or instructions to perform the operations and functionality described herein, manage request flow and address mappings, and to perform calculations and generate commands. The processor may be configured to monitor and control the operation of the components in the computing machine. The processor may be a general purpose processor, a processor core, a multiprocessor, a reconfigurable processor, a microcontroller, a digital signal processor ("DSP"), an application specific integrated circuit ("ASIC"), a graphics processing unit ("GPU"), a field programmable gate array ("FPGA"), a programmable logic device ("PLD"), a controller, a state machine, gated logic, discrete hardware components, any other processing unit, or any combination or multiplicity thereof. The processor may be a single processing unit, multiple processing units, a single processing core, multiple processing cores, special purpose processing cores, co-processors, or any combination thereof. According to certain example embodiments, the processor, along with other components of the computing machine, may be a virtualized computing machine executing within one or more other computing machines.

The system memory may include non-volatile memories such as read-only memory ("ROM"), programmable read-only memory ("PROM"), erasable programmable read-only memory ("EPROM"), flash memory, or any other device capable of storing program instructions or data with or without applied power. The system memory may also include volatile memories such as random access memory ("RAM"), static random access memory ("SRAM"), dynamic random access memory ("DRAM"), and synchronous dynamic random access memory ("SDRAM"). Other types of RAM also may be used to implement the system memory. The system memory may be implemented using a single memory module or multiple memory modules. While the system memory may be part of the computing machine, one skilled in the art will recognize that the system memory may be separate from the computing machine without departing from the scope of the subject technology. It should also be appreciated that the system memory may include, or operate in conjunction with, a non-volatile storage device such as the storage media. The storage media may include a hard disk, a floppy disk, a compact disc read only memory ("CD-ROM"), a digital versatile disc ("DVD"), a Blu-ray disc, a magnetic tape, a flash memory, other non-volatile memory device, a solid sate drive ("SSD"), any magnetic storage device, any optical storage device, any electrical storage device, any semiconductor storage device, any physical-based storage device, any other data storage device, or any combination or multiplicity thereof. The storage media may store one or more operating systems, application programs and program modules such as module, data, or any other information. The storage media may be part of, or connected to, the computing machine. The storage media may also be part of one or more other computing machines that are in communication with the computing machine, such as servers, database servers, cloud storage, network attached storage, and so forth.

The module may comprise one or more hardware or software elements configured to facilitate the computing machine with performing the various methods and processing functions presented herein. The module may include one or more sequences of instructions stored as software or firmware in association with the system memory, the storage media, or both. The storage media may therefore represent examples of machine or computer readable media on which instructions or code may be stored for execution by the processor. Machine or computer readable media may generally refer to any medium or media used to provide instructions to the processor. Such machine or computer readable media associated with the module may comprise a computer software product. It should be appreciated that a computer software product comprising the module may also be associated with one or more processes or methods for delivering the module to the computing machine via a network, any signal-bearing medium, or any other communication or delivery technology. The module may also comprise hardware circuits or information for configuring hardware circuits such as microcode or configuration information for an FPGA or other PLD.

The input/output ("I/O") interface may be configured to couple to one or more external devices, to receive data from the one or more external devices, and to send data to the one or more external devices. Such external devices along with the various internal devices may also be known as peripheral devices. The I/O interface may include both electrical and physical connections for operably coupling the various peripheral devices to the computing machine or the processor. The I/O interface may be configured to communicate data, addresses, and control signals between the peripheral devices, the computing machine, or the processor. The I/O interface may be configured to implement any standard interface, such as small computer system interface ("SCSI"), serial-attached SCSI ("SAS"), fiber channel, peripheral component interconnect ("PCI"), PCI express (PCIe), serial bus, parallel bus, advanced technology attached ("ATA"), serial ATA ("SATA"), universal serial bus ("USB"), Thunderbolt, FireWire, various video buses, and the like. The I/O interface may be configured to implement only one interface or bus technology.

Alternatively, the I/O interface may be configured to implement multiple interfaces or bus technologies. The I/O interface may be configured as part of, all of, or to operate in conjunction with, the system bus. The I/O interface may include one or more buffers for buffering transmissions between one or more external devices, internal devices, the computing machine, or the processor.

The I/O interface may couple the computing machine to various input devices including mice, touch-screens, scanners, electronic digitizers, sensors, receivers, touchpads, trackballs, cameras, microphones, keyboards, any other pointing devices, or any combinations thereof. The I/O interface may couple the computing machine to various output devices including video displays, speakers, printers, projectors, tactile feedback devices, automation control, robotic components, actuators, motors, fans, solenoids, valves, pumps, transmitters, signal emitters, lights, and so forth.

The computing machine may operate in a networked environment using logical connections through the network interface to one or more other systems or computing machines across the network. The network may include wide area networks (WAN), local area networks (LAN), intranets, the Internet, wireless access networks, wired networks, mobile networks, telephone networks, optical networks, or combinations thereof. The network may be packet switched, circuit switched, of any topology, and may use any communication protocol. Communication links within the network may involve various digital or an analog communication media such as fiber optic cables, free-space optics, waveguides, electrical conductors, wireless links, antennas, radio-frequency communications, and so forth.

The processor may be connected to the other elements of the computing machine or the various peripherals discussed herein through the system bus. It should be appreciated that the system bus may be within the processor, outside the processor, or both. According to some embodiments, any of the processor, the other elements of the computing machine, or the various peripherals discussed herein may be integrated into a single device such as a system on chip ("SOC"), system on package ("SOP"), or ASIC device.

Embodiments may comprise a computer program that embodies the functions described and illustrated herein, wherein the computer program is implemented in a computer system that comprises instructions stored in a machine-readable medium and a processor that executes the instructions. However, it should be apparent that there could be many different ways of implementing embodiments in computer programming, and the embodiments should not be construed as limited to any one set of computer program instructions. Further, a skilled programmer would be able to write such a computer program to implement one or more of the disclosed embodiments described herein. Therefore, disclosure of a particular set of program code instructions is not considered necessary for an adequate understanding of how to make and use embodiments. Further, those skilled in the art will appreciate that one or more aspects of embodiments described herein may be performed by hardware, software, or a combination thereof, as may be embodied in one or more computing systems. Moreover, any reference to an act being performed by a computer should not be construed as being performed by a single computer as more than one computer may perform the act.

The example embodiments described herein can be used with computer hardware and software that perform the methods and processing functions described previously. The systems, methods, and procedures described herein can be embodied in a programmable computer, computer-executable software, or digital circuitry. The software can be stored on computer-readable media. For example, computer-readable media can include a floppy disk, RAM, ROM, hard disk, removable media, flash memory, memory stick, optical media, magneto-optical media, CD-ROM, etc. Digital circuitry can include integrated circuits, gate arrays, building block logic, field programmable gate arrays (FPGA), etc.

Reagents, tools, and/or instructions for performing the methods described herein can be provided in a kit. Such a kit can include reagents for collecting a tissue sample from a patient, such as by biopsy, and reagents for processing the tissue. The kit can also include one or more reagents for performing a expression level analysis, such as reagents for performing nucleic acid amplification, including RT-PCR and qPCR, NGS, northern blot, proteomic analysis, or immunohistochemistry to determine expression levels of biomarkers in a sample of a patient. For example, primers for performing RT-PCR, probes for performing northern blot analyses, and/or antibodies or aptamers, as discussed herein, for performing proteomic analysis such as Western blot, immunohistochemistry and ELISA analyses can be included in such kits. Appropriate buffers for the assays can also be included. Detection reagents required for any of these assays can also be included. The kits may be array or PCR based kits for example and may include additional reagents, such as a polymerase and/or dNTPs for example. The kits featured herein can also include an instruction sheet describing how to perform the assays for measuring expression levels.

The kit may include one or more primer pairs complementary to at least one of TRPM3, PDRG1, SRSF5, PDE4D, F12, PDK4, ADAMTS1, ADAMTS9, B3GNT5, CD38, CEBPD, CENPF, CREM, DKK1, EMP1, ERRFI1, F3, HJURP, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, RNFT2, SELE, SLC15A2, SOCS2, SOCS3, SSTR1, ST6GAL1, TSC22D1, XBP1 and ZFP36.

The kit may also include one or more primer pairs complementary to a reference gene, for example primers complementary to at least one of TPT1, RPS14 or RPL37A.

Such a kit can also include primer pairs complementary to at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45 or 46 of TRPM3, PDRG1, SRSF5, PDE4D, F12, PDK4, ADAMTS1, ADAMTS9, B3GNT5, CD38, CEBPD, CENPF, CREM, DKK1, EMP1, ERRFI1, F3, HJURP, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, RNFT2, SELF, SLC15A2, SOCS2, SOCS3, SSTR1, ST6GAL1, TSC22D1, XBP1 and ZFP36.

The kit may include one or more primer pairs complementary to at least one of TRPM3, PDRG1, F12, CENPF, HJURP, RNFT2, and SSTR1 and one or more primer pairs complementary to at least one of SRSF5, PDE4D, PDK4, ADAMTS1, ADAMTS9, B3GNT5, CD38, CEBPD, CREM, DKK1, EMP1, ERRFI1, F3, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, SELE, SLC15A2, SOCS2, SOCS3, ST6GAL1, TSC22D1, XBP1 and ZFP36.

Kits for characterising and/or prognosing prostate cancer in a subject may permit the methylation status of at least one of ADAMTS9, EMP1, F3, LDLR, LGALS3, MALAT1, MTUS1, NR4A3, PTGS2, RIN2, SLC15A2, SOCS3 and TSC22D1 to be determined. The determined methylation status, which may be hypermethylation, is used to provide a characterisation of and/or a prognosis for the prostate cancer. Such kits may include primers and/or probes for determining the methylation status of the gene or genes directly. They may thus comprise methylation specific primers and/or probes that discriminate between methylated and unmethylated forms of DNA by hybridization. Such kits will typically also contain a reagent that selectively modifies either the methylated or non-methylated form of CpG dinucleotide motifs. Suitable chemical reagents comprise hydrazine and bisulphite ions. An example is sodium bisulphite. The kits may, however, contain other reagents as discussed hereinabove to determine methylation status such as restriction endonucleases.

Accordingly, the invention also relates to a kit for characterising and/or prognosing prostate cancer in a subject comprising one or more antibodies or aptamers as described above.

As discussed above, in certain embodiments an increased expression level of at least one of TRPM3, PDRG1, F12, CENPF, HJURP, RNFT2, and SSTR1 or of FOXM1 indicates an increased likelihood of recurrence and/or metastasis and/or a poor prognosis. In further embodiments a decreased expression level of at least one of SRSF5, PDE4D, PDK4, ADAMTS1, ADAMTS9, B3GNT5, CD38, CEBPD, CREM, DKK1, EMP1, ERRFI1, F3, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, SELF, SLC15A2, SOCS2, SOCS3, ST6GAL1, TSC22D1, XBP1 and ZFP36 indicates an increased likelihood of recurrence and/or metastasis and/or a poor prognosis.

Accordingly, the kits described herein may comprise primers, probes or antibodies/aptamers (as discussed herein) for determining the expression level of at least one of TRPM3, PDRG1, F12, CENPF, HJURP, RNFT2, and SSTR1 or FOXM1 and at least one of SRSF5, PDE4D, PDK4, ADAMTS1, ADAMTS9, B3GNT5, CD38, CEBPD, CREM, DKK1, EMP1, ERRFI1, F3, IL1R1, IL8, JUNB, KLF10, KLF4, LDLR, LGALS3, LPAR1, MALAT1, MTUS1, MYBPC1, NFIL3, NR4A3, OAT, PI15, PTGS2, RHOBTB3, RIN2, SELE, SLC15A2, SOCS2, SOCS3, ST6GAL1, TSC22D1, XBP1 and ZFP36. Thus, the kits may incorporate reagents to determine expression levels of a combination of an up-regulated marker and a down-regulated marker. Suitable antibodies and/or primers/probes can be derived from Tables B, C and D herein.

Informational material included in the kits can be descriptive, instructional, marketing or other material that relates to the methods described herein and/or the use of the reagents for the methods described herein. For example, the informational material of the kit can contain contact information, e.g., a physical address, email address, website, or telephone number, where a user of the kit can obtain substantive information about performing a gene expression analysis and interpreting the results.

The kit may further comprise a computer application or storage medium as described above.

The example systems, methods, and acts described in the embodiments presented previously are illustrative, and, in alternative embodiments, certain acts can be performed in a different order, in parallel with one another, omitted entirely, and/or combined between different example embodiments, and/or certain additional acts can be performed, without departing from the scope and spirit of various embodiments. Accordingly, such alternative embodiments are included in the examples described herein.

Although specific embodiments have been described above in detail, the description is merely for purposes of illustration. It should be appreciated, therefore, that many aspects described above are not intended as required or essential elements unless explicitly stated otherwise.

Modifications of, and equivalent components or acts corresponding to, the disclosed aspects of the example embodiments, in addition to those described above, can be made by a person of ordinary skill in the art, having the benefit of the present disclosure, without departing from the spirit and scope of embodiments defined in the following claims, the scope of which is to be accorded the broadest interpretation so as to encompass such modifications and equivalent structures.

Unsupervised hierarchical clustering of a FFPE prostate cancer sample set comprising 70 primary prostate cancers, 20 primary cancers with concomitant metastatic disease, 11 metastatic disease and 25 normal prostate samples FFPE.

A. Using the most variable genes across the dataset identified a subset of primary tumours that cluster with metastatic disease application (chi squared $2.77\times10^{-10}$)

B. Semi-supervised hierarchical clustering using 1083 differentially expressed genes identified from the internal dataset of the dataset published by Taylor and colleagues identified a similar subcluster of primary tumours that cluster with metastatic disease application (chi squared $2.78\times10^{-6}$).

C. Kaplan-Meier analysis of the probability that patients would remain disease free following surgery if they were part of the metastatic biology group or not, hazard ratios were determined by log-rank test.

FIG. 2

A. Overlap of 83 overexpressed genes with FOXM1 CHIP-Seq hits from publications, hypergeometric test of overlap p-value $9.269\times10^{-5}$ B. Box plot of pearson correlation scores of 39 over-expressed targets which overlapped with FOXM1 CHIP-seq hits and remaining over-expressed targets. T-test (p-value<0.0001).

FIG. 3

A. Great (http://bejerano.stanford.edu/great/public/html/) functional analysis, molecular function of genomic regions in which the hypermethylated probes are located.

B. Venn diagram demonstrating overlap of under-expressed genes with CHIP-SEQ identified targets of EZH2 and H3K27me3, Hypergeometric test of overlap.

C. Venn diagram demonstrating overlap of under-expressed genes with hyper-methylated and H3K27me3 modifications.

FIG. 4

Venn diagram showing the overlap between the top 10,000 ranked probesets including those that are least correlated between the metastatic biology subgroup and non-metastatic biology subgroup ("Lists 1 & 2") and those that are highly correlated between the non-metastatic biology subgroup and benign groups ("List 3").

FIG. 5

GAP analysis of sample clusters identified in internal dataset.

FIG. 6

Functional analysis of 1182 unique genes differentially expressed genes using Toppfun (http://toppgene.cchmc.org/)

A. Significant molecular processes of under-expressed genes

B. Significant molecular processes of overexpressed genes.

FIG. 7

Study outline for screening potential IHC antibodies

EXAMPLES

The present invention will be further understood by reference to the following experimental examples.

Results

Figure 1A:
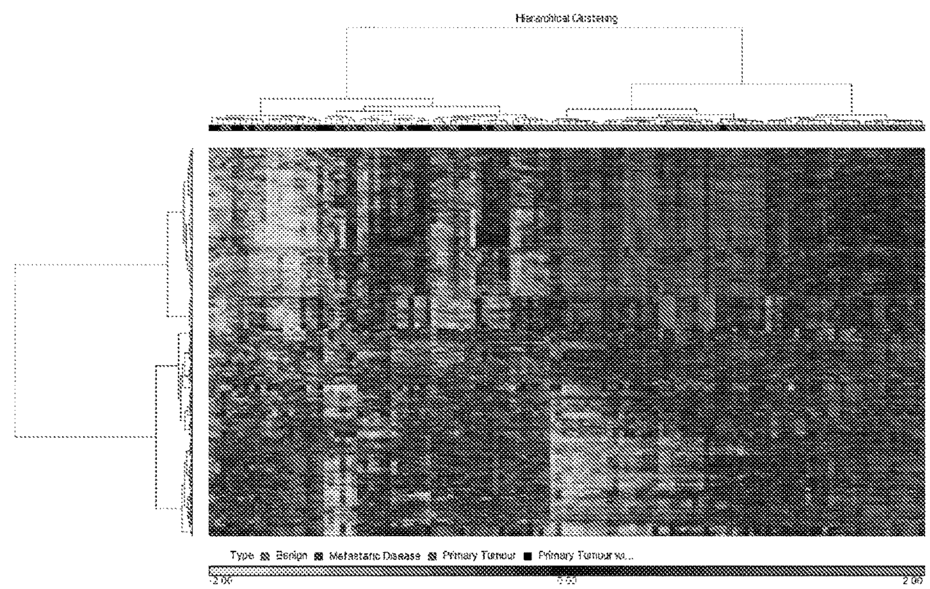
FIG. 1
Figure 5:
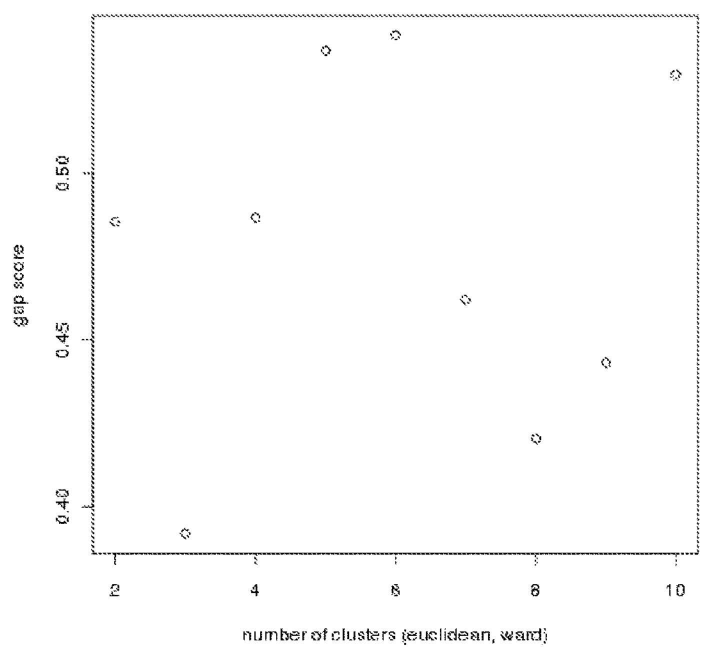

Unsupervised Hierarchical Clustering Identifies a Distinct Molecular Subgroup in Prostate Cancer Defined by Metastatic Biology We hypothesized that primary prostate cancers with metastatic potential would be transcriptionally similar to metastatic disease and primary disease with known concomitant metastases. In order to identify this metastatic subgroup we took an unsupervised hierarchical clustering approach using 70 resected primary prostate cancers clinically confined to prostate, 20 primary prostate cancer with known concomitant metastatic disease, 11 lymph nodes with metastatic disease, and 25 normal prostate samples. Clustering was performed using the most variable probe sets across the entire dataset. GAP statistical testing (Tibshirani et al 2001) identified 2 major sample clusters with statistical significance (FIG. 1A, FIG. 5).

One of these molecular subgroups had significant enrichment for metastatic disease and primary tumours with known concomitant metastases (chi squared $p=2.77\times10^{-10}$). Importantly, 29 primary prostate samples were also found in this group, which did not present with metastatic disease but shared a similar transcriptional biology. This group of tumours is hereon referred to as the "metastatic biology subgroup" and the second subgroup the "non-metastatic subgroup".

Next we performed gene expression analysis between primary tumours in the metastatic and non-metastatic subgroups and identified 1182 differentially expressed transcripts. The majority of these transcripts were under-expressed in the metastatic subgroup (1099 under-expressed versus 83 over-expressed).

Figure 1B:
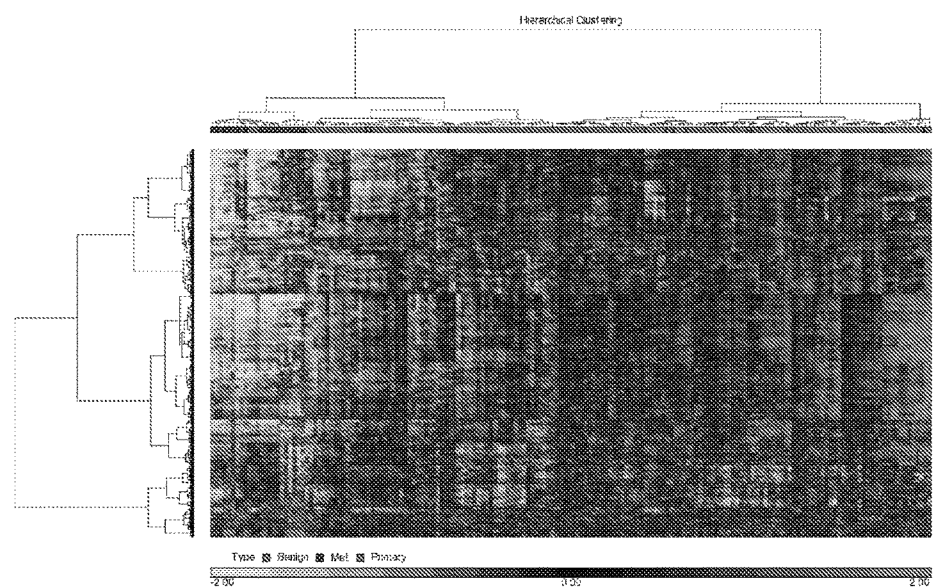
Figure 1C:
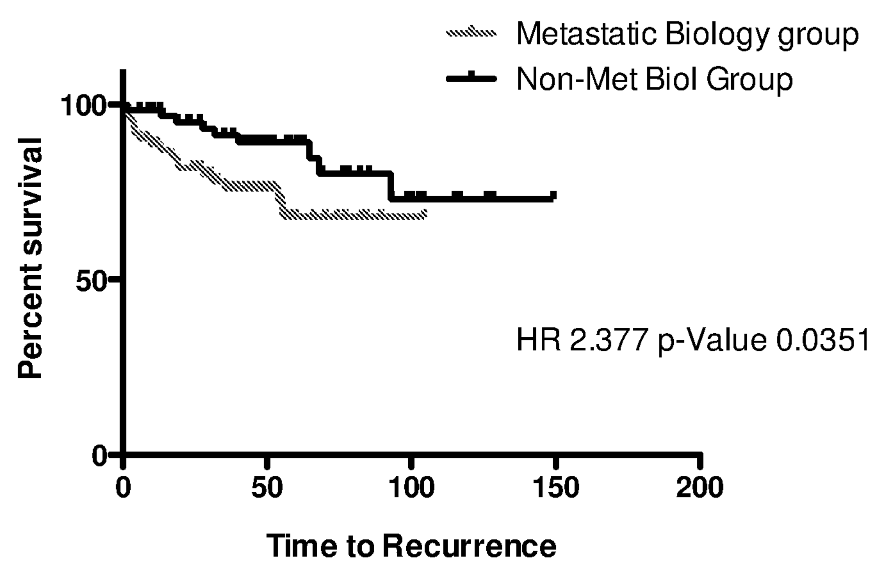

In order to identify if the 1182 differentially expressed genes were prognostic in a second dataset, we used the genes to cluster the prostate cancer dataset published by Taylor and colleagues (Taylor et al 2010), this dataset represents prostate cancers managed by surgery for which PSA follow-up is available. Consistent with our internal training set, we found 2 robust sample clusters, one of which demonstrated enrichment for metastatic samples (Chi squared $p=2.78\times10^{-6}$ (FIG. 1B). Importantly this group also contained 63 primary tumour samples without known metastatic disease at the time of presentation. Kaplan Meier analysis demonstrated that primary tumours within the metastatic biology group had a shorter time to disease recurrence (FIG. 1C) following surgery (Hazard Ratio (HR) 2.377 and p-value 0.0351). The clinical and pathological characteristics of the sample clusters are detailed in table 1. Importantly, there were no differences in other prognostic clinical factors such as stage, grade or PSA levels pre-treatment.

Molecular Pathways that Underlie the Metastatic Biology Group

To establish which molecular pathways give rise to the metastatic phenotype and poor prognosis, we performed pathway analysis using 1182 differentially expressed genes between the metastatic and non-metastatic subgroups. This identified 10 significant over-expressed pathways and 20 under-expressed pathways in the metastatic subgroup (Table 2i and 2ii). Interestingly the majority of pathways overexpressed in the metastatic subgroup were related to mitotic progression (Table 2i), whereas the molecular pathways that were under-expressed were involved in cell adhesion, morphology, ATF2 and p53 transcription.

To establish which of these molecular pathways were responsible for the poor prognosis we used the genes representing each pathway to cluster the Taylor dataset and a second dataset published by Sun and colleagues (Sun et al 2009). This later dataset represents primary prostate cancers managed with surgery with PSA follow-up. A Kaplan Meier analysis of time to recurrence was used for each of the observed clusters (Tables 2i and 2ii).

Figure 2A:
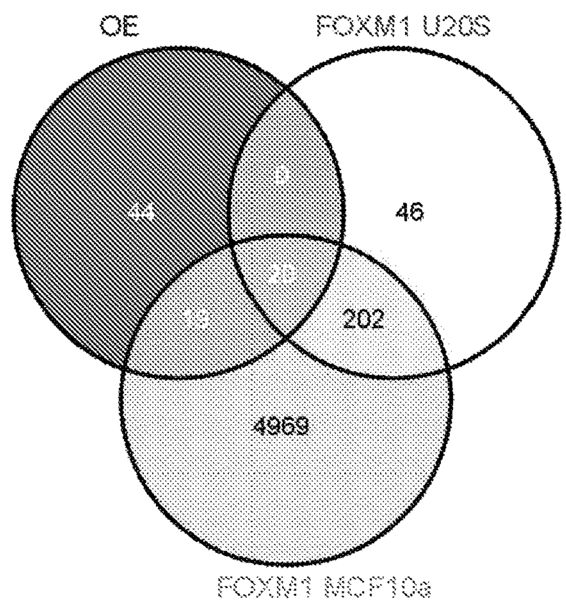
Figure 2B:
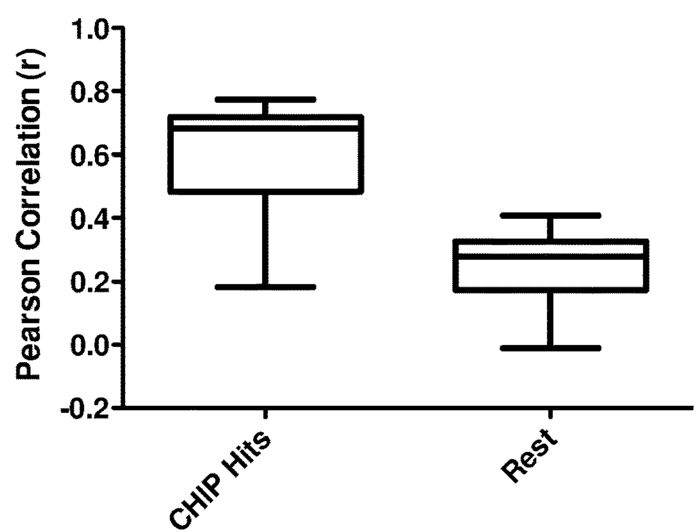

Of the overexpressed molecular pathways, only FOXM1 transcription factor network was significantly prognostic in the Taylor dataset (HR 2.755 p=0.0134). Furthermore FOXM1 itself was overexpressed in the metastatic biology subgroup in our internal training dataset (FC 2.13). To establish if increased FOXM1 was responsible for the over-expression of the mitotic genes in the metastatic biology group we interrogated 2 public FoxM1 CHIP-Seq data published by Sander and colleagues and Chen and colleagues (Chen et al 2013, Sanders et al 2013). We overlapped the identified FOXM1 CHIP-Seq targets with genes overexpressed in the metastatic biology group. Significantly, 39 out of 83 overexpressed genes in the metastatic subgroup were bound by FOXM1 in either of the datasets, with 20 being common to both. This overlap was highly significant ($9.269\times10\text{-}^{5}$). Furthermore we performed correlation analysis of all the overexpressed transcripts against FOXM1 levels in the internal dataset, (supplementary table 3). Comparison of the correlations of the 39 FOXM1 targets identified through the analysis of CHIP-Seq data to the non-CHIP targets demonstrated a highly significant increase in correlation scores for the FOXM1 targets versus those not bound by FOXM1 (t test p-value<0.0001) of the CHIP-Seq targets (FIG. 2B). Taken together this data strongly suggest that FoxM1 overexpression is responsible for the transcriptional activation of a large subset of the 83 genes that were detected as over-expressed in the metastatic subgroup.

Under-expressed molecular pathways that were significantly prognostic in both the Taylor and Sun datasets were muscle contraction, adipogenesis and ATF2 transcriptional targets. The diltiazem pathway was significantly prognostic in the Taylor dataset whereas integrin signaling and transcriptional targets for p53 although lost in the Taylor dataset, only reached prognostic significance in the Sun dataset.

Figure 6A:
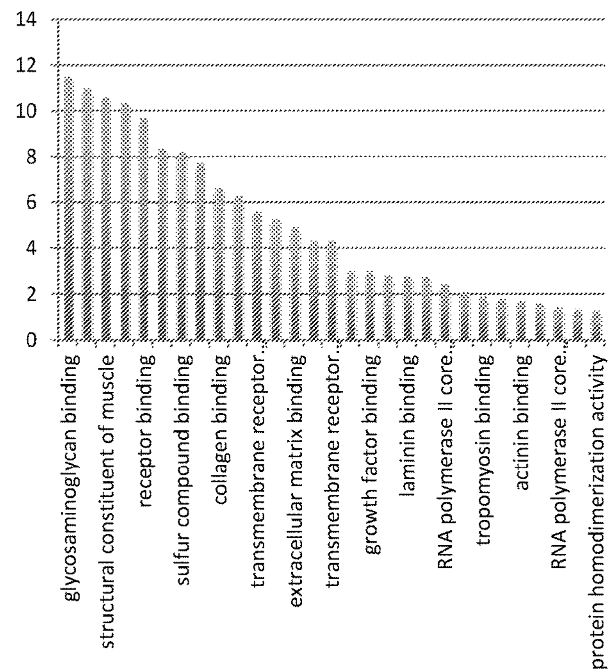
Figure 6B:
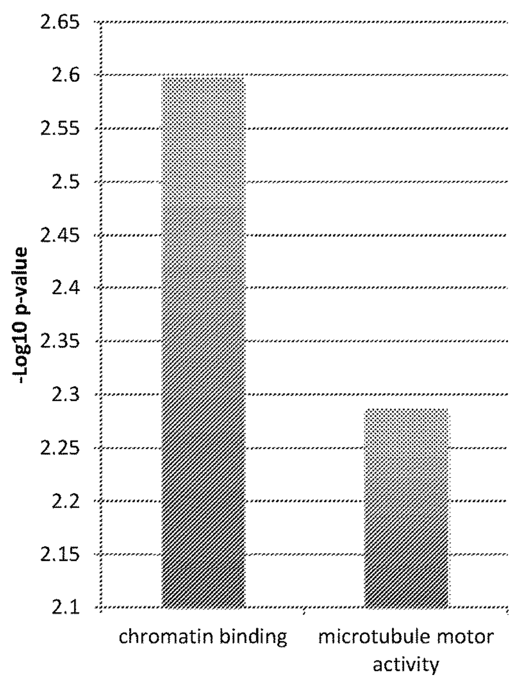

Epigenetic Silencing of Gene Expression Occurs in the Metastatic Biology Subgroup The majority of differentially expressed genes in the metastatic biology subgroup were down-regulated. Next we asked what potential mechanisms could account for this marked loss of gene expression in the metastatic biology group. Analysis of the molecular processes identified that genes involved in chromatin binding were over-expressed (FIG. 6), importantly we noted that several genes known to be involved in epigenetic gene regulation were up-regulated including AR, EZH2, HELLS and UHRF1) (Table 3).

UHRF1 was overexpressed in the metastatic biology subgroup (2.375 fold). This protein has recently been shown to contribute to and to maintain epigenetic silencing in prostate cancer (Babbio et al 2012). UHRF1 can bind to hemimethylated CpGs and can recruit DNMT1 to maintain DNA methylation patterns (Bostick et al 2007, Sharif et al 2007). Increased rates of DNA methylation at or near promoters has been shown to correlate to reduced gene expression, this is most probably related to accessibility of transcription factors to the gene promoters.

We therefore measured the DNA methylation levels in a subset of 22 tumours from our interim training set (11 from each subgroup) using a high content DNA methylation array (sample details in supplementary table 3). Global analysis of the 1098 under-expressed genes in the metastatic subgroup demonstrated that 418 had increased rates of DNA methylation (p-value of overlap $1.546\times10^{-34}$) (table 4). Furthermore, analysis of the over-expressed gene sets showed no significant hyper or hypo methylation status thereby suggesting that altered methylation status is not important in the over-expressed gene sets.

Figure 3A:
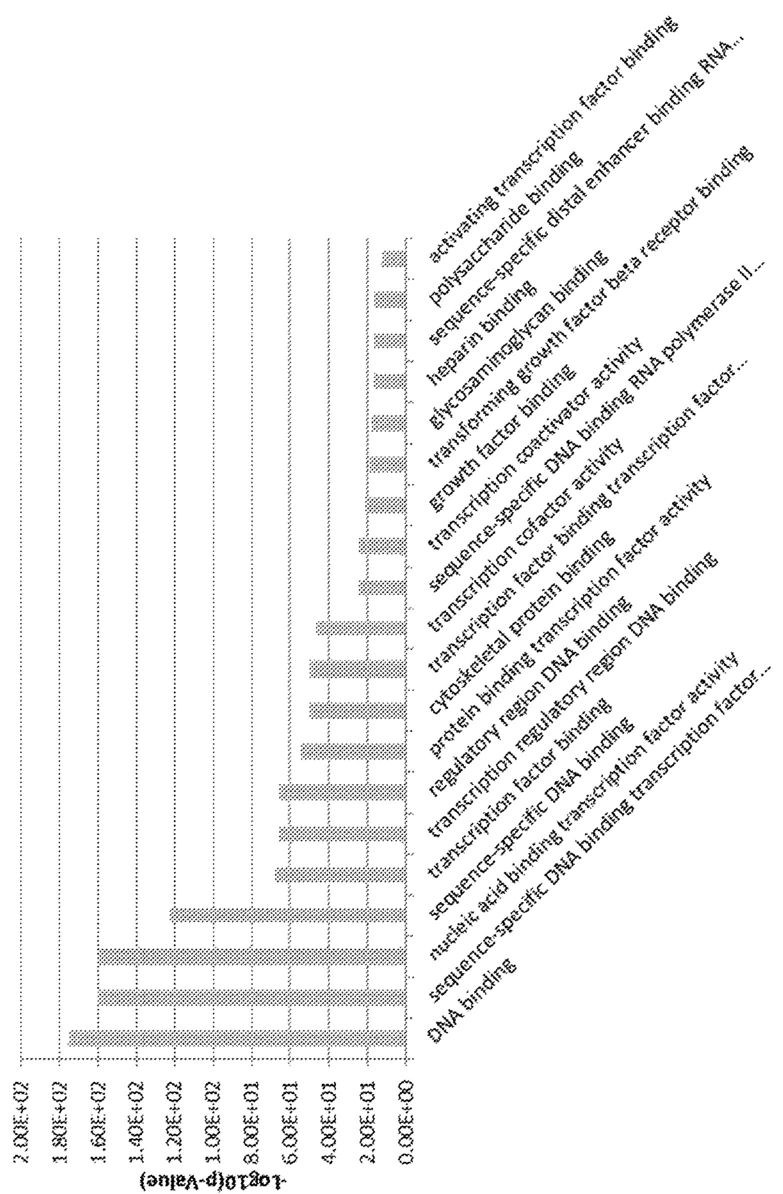

GREAT (http://bejerano.stanford.edu/great/public/html/) analysis of the hyper-methylated genomic regions demonstrated a number of enriched molecular processes (FIG. 3A), in particular DNA binding and transcription factor functions. This suggested that methylation not only silences genes directly in the metastatic biology group, but could be responsible for the loss of genes involved in transcription causing a further loss in gene expression.

Figure 3B:
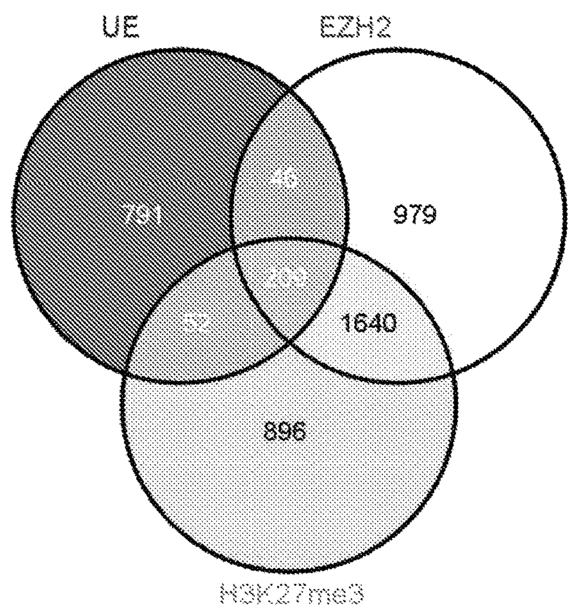

Another gene involved in epigenetic silencing, EZH2 was over 2 fold over-expressed in the metastatic biology group (Table 3). EZH2 is a component of the PRC2 (Polycomb Repressive Complex 2) one of the two classes of polycomb-group proteins or (PcG). This complex has histone methyltransferase activity and EZH2 is the catalytic subunit. Indeed, EZH2 expression is the key determinant of histone methyltransferase activity. The PRC2 complex trimethylates histone H3 on lysine 27 (i.e. H3K27me3), this site is a mark of transcriptionally silent chromatin. To establish if EZH2 function might account for at least part of the loss of gene expression in the metastatic subgroup, we used a public CHIP-Seq (Wu et al 2012) prostate cancer cell line dataset. Specifically we compared genes known to bind EZH2 and H3K27me3 to those that were suppressed in the metastatic biology subgroup (FIG. 3B). A significant number of the under-expressed genes were bound by EZH2, H3K27me3 or both (p-Value $2.597\times10^{-12}$), thereby strongly implicating chromatin silencing via EZH2 mediated histone modification as a key mechanism for silencing of a subset of the genes within the metastatic subgroup.

Figure 3C:
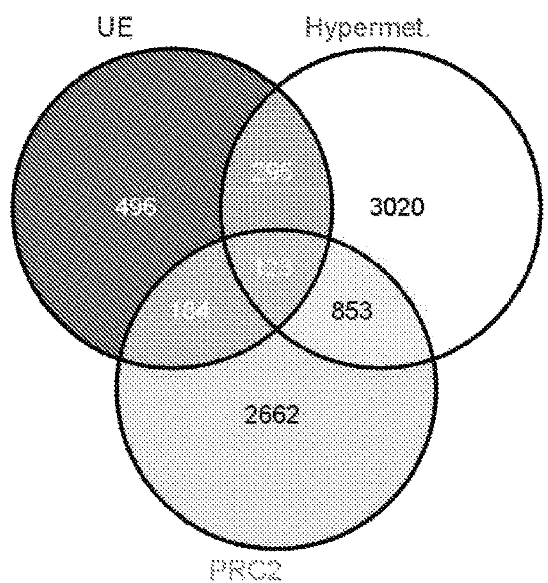

Interestingly, only a proportion of the targets of epigenetic silencing (123/602) had increased rates of hyper-methylation (FIG. 3C) and were predicted to have H3K27me3 related histone modification thereby suggesting that the two mechanisms may work largely independently to silence gene expression.

Methods for Detection of the Metastatic Biology Subgroup

Hierarchal clustering is a useful analysis method of gene expression data from a number of samples, however it cannot be used to prospectively classify individual tumours. Additionally, in a previous study we have demonstrated that tumour heterogeneity in prostate cancer causes significant discordance between tumour biopsy and resected tumour profiles from the same patient. Therefore we elected to develop markers suitable for immunohistochemistry (IHC) that would prospectively classify if a tumour were similar to the metastatic biology subgroup. To achieve this we employed 2 methods, firstly we identified transcripts that were differentially expressed between the metastatic biology subgroup and the non-metastatic biology subgroup but had little expression difference between the non-metastatic biology subgroup and normal. This process identified 393 probesets, using the 2-sample t-test method, ~75% of these probesets were overexpressed in the non-metastatic biology subgroup in comparison to the metastatic biology subgroup. We termed this approach the targeted as the normal prostate within the test case can be used as a reference.

For the second approach we assessed the 1182 differentially expressed between the metastatic biology subgroup non-metastatic subgroup, in this instance as there maybe expression differences between the non-metastatic biology group and benign/normal there is a requirement for a reference target, to identify suitable references we identified genes with minimal expression variance within all prostate cancer samples regardless of subgroup (the top 3 genes are summarised in table 7).

Prognostic Utility of IHC Targets

For the first approach the 393 probesets were mapped to a gene level to assist independent evaluation in an external dataset, Taylor et al 2010. In this dataset a total of 349 of the genes were detected. We performed multivariate analysis of these 349 genes in Taylor using time-to-biochemical recurrence with Cox proportional hazard corrected for Age, Grade and Stage, this resulted in 7 genes with significant multivariate prognostic function (p-value<0.05.), these were TRPM3, PDRG1, SRSF5, PDE4D, CNPY4, F12 and PDK4. (Table 5) Univariate survival analysis was also performed, in which 52 genes were significant with a p-value<0.05. There was an overlap of 3 genes in these top ranked probesets; these were SRSF5, PDE4D and PDK4. The 393 probesets were also assessed using an anova test to determine if they were significantly associated to clinical factors, namely Pathology Gleason score (and Gleason score 1 and 2).

For the second approach the 1182 differentially expressed genes tested in the same multivariate analysis, this identified 56 genes with significant multivariate prognostic function (p-value<0.05.), (Table 6). Univariate survival analysis was also performed, in which 304 unique genes were significant with a p-value<0.05. There was an overlap of 41 genes in these top ranked probesets. The numbers of targets with significant multivariate prognostic function was outside the scope of validation therefore we further refined the list by cross-referencing with the prognostic pathways (Table 2i and 2ii), the FOXM1 CHIP-Seq hits and selected literature review. The top 14 genes from the focused, pathway and literature comparisons are summarised in Table 7. FOXM1 itself and the differentially expressed FOXM1 CHIP-Seq targets which demonstrated significant multivariate prognostic power are summarized in Table 9

Discussion

Since the majority of men who develop early prostate cancer will not die from the disease, there is a clear requirement to better understand the biology underlying metastatic spread. This may allow appropriate selection of high-risk patients for more aggressive primary therapies and spare low risk patients unnecessary side effects.

In this study we have identified a group of primary prostate cancers that are similar to metastatic disease at a molecular level. These tumours are defined by loss of expression of several genes and defined pathways; furthermore this group is defined by activation of the proto-oncogene FOXM1 that leads to increased expression of genes involved in mitosis.

We have define a series of markers which have multivariate prognostic power and are highly suitable for IHC development to prospectively assess if a tumour is at increased likelihood of recurrence and metastatic development.

TABLE 1

| | Metastatic Biology Group | Others | p-value |
|---|---|---|---|
| Mean Gleason Score | 6.952 | 6.714 | 0.0730 |
| Mean Stage | 2.429 | 2.381 | 0.648 |
| Mean PSA | 9.677 | 7.788 | 0.1984 |
| Patient age | 57.9 | 57.7 | 0.8633 |
| Time to relapse | 40.29 | 56.95 | 0.0014** |

Clinical and pathological criteria of the metastatic biology tumours and non-metastatic biology group in the Taylor dataset.

TABLE 2i

| Pathway | Pathway p-Value | Taylor HR | Taylor p-Value | Sun HR | Sun p-Value |
|---|---|---|---|---|---|
| Genes involved in Cell Cycle, Mitotic | 1.78E−10 | 2.118 | 0.0614 | 2.061 | 0.0602 |
| PLK1 signalling events | 4.42E−07 | 1.843 | 0.1306 | 1.54 | 0.2774 |
| Genes involved in Mitotic M-M/G1 phases | 1.10E−06 | 1.988 | 0.0997 | 0.841 | 0.6823 |
| Genes involved in Mitotic Prometaphase | 3.92E−06 | 2.062280883 | 0.0779 | 0.9289 | 0.8284 |
| Aurora B signalling | 8.51E−06 | 1.823 | 0.1352 | 1.031 | 0.9268 |
| FOXM1 transcription factor network | 4.19E−04 | 2.755 | 0.0134 | 1.737 | 0.1064 |
| Genes involved in Cyclin A1 associated events during G2/M transition | 1.21E−02 | 1.871 | 0.1274 | 0.7773 | 0.4777 |
| Genes involved in Phosphorylation of the APC/C | 1.79E−02 | 1.995 | 0.0922 | 0.9521 | 0.8838 |
| Cell cycle | 3.35E−02 | 1.837 | 0.1397 | 0.8063 | 0.5324 |
| Genes involved in E2F transcriptional targets at G1/S | 3.98E−02 | 0.462 | 0.0699 | 0.4214 | 0.07 |

Significant over-expressed pathways as detected using Toppfun, pathway p-value noted, Kaplan meier survival analysis results using pathways to cluster and define class labels i Taylor and Sun datasets.

TABLE 2ii

| Pathway | Pathway p-Value | Taylor HR | Taylor p-Value | Sun HR | Sun p-Value |
|---|---|---|---|---|---|
| Genes involved in Muscle contraction | 2.26E−10 | 2.495 | 0.0339 | 2.361 | 0.0196 |
| Genes involved in Smooth Muscle Contraction | 1.61E−07 | 2.155 | 0.0648 | 2.808 | 0.0094 |
| Adipogenesis | 4.05E−07 | 2.378 | 0.0391 | 2.336 | 0.0117 |
| Focal Adhesion | 4.79E−07 | 1.726 | 0.1814 | 1.01 | 0.9807 |
| Striated Muscle Contraction | 4.08E−06 | 2.6001 | 0.0189 | 2.24 | 0.0163 |
| Genes involved in Haemostasis | 1.14E−04 | 1.1 | 0.8235 | 1.322 | 0.4404 |
| Diltiazem Pathway | 5.21E−04 | 2.289 | 0.0431 | 1.568 | 0.1993 |
| Plasma membrane estrogen receptor signalling | 6.24E−04 | 2.179 | 0.0914 | 1.384 | 0.3411 |
| Genes involved in Formation of Platelet plug | 7.81E−04 | 1.872 | 0.1226 | 1.19 | 0.6283 |
| Genes involved in Platelet degranulation | 9.60E−04 | 1.129 | 0.769 | 1.502 | 0.2263 |
| Myometrial Relaxation and Contraction Pathways | 1.04E−03 | 2.611 | 0.0188 | 2.06 | 0.0342 |
| Integrins in angiogenesis | 1.74E−03 | 1.639 | 0.2234 | 0.8937 | 0.7829 |
| ATF-2 transcription factor network | 1.74E−03 | 4.006 | 0.0037 | 4.026 | 0.0004 |
| Genes involved in Platelet Activation | 1.75E−03 | 2.047 | 0.0788 | 1.347 | 0.422 |
| Syndecan-4-mediated signaling events | 2.61E−03 | 3.686 | 0.0105 | 1.667 | 0.1268 |

TABLE 2ii-continued

| Pathway | Pathway p-Value | Taylor HR | Taylor p-Value | Sun HR | Sun p-Value |
|---|---|---|---|---|---|
| LPA receptor mediated events | 5.01E−03 | 2.158 | 0.149 | 1.332 | 0.3791 |
| Integrin Signalling Pathway | 1.41E−02 | 1.893 | 0.1202 | 2.069 | 0.0306 |
| Genes involved in Integrin cell surface interactions | 2.44E−02 | 1.584 | 0.2567 | 1.549 | 0.1905 |
| Direct p53 effectors | 2.53E−02 | 2.151 | 0.0676 | 3.836 | 0.0003 |
| Integrin-mediated cell adhesion | 3.78E−02 | 1.941 | 0.1084 | 0.765 | 0.4997 |

Significant under-expressed pathways as detected using Toppfun, pathway p-value noted, Kaplan meier survival analysis results using pathways to cluster and define class labels i Taylor and Sun datasets.

TABLE 3

| | Fold Change | FDR corrected p-value | Role in transcriptional repression |
|---|---|---|---|
| AR | 2.41796 | 4.86E−10 | Yes |
| CENPA | 2.87805 | 3.23E−09 | Na |
| CENPF | 3.00853 | 4.19E−09 | Na |
| DLX1 | 3.22068 | 8.49E−08 | Na |
| EZH2 | 2.7026 | 2.45E−12 | Yes |
| HELLS | 2.10418 | 6.92E−05 | Yes |
| TOP2A | 2.90041 | 3.84E−09 | Na |
| UBE2T | 2.36638 | 3.65E−07 | Na |
| UHRF1 | 2.37542 | 2.32E−09 | Yes |
| ZIC2 | 2.08528 | 6.52E−05 | Yes |

Genes annotated as chromatin binding, fold change expression of metastatic biology group versus non and FDR corrected p-Value. Published role in transcriptional repression is noted.

TABLE 4

| Genes Set Name | Genes Hyper-methylated | Hypergeometric test p-value |
|---|---|---|
| Under-expressed genes | 418/1098 | $1.546 \times 10^{-34}$ |
| Over-expressed genes | 13/83 | 0.947 |

Over or under-expressed genes with increased hypermethylation in the metastatic biology group, Hypergeometric test to test significance of overlap.

TABLE 5

| | Multivariate | | Univariate | | Independence (pvals) | | | |
|---|---|---|---|---|---|---|---|---|
| | | | | | Path | Path | Path | |
| Gene | HR | pval | HR | pval | GGS | GG1 | GG2 | Expression |
| TRPM3 | 6.64 | 0.01 | 5.763 | 0.055 | 0.02 | 0.437 | 0.677 | Over-expressed |
| PDRG1 | 4.8835 | 0.027 | 2.416 | 0.256 | 0.046 | 0.035 | 0.351 | Over-expressed |
| SRSF5 | 0.378 | 0.029 | 0.398 | 0.031 | 0.11 | 0.382 | 0.165 | Under-expressed |
| PDE4D | 0.425 | 0.035 | 0.268 | 0 | 0 | 0.004 | 0 | Under-expressed |
| F12 | 5.523 | 0.042 | 2.789 | 0.263 | 0.895 | 0.845 | 0.844 | Over-expressed |
| PDK4 | 0.641 | 0.048 | 0.52 | 0.001 | 0.009 | 0.069 | 0.018 | Under-expressed |

Top ranked prognostic markers based upon multivariate survival analysis in Taylor dataset.

TABLE 6

| | Multivariate | | Univariate | | Expression in |
|---|---|---|---|---|---|
| | HR | pval | HR | pval | Metastatic biol. Group |
| ADAMTS1 | 0.553383 | 0.0348589 | 0.54021 | 0.0194342 | Under-expressed |
| ADAMTS9 | 0.4585803 | 0.0288481 | 0.371399 | 0.00848 | Under-expressed |
| B3GNT5 | 0.5137102 | 0.0299695 | 0.3956727 | 0.0017219 | Under-expressed |
| CD38 | 0.6091854 | 0.0138355 | 0.5143886 | 0.0004166 | Under-expressed |
| CEBPD | 0.3271493 | 0.0097009 | 0.1813086 | 8.15E−06 | Under-expressed |
| CENPF | 3.5933385 | 0.0416512 | 9.1943228 | 0.0001128 | Over-expressed |
| CREM | 0.2330916 | 0.0448842 | 0.1947922 | 0.01595 | Under-expressed |
| DKK1 | 0.2871025 | 0.0482413 | 0.3428314 | 0.0473753 | Under-expressed |
| EMP1 | 0.4347836 | 0.0071015 | 0.3768645 | 0.0006745 | Under-expressed |
| ERRFI1 | 0.5542049 | 0.0300146 | 0.5263541 | 0.0078253 | Under-expressed |
| F3 | 0.579862 | 0.0170842 | 0.6133141 | 0.0418215 | Under-expressed |
| HJURP | 13.578677 | 0.0428399 | 46.05557 | 0.002649 | Over-expressed |
| IL1R1 | 0.4800943 | 0.0108723 | 0.3570689 | 0.0002425 | Under-expressed |
| IL8 | 0.3158031 | 0.0348507 | 0.47006 | 0.0724264 | Under-expressed |
| JUNB | 0.5484282 | 0.0347493 | 0.4460346 | 0.0008361 | Under-expressed |
| KLF10 | 0.5017168 | 0.030925 | 0.4394025 | 0.0066195 | Under-expressed |
| KLF4 | 0.3979693 | 0.0274113 | 0.2711992 | 0.000817 | Under-expressed |
| LDLR | 0.4540006 | 0.0299326 | 0.2845191 | 0.0001791 | Under-expressed |
| LGALS3 | 0.2425137 | 0.0163003 | 0.1363453 | 0.0005586 | Under-expressed |
| LPAR1 | 0.4085325 | 0.0398731 | 0.2924915 | 0.0043957 | Under-expressed |
| MALAT1 | 0.1444922 | 0.0264399 | 0.2732161 | 0.1174596 | Under-expressed |
| MTUS1 | 0.4461261 | 0.0438701 | 0.293677 | 0.0001736 | Under-expressed |
| MYBPC1 | 0.5829982 | 0.002379 | 0.5657745 | 0.0003248 | Under-expressed |
| NFIL3 | 0.494893 | 0.0271456 | 0.3853505 | 0.0006228 | Under-expressed |
| NR4A3 | 0.3498147 | 0.0058837 | 0.3287529 | 0.0013712 | Under-expressed |
| OAT | 0.6455529 | 0.0451212 | 0.6272926 | 0.0531972 | Under-expressed |
| PDE4D | 0.4404056 | 0.0389414 | 0.2744262 | 0.0004312 | Under-expressed |
| PDK4 | 0.6173687 | 0.0302305 | 0.5004434 | 0.0008031 | Under-expressed |
| PI15 | 0.609224 | 0.0068663 | 0.4940706 | 7.96E−06 | Under-expressed |

TABLE 6-continued

| | Multivariate | | Univariate | | Expression in |
|---|---|---|---|---|---|
| | HR | pval | HR | pval | Metastatic biol. Group |
| PTGS2 | 0.5919948 | 0.0206793 | 0.5621402 | 0.0077942 | Under-expressed |
| RHOBTB3 | 0.5457431 | 0.0455287 | 0.4498483 | 0.0117462 | Under-expressed |
| RIN2 | 0.4232609 | 0.0422486 | 0.3777279 | 0.0290502 | Under-expressed |
| RNFT2 | 38.724825 | 0.0168421 | 52.633909 | 0.0070457 | Over-expressed |
| SELE | 0.4784527 | 0.0139667 | 0.4724994 | 0.0036146 | Under-expressed |
| SLC15A2 | 0.5968128 | 0.03609 | 0.4424453 | 0.0005391 | Under-expressed |
| SOCS2 | 0.2955096 | 0.003396 | 0.2391982 | 0.0005038 | Under-expressed |
| SOCS3 | 0.4423332 | 0.042005 | 0.3155164 | 0.0014183 | Under-expressed |
| SSTR1 | 9.0410923 | 0.0182887 | 15.147803 | 0.0033901 | Over-expressed |
| ST6GAL1 | 0.6042365 | 0.0088117 | 0.5305465 | 0.0016829 | Under-expressed |
| TSC22D1 | 0.452536 | 0.0301503 | 0.3209002 | 0.0011309 | Under-expressed |
| XBP1 | 0.2271852 | 0.0008373 | 0.2747813 | 0.0006004 | Under-expressed |
| ZFP36 | 0.517509 | 0.0108194 | 0.4385203 | 0.0001823 | Under-expressed |

Top ranked prognostic markers based upon multivariate survival analysis in Taylor dataset of differentially expressed genes between metastatic biology subgroup and non-metastatic biology subgroup.

TABLE 7

| Gene | Multivariate HR | pval | Univariate HR | pval | Source | Expression in Metastatic biology Group |
|---|---|---|---|---|---|---|
| TRPM3 | 6.6406 | 0.0105 | 5.7636 | 0.0551 | Targeted | Over-expressed |
| PDRG1 | 4.8835 | 0.0272 | 2.416 | 0.2566 | Targeted | Over-expressed |
| SRSF5 | 0.3787 | 0.0294 | 0.3986 | 0.031 | Targeted | Under-expressed |
| PDE4D | 0.4255 | 0.035 | 0.2685 | 0.0005 | Targeted | Under-expressed |
| PDK4 | 0.6415 | 0.0484 | 0.52 | 0.0019 | Targeted | Under-expressed |
| F12 | 5.5235 | 0.0428 | 2.7897 | 0.2638 | Targeted | Over-expressed |
| F3 | 0.591462629 | 0.026150109 | 0.641392413 | 0.070885567 | Pathway | Under-expressed |
| HJURP | 17.72622995 | 0.028647576 | 58.21478537 | 0.001862129 | Pathway | Over-expressed |
| CENPF | 4.009668447 | 0.028698111 | 9.892737548 | 8.66E−05 | Pathway | Over-expressed |
| MYBPC1 | 0.616919233 | 0.009107673 | 0.596731068 | 0.001740583 | Pathway | Under-expressed |
| SELE | 0.506452771 | 0.023940071 | 0.494071466 | 0.006723235 | Pathway | Under-expressed |
| CEBPD | 0.33366283 | 0.012163084 | 0.188671187 | 1.76E−05 | Pathway | Under-expressed |
| XBP1 | 0.227185248 | 0.000837328 | 0.274781347 | 0.000600431 | Literature | Under-expressed |
| TPT1 | NA | NA | NA | NA | Reference | NA |
| RPS14 | NA | NA | NA | NA | Reference | NA |
| RPL37A | NA | NA | NA | NA | Reference | NA |

Summarised IHC targets with reference genes.

TABLE 8

| | Expression in Metastatic biology Group | Hypermethylated |
|---|---|---|
| ADAMTS9 | Under-expressed | Hypermethylated |
| EMP1 | Under-expressed | Hypermethylated |
| F3 | Under-expressed | Hypermethylated |
| LDLR | Under-expressed | Hypermethylated |
| LGALS3 | Under-expressed | Hypermethylated |
| MALAT1 | Under-expressed | Hypermethylated |
| MTUS1 | Under-expressed | Hypermethylated |
| NR4A3 | Under-expressed | Hypermethylated |
| PTGS2 | Under-expressed | Hypermethylated |
| RIN2 | Under-expressed | Hypermethylated |
| SLC15A2 | Under-expressed | Hypermethylated |
| SOCS3 | Under-expressed | Hypermethylated |
| TSC22D1 | Under-expressed | Hypermethylated |

Top underexpressed markers that have increased hypermethylation levels.

of abs(FC) >2 and a significance p-value threshold adjusted for False Discovery Rate (FDR) (p-valueFDR<0.05).

TABLE 9

| | Multivariate | | Univariate | | Expression in |
|---|---|---|---|---|---|
| Gene | HR | pval | HR | pval | Metastatic Biology Group |
| FOXM1 | 3.635351021 | 0.158344619 | 9.446320585 | 0.011658425 | Over-expressed |
| CENPF | 3.593338484 | 0.041651166 | 9.194322768 | 0.000112762 | Over-expressed |
| HJURP | 13.57867693 | 0.042839901 | 46.05557007 | 0.002649046 | Over-expressed |
| RNFT2 | 38.72482502 | 0.016842083 | 52.63390875 | 0.007045687 | Over-expressed |
| XBP1 | 0.227185248 | 0.000837328 | 0.274781347 | 0.000600431 | Under-expressed |
| SOCS2 | 0.295509606 | 0.003395953 | 0.239198163 | 0.000503779 | Under-expressed |
| NR4A3 | 0.349814683 | 0.005883674 | 0.328752943 | 0.001371206 | Under-expressed |
| EMP1 | 0.434783557 | 0.00710147 | 0.37686453 | 0.000674458 | Under-expressed |
| ZFP36 | 0.517509016 | 0.010819386 | 0.438520253 | 0.000182313 | Under-expressed |
| IL1R1 | 0.480094331 | 0.010872279 | 0.357068877 | 0.000242495 | Under-expressed |
| SELE | 0.478452726 | 0.013966748 | 0.47249936 | 0.00361461 | Under-expressed |
| LGALS3 | 0.242513744 | 0.016300257 | 0.136345309 | 0.000558637 | Under-expressed |
| MALAT1 | 0.144492202 | 0.026439902 | 0.273216094 | 0.117459635 | Under-expressed |
| NFIL3 | 0.494893003 | 0.027145595 | 0.385350474 | 0.000622818 | Under-expressed |
| LDLR | 0.454000647 | 0.029932634 | 0.28451914 | 0.000179138 | Under-expressed |
| ERRFI1 | 0.554204851 | 0.030014585 | 0.52635411 | 0.007825297 | Under-expressed |
| KLF10 | 0.501716831 | 0.030925035 | 0.439402487 | 0.006619467 | Under-expressed |
| JUNB | 0.548428187 | 0.034749258 | 0.446034558 | 0.000836112 | Under-expressed |
| MTUS1 | 0.446126088 | 0.043870083 | 0.293677025 | 0.000173624 | Under-expressed |
| CREM | 0.233091594 | 0.044884166 | 0.194792247 | 0.01595 | Under-expressed |
| RHOBTB3 | 0.545743073 | 0.04552871 | 0.449848327 | 0.011746242 | Under-expressed |
| DKK1 | 0.287102503 | 0.048241265 | 0.34283137 | 0.047375265 | Under-expressed |

FOXM1 and FOXM1 CHIP-Seq targets which were differentially expressed in the metastatic biology group.

Methods

Patient Samples 126 samples (70 resected primary prostate cancers clinically confined to prostate, 20 primary prostate cancer with known concomitant metastatic disease, 11 lymph nodes with metastatic disease, and 25 normal prostate) were provided by Addenbrookes Hospital and Karolinska Institute following local ethical approval.

The subgroup and the prognostic significance were validated and tested in dataset published by Taylor et al which contained 179 samples (131 primary tumours, 29 normal and 19 metastatic disease. Time to biochemical recurrence and recurrence status following surgery were used to test prognostic significance, 5 samples were excluded from the analysis because of (surgery type PCA0056, and neo-adjuvant treatment, PCA0050, PCA0103, PCA119 and PCA0176).

Sun et al (79 tumour samples), samples were following surgery, 79 cases, 39 of which were classified as having disease recurrence.

Gene Expression Profiling.

Total RNA was extracted from macrodissected FFPE tumor samples using the Roche High Pure RNA Paraffin Kit (Roche Diagnostics Ltd.) as described previously (Kennedy R D, Bylesjo M, Kerr P et al. Development and independent validation of a prognostic assay for stage II colon cancer using formalin-fixed paraffin-embedded tissue. J Clin Oncol 2011; 29: 4620-4626). Total RNA was amplified using the NuGEN WT-Ovation™ FFPE System (NuGEN) and hybridized to the Almac Prostate Cancer DSA™ (Affymetrix) as described previously.

Statistical Analysis Methods

A one-way ANOVA analysis identified differentially expressed probesets between 29 primary metastatic biology group tumours and 41 primarynon-metastatic biology tumours group controls using a fold-change (FC) threshold of abs(FC) >2 and a significance p-value threshold adjusted for False Discovery Rate (FDR) (p-valueFDR<0.05).

Unique genes were determined as those in the sense orientation with at least 6 probes aligned.

A combined background & variance filter was applied to the data matrix to identify the most variable genes using an in-house developed feature selection program. Firstly, a background filter was applied to remove genes with expression values too low to be distinguished from the background noise. A high threshold was used to remove a large number of probesets and ensure these probesets are highly expressed (Threshold: $<=10^{-16}$). Secondly, an intensity dependent variance filter was applied to the data matrix to remove probesets with low variance across all samples (Threshold: $<=5.10^{-16}$). Feature selection resulted in 1651 most variable probesets.

Hierarchical clustering (Pearson correlation distance and Ward's linkage) was applied to probesets and samples from each dataset separately. The number of sub-clusters was determined using the gap statistic.

IHC Target Identification

The IHC targets of interest are those that are least correlated between the metastatic and non-metastatic groups (Lists 1 & 2) and those that are highly correlated between the non-metastatic and benign groups (List 3).

Correlation p-values for probesets in each of the three lists were ranked according to these criteria. The range of p-values observed in the top 10,000 ranked probesets in each list ranged from [0-6.62e-05] for List 1, [1.03e-19-6.17e-04] for List 2 and [0.99-0.82] for List 3.

Figure 4:
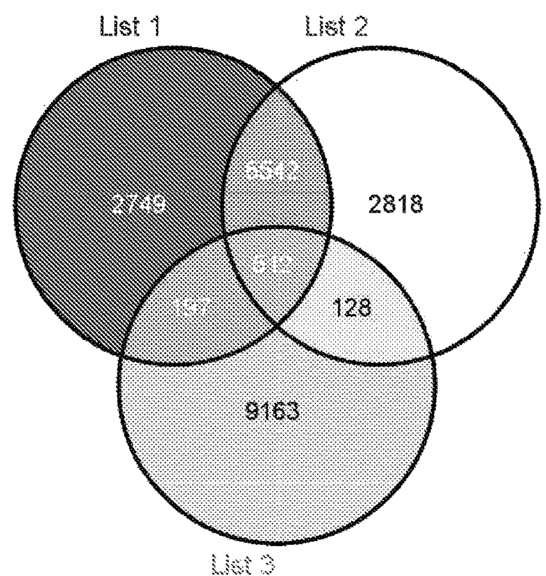

The intersection of the top 10,000 ranked probesets in the three lists revealed 512 common probesets (FIG. 4). Antisense probesets and those with less than 6 probes aligned to the probeset were removed to leave 393. Partek® Genomics Suite™ version 6.6, was used to generated fold change values.

Methylation

For the 22 patients, 11 metastatic biology subgroup and 11 non-metastatic biology subgroup, DNA was extracted using Recoverall (Life technologies). Genomic DNA (800 ng) was treated with sodium bisulfite using the Zymo EZ DNA Methylation Kit™ (Zymo Research, Orange, Calif., USA) according to the manufacturer's procedure, with the alternative incubation conditions recommended when using the Illumina Infinium Methylation Assay. The methylation assay was performed on 4 μl bisulfite-converted genomic DNA at 50 ng/μl according to the Infinium HD Methylation Assay protocol. Samples were processed onto Illumina 450 k arrays as per manufacturer's procedures. Uncorrected b-values were extracted with the same software. Probesets with changes in bivalues that were statistically significant were assessed using the Significance Analysis of Microarrays (SAM) (Tusher et al 2001). Using a False Discovery Rate (FDR) of 0.05, of the 235,526 probesets on the array 32,286 were hypo-methylated (corresponding to 7,222 unique genes) and 9,184 probesets (4,003 unique genes).

REFERENCES

Albertsen P C, Hanley J A, Barrows G H, Penson D F, Kowalczyk P D, Sanders M M et al (2005). Prostate cancer and the Will Rogers phenomenon. *J Natl Cancer Inst* 97: 1248-1253.

Altekruse S F, Huang L, Cucinelli J E, McNeel T S, Wells K M, Oliver M N (2010). Spatial patterns of localized-stage prostate cancer incidence among white and black men in the southeastern United States, 1999-2001. *Cancer Epidemiol Biomarkers Prev* 19: 1460-1467.

Babbio F, Pistore C, Curti L, Castiglioni I, Kunderfranco P, Brino L et al (2012). The SRA protein UHRF1 promotes epigenetic crosstalks and is involved in prostate cancer progression. *Oncogene.*

Bertucci F, Salas S, Eysteries S, Nasser V, Finetti P, Ginestier C, Charafe-Jauffret E, Loriod B, Bachelart L, Montfort J, Victorero G, Viret F, Ollendorff V, Fert V, Giovaninni M, Delpero J R, Nguyen C, Viens P, Monges G, Birnbaum D, Houlgatte R. Gene expression profiling of colon cancer by DNA microarrays and correlation with histoclinical parameters. Oncogene. 2004 Feb. 19; 23(7): 1377-91. PubMed PMID: 14973550.

Bostick M, Kim J K, Esteve P O, Clark A, Pradhan S, Jacobsen S E (2007). UHRF1 plays a role in maintaining DNA methylation in mammalian cells. *Science* 317: 1760-1764.

Chen X, Muller G A, Quaas M, Fischer M, Han N, Stutchbury B et al (2013). The forkhead transcription factor FOXM1 controls cell cycle-dependent gene expression through an atypical chromatin binding mechanism. *Mol Cell Biol* 33: 227-236.

Howlader A (2012). SEER Cancer Statistics Review, 1978-2009.

Kattan M W, Wheeler T M, Scardino P T (1999). Postoperative nomogram for disease recurrence after radical prostatectomy for prostate cancer. *J Clin Oncol* 17: 1499-1507.

Makarov D V, Sanderson H, Partin A W, Epstein J I (2002). Gleason score 7 prostate cancer on needle biopsy: is the prognostic difference in Gleason scores 4+3 and 3+4 independent of the number of involved cores? *J Urol* 167: 2440-2442.

Perou C M, Sorlie T, Eisen M B, van de Rijn M, Jeffrey S S, Rees C A et al (2000). Molecular portraits of human breast tumours. *Nature* 406: 747-752.

Pound C R, Partin A W, Eisenberger M A, Chan D W, Pearson J D, Walsh P C (1999). Natural history of progression after PSA elevation following radical prostatectomy. *JAMA* 281: 1591-1597.

Rasiah K K, Stricker P D, Haynes A M, Delprado W, Turner J J, Golovsky D et al (2003). Prognostic significance of Gleason pattern in patients with Gleason score 7 prostate carcinoma. *Cancer* 98: 2560-2565.

Sanders D A, Ross-Innes C S, Beraldi D, Carroll J S, Balasubramanian S (2013). Genome-wide mapping of FOXM1 binding reveals co-binding with estrogen receptor alpha in breast cancer cells. *Genome Biol* 14: R6.

Sharif J, Muto M, Takebayashi S, Suetake I, Iwamatsu A, Endo T A et al (2007). The SRA protein Np95 mediates epigenetic inheritance by recruiting Dnmt1 to methylated DNA. *Nature* 450: 908-912.

Smith E B, Frierson H F, Jr., Mills S E, Boyd J C, Theodorescu D (2002). Gleason scores of prostate biopsy and radical prostatectomy specimens over the past 10 years: is there evidence for systematic upgrading? *Cancer* 94: 2282-2287.

Sun Y, Goodison S. *Optimizing molecular signatures for predicting prostate cancer recurrence*, Prostate. 2009 Jul. 1; 69(10):1119-27. doi: 10.1002/pros.20961.

Tibshirani R, Walther G, Hastie T (2001). Estimating the number of clusters in a data set via the gap statistic. *Journal of the Royal Statistical Society: Series B (Statistical Methodology)* 63: 411-423.

Tusher V G, Tibshirani R, Chu G (2001). Significance analysis of microarrays applied to the ionizing radiation response. *Proc Natl Acad Sci USA* 98: 5116-5121.

Taylor B S, Schultz N, Hieronymus H, Gopalan A, Xiao Y, Carver B S, Arora V K, Kaushik P, Cerami E, Reva B, Antipin Y, Mitsiades N, Landers T, Dolgalev I, Major J E, Wilson M, Socci N D, Lash A E, Heguy A, Eastham J A, Scher H I, Reuter V E, Scardino P T, Sander C, Sawyers C L, Gerald W L. *Integrative genomic profiling of human prostate cancer*. Cancer Cell. 2010 Jul. 13; 18(1):11-22. doi: 10.1016/j.ccr.2010.05.026. Epub 2010 Jun. 24.

Unoki M, Kelly J D, Neal D E, Ponder B A, Nakamura Y, Hamamoto R (2009). UHRF1 is a novel molecular marker for diagnosis and the prognosis of bladder cancer. *Br J Cancer* 101: 98-105.

van't Veer L J, Dai H, van de Vijver M J, He Y D, Hart A A, Mao M et al (2002). Gene expression profiling predicts clinical outcome of breast cancer. *Nature* 415: 530-536.

Xu K, Wu Z J, Groner A C, He H H, Cai C, Lis R T, Wu X, Stack E C, Loda M, Liu T, Xu H, Cato L, Thornton J E, Gregory R I, Morrissey C, Vessella R L, Montironi R, Magi-Galluzzi C, Kantoff P W, Balk S P, Liu X S, Brown M. EZH2 oncogenic activity in castration-resistant prostate cancer cells is Polycomb-independent. Science. 2012 Dec. 14; 338(6113):1465-9. doi: 10.1126/science.1227604. PubMed PMID: 23239736; PubMed Central PMCID: PMC3625962.

SUPPLEMENTARY TABLE 1

| Characteristic | Numbers | % |
|---|---|---|
| Type | | |
| Primary Tumour | 70 | 100 |
| Primary Tumour with Mets | 21 | 100 |
| Metastatic Disease | 10 | 100 |
| Benign | 25 | 100 |
| Total | 126 | 100 |

SUPPLEMENTARY TABLE 1-continued

| Characteristic | Numbers | % |
|---|---|---|
| Gleason Score | | |
| <7 | 10 | 7.936507937 |
| 7 | 24 | 19.04761905 |
| >7 | 56 | 44.44444444 |
| NA | 36 | 28.57142857 |
| | 126 | 100 |

SUPPLEMENTARY TABLE 1-continued

| Characteristic | Numbers | % |
|---|---|---|
| Centre | | |
| Cambridge | 73 | 57.93650794 |
| Karolinska | 53 | 42.06349206 |
| Total | 126 | 100 |

Patient characteristics of internal sample set.

SUPPLEMENTARY TABLE 2

FOXM1 correlations

| Gene Symbol | r | p-value (correlation) | Lower CI | Upper CI | N | CHIP Overlap |
|---|---|---|---|---|---|---|
| CENPA | 0.772942 | 2.91E−26 | 0.691522 | 0.834968 | 126 | Yes |
| NUSAP1 | 0.77022 | 5.55E−26 | 0.687996 | 0.83292 | 126 | Yes |
| KIF11 | 0.762821 | 3.08E−25 | 0.678431 | 0.827343 | 126 | Yes |
| BUB1 | 0.760737 | 4.94E−25 | 0.675742 | 0.82577 | 126 | Yes |
| TOP2A | 0.754879 | 1.81E−24 | 0.668194 | 0.821342 | 126 | Yes |
| CDCA3 | 0.753481 | 2.46E−24 | 0.666396 | 0.820285 | 126 | Yes |
| KIF11 | 0.749425 | 5.90E−24 | 0.661184 | 0.817213 | 126 | Yes |
| ANLN | 0.74912 | 6.29E−24 | 0.660793 | 0.816982 | 126 | Yes |
| FAM111B | 0.746059 | 1.20E−23 | 0.656866 | 0.814661 | 126 | Yes |
| KIFC1 | 0.743611 | 2.00E−23 | 0.653728 | 0.812804 | 126 | Yes |
| ASPM | 0.741814 | 2.91E−23 | 0.651427 | 0.811439 | 126 | Yes |
| CENPA | 0.736676 | 8.26E−23 | 0.644857 | 0.807534 | 126 | Yes |
| RRM2 | 0.731796 | 2.18E−22 | 0.638628 | 0.803818 | 126 | Yes |
| CENPF | 0.729636 | 3.33E−22 | 0.635877 | 0.802173 | 126 | Yes |
| UBE2C | 0.725326 | 7.65E−22 | 0.630392 | 0.798885 | 126 | Yes |
| ASPM | 0.720223 | 2.01E−21 | 0.623909 | 0.794985 | 126 | Yes |
| ZWINT | 0.716062 | 4.34E−21 | 0.618633 | 0.791801 | 126 | Yes |
| NUSAP1 | 0.715926 | 4.45E−21 | 0.618461 | 0.791698 | 126 | Yes |
| EZH2 | 0.715254 | 5.03E−21 | 0.617611 | 0.791183 | 126 | Yes |
| PKMYT1 | 0.714612 | 5.65E−21 | 0.616797 | 0.790691 | 126 | Yes |
| KIFC1 | 0.713607 | 6.79E−21 | 0.615525 | 0.789922 | 126 | Yes |
| IQGAP3 | 0.713452 | 6.98E−21 | 0.615328 | 0.789802 | 126 | Yes |
| SPAG5///—///—/// ALDOC | 0.705774 | 2.75E−20 | 0.605626 | 0.783912 | 126 | Yes |
| PTTG1 | 0.700728 | 6.62E−20 | 0.599267 | 0.780034 | 126 | Yes |
| IQGAP3 | 0.700702 | 6.65E−20 | 0.599234 | 0.780014 | 126 | Yes |
| MLF1IP | 0.695649 | 1.57E−19 | 0.592879 | 0.776124 | 126 | Yes |
| CDCA8 | 0.695122 | 1.72E−19 | 0.592216 | 0.775718 | 126 | Yes |
| CDCA8 | 0.690806 | 3.53E−19 | 0.586798 | 0.772389 | 126 | Yes |
| AURKA | 0.690133 | 3.94E−19 | 0.585954 | 0.771869 | 126 | Yes |
| PTTG1 | 0.689026 | 4.73E−19 | 0.584567 | 0.771016 | 126 | Yes |
| HJURP | 0.688693 | 4.99E−19 | 0.584149 | 0.770758 | 126 | Yes |
| KIF14 | 0.686336 | 7.34E−19 | 0.581196 | 0.768937 | 126 | Yes |
| RRM2 | 0.685129 | 8.92E−19 | 0.579687 | 0.768005 | 126 | Yes |
| CDK1 | 0.676507 | 3.51E−18 | 0.568915 | 0.76133 | 126 | Yes |
| CENPF | 0.673672 | 5.44E−18 | 0.565382 | 0.759132 | 126 | Yes |
| UHRF1 | 0.673313 | 5.75E−18 | 0.564935 | 0.758854 | 126 | Yes |
| KIF20A | 0.666126 | 1.72E−17 | 0.555997 | 0.753271 | 126 | Yes |
| CDK1 | 0.663794 | 2.43E−17 | 0.553102 | 0.751457 | 126 | Yes |
| HIST1H2AJ | 0.632212 | 2.03E−15 | 0.514157 | 0.726757 | 126 | Yes |
| PLK1 | 0.624258 | 5.72E−15 | 0.504426 | 0.720498 | 126 | Yes |
| RNFT2 | 0.61696 | 1.44E−14 | 0.495524 | 0.714741 | 126 | Yes |
| CBX2 | 0.604289 | 6.80E−14 | 0.480127 | 0.704714 | 126 | Yes |
| UBE2T | 0.602802 | 8.12E−14 | 0.478324 | 0.703534 | 126 | Yes |
| SGOL1 | 0.592243 | 2.79E−13 | 0.46556 | 0.695144 | 126 | Yes |
| CDT1 | 0.573018 | 2.36E−12 | 0.442454 | 0.679795 | 126 | Yes |
| RHPN1 | 0.536586 | 9.40E−11 | 0.399136 | 0.650449 | 126 | Yes |
| AMH | 0.497271 | 3.16E−09 | 0.353071 | 0.618395 | 126 | Yes |
| ZNF251 | 0.487051 | 7.33E−09 | 0.341208 | 0.609995 | 126 | Yes |
| AR | 0.486909 | 7.42E−09 | 0.341044 | 0.609878 | 126 | Yes |
| ZNF467 | 0.484764 | 8.82E−09 | 0.33856 | 0.608112 | 126 | Yes |
| PRAME | 0.47932 | 1.36E−08 | 0.332266 | 0.603623 | 126 | Yes |
| MEX3A | 0.461466 | 5.38E−08 | 0.311716 | 0.588847 | 126 | Yes |
| ZNF467 | 0.449944 | 1.25E−07 | 0.298528 | 0.579266 | 126 | Yes |
| APLN | 0.448382 | 1.40E−07 | 0.296745 | 0.577964 | 126 | Yes |
| GPC2 | 0.445527 | 1.72E−07 | 0.293488 | 0.575584 | 126 | Yes |
| PRAME | 0.439591 | 2.61E−07 | 0.286727 | 0.570626 | 126 | Yes |
| SAC3D1 | 0.435599 | 3.44E−07 | 0.282189 | 0.567287 | 126 | Yes |
| RPL11 | 0.409932 | 1.87E−06 | 0.253175 | 0.545713 | 126 | Yes |
| HOXC6 | 0.408128 | 2.10E−06 | 0.251146 | 0.544191 | 126 | No |

SUPPLEMENTARY TABLE 2-continued

FOXM1 correlations

| Gene Symbol | r | p-value (correlation) | Lower CI | Upper CI | N | CHIP Overlap |
|---|---|---|---|---|---|---|
| IDUA | 0.407034 | 2.25E−06 | 0.249917 | 0.543267 | 126 | No |
| LINC00662 | 0.40266 | 2.95E−06 | 0.245006 | 0.539569 | 126 | No |
| APLN | 0.401304 | 3.21E−06 | 0.243485 | 0.538421 | 126 | No |
| DLX1 | 0.397375 | 4.08E−06 | 0.239082 | 0.535093 | 126 | No |
| APLN | 0.397311 | 4.10E−06 | 0.23901 | 0.535039 | 126 | No |
| KIFC2 | 0.386674 | 7.74E−06 | 0.227125 | 0.526009 | 126 | No |
| AR | 0.383667 | 9.22E−06 | 0.223774 | 0.52345 | 126 | Yes |
| AR | 0.375476 | 1.48E−05 | 0.214664 | 0.516468 | 126 | Yes |
| —///— | 0.373821 | 1.62E−05 | 0.212827 | 0.515055 | 126 | No |
| COMTD1 | 0.35892 | 3.67E−05 | 0.196336 | 0.502297 | 126 | Yes |
| PTPRT | 0.357122 | 4.04E−05 | 0.194352 | 0.500753 | 126 | No |
| ECE2 | 0.35557 | 4.39E−05 | 0.192641 | 0.49942 | 126 | No |
| CANX | 0.355306 | 4.45E−05 | 0.192349 | 0.499193 | 126 | Yes |
| MIA3 | 0.340939 | 9.36E−05 | 0.176557 | 0.486818 | 126 | No |
| CPNE4 | 0.338897 | 0.000103723 | 0.17432 | 0.485055 | 126 | No |
| ODAM | 0.328747 | 0.000170991 | 0.163223 | 0.476271 | 126 | Yes |
| AR | 0.321736 | 0.000239105 | 0.155581 | 0.470186 | 126 | Yes |
| CPNE4 | 0.313211 | 0.000355568 | 0.146317 | 0.462769 | 126 | No |
| RPS2///SNORA64///SNORA10 | 0.311142 | 0.000390829 | 0.144073 | 0.460966 | 126 | No |
| AR | 0.310899 | 0.000395174 | 0.14381 | 0.460754 | 126 | Yes |
| HOXC4 | 0.3105873 | 0.000401081 | 0.143456 | 0.460469 | 126 | No |
| PTPRT | 0.30997 | 0.000412213 | 0.142802 | 0.459943 | 126 | No |
| CPNE4 | 0.306883 | 0.0004738 | 0.139458 | 0.457249 | 126 | No |
| DSCAM-AS1 | 0.305957 | 0.000493863 | 0.138456 | 0.45644 | 126 | No |
| PPFIA2 | 0.300466 | 0.000629772 | 0.132521 | 0.451641 | 126 | No |
| IRAK1 | 0.299081 | 0.000669126 | 0.131025 | 0.450428 | 126 | No |
| — | 0.293355 | 0.000856865 | 0.124851 | 0.44541 | 126 | No |
| HOXC4 | 0.292152 | 0.000901978 | 0.123555 | 0.444355 | 126 | No |
| FOLH1///FOLH1B | 0.289076 | 0.00102741 | 0.120246 | 0.441655 | 126 | No |
| — | 0.282226 | 0.00136596 | 0.112888 | 0.435631 | 126 | No |
| NCAM2 | 0.279058 | 0.00155454 | 0.109492 | 0.432841 | 126 | No |
| — | 0.266099 | 0.00259802 | 0.0956408 | 0.421396 | 126 | No |
| — | 0.265466 | 0.00266239 | 0.0949655 | 0.420836 | 126 | No |
| MT-TG///MT-CO3///MT-TR///MT-ND4L///MT-ND3 | 0.262811 | 0.00294821 | 0.0921358 | 0.418484 | 126 | No |
| NTNG2 | 0.259671 | 0.00332155 | 0.0887944 | 0.415701 | 126 | No |
| SLC25A16 | 0.256563 | 0.00373266 | 0.0854892 | 0.412942 | 126 | No |
| — | 0.235972 | 0.0078127 | 0.063691 | 0.394596 | 126 | No |
| EIF3K | 0.22992 | 0.00959972 | 0.0573153 | 0.38918 | 126 | No |
| SSTR1 | 0.228927 | 0.00992512 | 0.0562702 | 0.388289 | 126 | No |
| CST1 | 0.221441 | 0.0127055 | 0.0484062 | 0.381572 | 126 | No |
| NIPAL1 | 0.211537 | 0.0174161 | 0.0380339 | 0.372658 | 126 | No |
| SSTR1 | 0.204885 | 0.0213703 | 0.031089 | 0.366655 | 126 | No |
| — | 0.184426 | 0.0387046 | 0.00983315 | 0.348107 | 126 | No |
| OXR1 | 0.181821 | 0.0415884 | 0.00713827 | 0.345736 | 126 | Yes |
| OPRK1 | 0.161588 | 0.0706621 | −0.0137096 | 0.327249 | 126 | No |
| MT-TA///MT-TY///MT-TC///MT-TN | 0.139903 | 0.118182 | −0.0358852 | 0.307293 | 126 | No |
| LRRN1 | 0.137159 | 0.125644 | −0.0386793 | 0.304758 | 126 | No |
| MT-TC///MT-TN///MT-TY///MT-TA | 0.129498 | 0.148398 | −0.0464647 | 0.297666 | 126 | No |
| LRRN1 | 0.125867 | 0.16021 | −0.0501469 | 0.294298 | 126 | No |
| MT-ND2///MTND2P28///MT-TW | 0.118797 | 0.185204 | −0.0573036 | 0.287729 | 126 | No |
| MT-TH///MT-TS2///MT-ND4///MT-ND5///MT-TL2 | 0.0828304 | 0.356482 | −0.0934333 | 0.25406 | 126 | No |
| MT-TQ | 0.0693974 | 0.440025 | −0.106809 | 0.241378 | 126 | No |
| WNT5A | 0.0551785 | 0.539432 | −0.120898 | 0.227889 | 126 | No |
| SNORA61///SNHG12///SNORA44 | 0.0508993 | 0.571383 | −0.125125 | 0.223817 | 126 | No |
| MT-TC///MT-TN///MT-TA///MT-TY | −0.0086152 | 0.923724 | −0.183249 | 0.166546 | 126 | No |

SUPPLEMENTARY TABLE 2-continued

| FOXM1 correlations | | | | | | |
|---|---|---|---|---|---|---|
| Gene Symbol | r | p-value (correlation) | Lower CI | Upper CI | N | CHIP Overlap |
| MT-CO1///MT-TW///MT-ND2 | 0.0101882 | 0.909852 | −0.184769 | 0.165016 | 126 | No |

Pearson correlation of over-expressed targets to FOXM1 levels across the entire internal dataset.

SUPPLEMENTARY TABLE 3

| Samples used for methylation analysis | | | | | | |
|---|---|---|---|---|---|---|
| mRNA Class label | Sample Type | Centre | Sample Age | Surgery Type | Gleason Score | Stage |
| Metastatic Biology | Primary Tumour | Karolinska | 1 | Radical | 6 | T2C |
| Metastatic Biology | Primary Tumour | Karolinska | 2 | Radical | 8 | T3A |
| Metastatic Biology | Metastatic Prostate Sample | Cambridge | 7 | Radical | 9 | NA |
| Metastatic Biology | Metastatic Prostate Sample | Cambridge | 4 | TURPS | 9 | NA |
| Metastatic Biology | Primary Tumour | Karolinska | 8 | Radical | 8 | TBC |
| Metastatic Biology | Primary Tumour | Karolinska | 1 | Radical | 8 | T3A |
| Metastatic Biology | Primary Tumour | Karolinska | 1 | TURPS | 9 | T3A |
| Metastatic Biology | Primary Tumour | Karolinska | 1 | Radical | 8 | T2A |
| Metastatic Biology | Primary Tumour | Karolinska | 6 | Radical | 7 | T3B |
| Metastatic Biology | Primary Tumour | Karolinska | 1 | Radical | 8 | T3A |
| Metastatic Biology | Primary Tumour | Karolinska | 1 | Radical | 9 | T2C |
| Non-Met. Biology | Primary Tumour | Karolinska | 2 | Radical | 7 | T3A |
| Non-Met. Biology | Primary Tumour | Karolinska | 2 | Radical | 6 | T3A |
| Non-Met. Biology | Primary Tumour | Karolinska | 2 | Radical | 8 | T3A |
| Non-Met. Biology | Primary Tumour | Cambridge | 2 | Radical | 7 | T3B |
| Non-Met. Biology | Primary Tumour | Cambridge | 1 | Radical | 9 | T3B |
| Non-Met. Biology | Primary Tumour | Cambridge | 1 | Radical | 7 | T3A |
| Non-Met. Biology | Primary Tumour | Karolinska | 5 | Radical | 8 | T2C |
| Non-Met. Biology | Primary Tumour | Karolinska | 2 | Radical | 9 | T3A |
| Non-Met. Biology | Primary Tumour | Karolinska | 1 | Radical | 9 | T3A |
| Non-Met. Biology | Primary Tumour | Karolinska | 7 | Radical | 8 | T2C |
| Non-Met. Biology | Primary Tumour | Karolinska | 1 | Radical | 8 | T3B |

Prostate IHC Development

Approach

Figure 7:
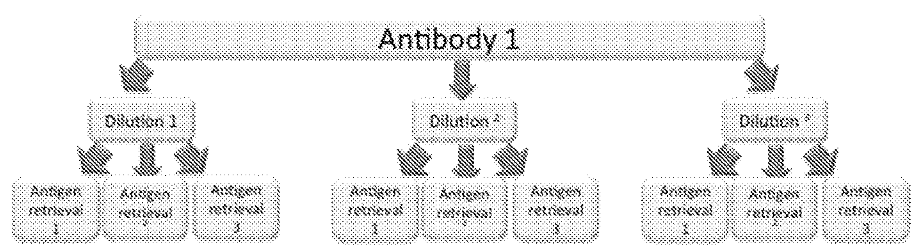

To identify suitable antibodies we performed analysis of 3 antibodies per target for selected targets against a 4 uM full face section from biomarker positive (confirmed by microarray profiling) prostate cancer samples. Each antibody was tested using 3 antigen retrieval methods using 3 dilutions (FIG. 7).

Each full face section contained an area of tumour, prostatic intraepithelial neoplasia (PIN), normal prostate epithelium, stroma and in some sections infiltrating immune cells.

This process allowed the identification of antibodies, antigen retrieval protocols and dilutions that detect the targets of interest.

Methods

Full face FFPE sections (4 μm) of prostate tumour were used.

Test Samples:

Prostate tumour (DI 20052): Age 58: Male. Pathology—Adenocarcinoma of the prostate gland. Tumour grade: 3+4=7.

Prostate tumour (DI 20054): Age 70: Male: Pathology—Adenocarcinoma of the prostate gland. Tumour grade: 3+4=7.

Protocol

All incubations were carried out at room temperature, unless otherwise stated.

1. Target Retrieval (FFPE):

Antigen retrieval 1—Dako PT Link and 3-in-1 pH6.1 Target Retrieval (TR) Solution.

97° C. 20 min with automatic heating and cooling.

Antigen retrieval 2—Dako PT Link and 3-in-1 pH9 Target Retrieval (TR) Solution.

97° C. 20 min with automatic heating and cooling.

Antigen retrieval 3—Microwave Vector citrate pH6.1 heat-induced epitope retrieval (HIER).

Slides were deparaffinized and rehydrated and then boiled (3×5 min) with the microwave set to full power.

All slides were rinsed with PBS—10 min

2. Assay Steps (DAKO Envision Flex Plus)

EnVision peroxidase block—5 min

Rinse

Dako CSAII serum-free protein block—10 min

Air-removal

Primary antibody—30 min

Rinse ×2

EnVision Flex/HRP—20 min

Rinse ×2

DAB—10 min

3. Counterstain and Coverslipping

Mayer's haematoxylin counterstain

Dehydrated in an ascending series of ethanols

Clear in xylene (×3)

Coverslip under DePeX.

Reagents—Primary Antibodies

CREM—anti-cAMP Responsive Element Modulator

1) Abcam Cat No: AB64832 Tested at 4, 2 and 1 μg/ml

2) Novus biomedical Cat No: NBP1-81760 Tested at 4, 2 and 1 μg/ml

3) Sigma Aldrich Cat No: HPA001818-100UL Tested at 0.8, 0.4 and 0.2 μg/ml (recommended concentration 0.16 μg/ml)

R-IgG-rabbit polyclonal IgG (Rabbit isotype control) Alere Cat No: X0936

ERRFI1—Anti-ERBB Receptor Feedback Inhibitor 1

1) Abcam Cat No: ab50272 Tested at 4, 2 and 1 μg/ml

2) Insight biotechnology Cat No: SC-137154 Tested at 4, 2 and 1 μg/ml (Santa Cruz Biotechnology, Inc.)

3) Sigma Aldrich Cat No: HPA027206-100UL Tested at 4, 2 and 1 μg/ml

M-IgG1—mouse monoclonal IgG1 (Mouse isotype control) Alere Cat No: X0931

R-IgG1—rabbit polyclonal IgG (Rabbit isotype control) Alere Cat No: X0936

HJURP Anti-Holliday Junction Recognition Protein

1) Abcam Cat No: AB100800 Tested at 4, 2 and 1 μg/ml Rabbit polyclonal

2) Abcam Cat No: AB175577 Tested at 4, 2 and 1 μg/ml Mouse monoclonal

3) Biorbyt Cat No: ORB140157 Tested at 4, 2 and 1 μg/ml Rabbit polyclonal

Rabbit isotype control Alere Cat No: X0936

Mouse IgG1 control Alere Cat No: X0931

PDK4—Anti-Pyruvate Dehydrogenase Kinase, Isozyme 4

1) Sigma Aldrich Cat No: HPA056731-100UL Tested at 4, 2 and 1 μg/ml

2) LifeSpan BioSciences Cat No: LS-B3459 Tested at 4, 2 and 1 μg/ml

3) Thermo scientific Cat No: PA5-13778 Tested at 4, 2 and 1 μg/ml

R-IgG—rabbit polyclonal IgG (Rabbit isotype control) Alere Cat No: X0936

SRSF5—Anti-Serine/Arginine-Rich Splicing Factor 5

1) Novus Biomedical Cat No: H00006430-B01 P Tested at 4, 2 and 1 μg/ml

2) Sigma Aldrich Cat No: HPA043484-100UL Tested at 4, 2 and 1 μg/ml

3) LifeSpan BioSciences Cat No: LS-B3091 Tested at 4, 2 and 1 μg/ml

R-IgG1—rabbit polyclonal IgG (Rabbit isotype control) Alere Cat No: X0936

Sigma Aldrich Cat No: F3520-1ML

Poly mouse IgG (M-IgG1, 2a, 2b)

M-IgG1—Alere Cat No: X0931

M-IgG2a—Alere Cat No: X0943

M-IgG2b—Alere Cat No: X0944

PDRG1—Anti-p53 and DNA Damage-Regulated Protein 1

1) Abcam Cat No: AB175965 Tested at 4, 2 and 1 μg/ml

2) Biorbyt Cat No: ORB162334 Tested at 4, 2 and 1 μg/ml

3) Novus Biomedical Cat No: NBP2-01854 Tested at 4, 2 and 1 μg/ml

M-IgG1—mouse monoclonal IgG1 (Mouse isotype control) Alere Cat No: X0931

R-IgG1—rabbit polyclonal IgG (Rabbit isotype control) Alere Cat No: X0936

Results

Following review of all the data the following targets have demonstrated IHC assays which are specific and sensitive and can be used for prostate cancer classification or prognosis.

| Target | Example Suitable Antibodies | Example Retrieval Conditions | Example Concentrations |
|---|---|---|---|
| CREM | Sigma Aldrich HPA001818 | pH9 PT Link | 0.8 μg/ml |
| | | pH6 Microwave | 0.8 μg/ml |
| | Novus Biomedical NBP1-81760 | pH6 PT link | 4 μg/ml |
| ERRFI1 | ABCAM AB50272 | pH9 PT Link | 4 μg/ml |
| | Sigma Aldrich HPA027206 | pH9 PT Link | 4 μg/ml |
| HJURP | Biorbyt ORB140157 | pH6 PT link | 4 μg/ml |
| PDK4 | Thermo Scientific PAS-13778 | pH6 PT link | 4 μg/ml |
| | | pH9 PT Link | 4 μg/ml |
| | Sigma Aldrich HPA056731 | pH9 PT Link | 4 μg/ml |
| SRSF5 | Sigma Aldrich HPA043484 | pH6 PT link | 4 μg/ml |
| PDRG1 | ABCAM AB175965 | pH9 PT Link | 4 μg/ml |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

Various publications are cited herein, the disclosures of which are incorporated by reference in their entireties.

The invention claimed is:

1. A method of treating prostate cancer in a subject in need thereof, comprising:

a) obtaining a prostate cancer sample of a tissue from a subject, wherein the tissue is already known to be a prostate cancer, wherein the prostate cancer sample comprises cancer cells and normal cells;

b) measuring the expression level of p53 and DNA Damage-Regulated Protein 1 (PDRG1) in the cancer cells from the prostate cancer sample and in the normal cells from the same prostate cancer sample;

c) comparing the expression levels of PDRG1 in the cancer cells to the normal cells;

d) detecting a significant increase in expression of PDRG1 in the cancer cells relative to the normal cells;

e) characterizing and/or prognosing the subject as having an increased likelihood of cancer recurrence and/or an increased likelihood of cancer metastasis; and f) administering a chemotherapeutic agent or radiotherapy to said subject of part (e), or carrying out prostate cancer removal surgery on said subject of part (e).

2. The method of claim 1 wherein the chemotherapeutic agent comprises, consists essentially of, or consists of:

a) an anti-hormone treatment;

b) a cytotoxic agent;

c) a biologic; and/or d) a targeted therapeutic agent.

3. The method of claim 1 wherein the expression level of PDRG1 is determined at the level of protein or RNA.

4. The method of claim 1 wherein the expression level of PDRG1 is determined by immunohistochemistry.

5. The method of claim 1 wherein the expression level of PDRG1 is determined by microarray, northern blotting, RNA seq (RNA sequencing), in situ RNA detection, or nucleic acid amplification.

6. The method of claim 2 wherein the anti-hormone treatment is bicalutamide and/or abiraterone.

7. The method of claim 2 wherein the biologic is an antibody and/or a vaccine.

8. The method of claim 2 wherein the biologic is sipuleucel-T.

9. The method of claim 2 wherein the radiotherapy is extended radiotherapy.

10. The method of claim 1 wherein the radiotherapy is extended-field radiotherapy.

* * * * *

SEQUENCE LISTING

```
<160> NUMBER OF SEQ ID NOS: 93

<210> SEQ ID NO 1
<211> LENGTH: 275
<212> TYPE: DNA
<213> ORGANISM: Homo sapiens

<400> SEQUENCE: 1

ctccaccttt ctccaatgac agaagccacc tttctccaat gacagaagtt acctttctcc      60

aatgacagaa gttccaggcc ccagagactc tatgtctgcc cagagactct atgtctgccc     120

gtccaagaga ctctatgtct gcccgtccat gactctatgt ctgcccgtcc atcagactgg     180

attagacaag agagatagca tggattagac aagagagata gcagcgatta gacaagagag     240

atagcagcat attagacaag agagatagca gcata                                275
```

<210> SEQ ID NO 2
<211> LENGTH: 275
<212> TYPE: DNA
<213> ORGANISM: Homo sapiens

<400> SEQUENCE: 2

```
ggcaatgtcc aaagtcaaat atcacgtcaa atatcaccta aactggttag actggttaga     60

ttacttctac agctaattgc aggcactggc gccctctggt cgccctctgg tggttatgaa    120

gacaaaatgg ctacttgacc tacagcaaaa ttgacctaca gcaaaagcca tttctaagcc    180

atttctgtac cataaaaatt atcatatgtt tcctacatct gacaggtttc ctacatctga    240

cagcacctaa atctgacagc acctaaaatg tttga                              275
```

<210> SEQ ID NO 3
<211> LENGTH: 275
<212> TYPE: DNA
<213> ORGANISM: Homo sapiens

<400> SEQUENCE: 3

```
gtctttgctt tgactactaa tctgttgact actaatctgt cttcaggact taatctgtct     60

tcaggactct ttctggggag gtaacagcac aatatctttg ctttgaacta tatacatcct    120

tgatgacatc cttgatgtat aatttgtcag gatgtataat ttgtcaggag cttgagtcag    180

gagcttgact tgattgtata attcatattt acacgagaac ctaataatat aactgccttg    240

tctttttcag ttgtcttttt caggtaatag cctgc                              275
```

<210> SEQ ID NO 4
<211> LENGTH: 275
<212> TYPE: DNA
<213> ORGANISM: Homo sapiens

<400> SEQUENCE: 4

```
acacattgat tgttatcttg actgagattg ttatcttgac tgacaaatat ccctttaccc     60

catttaattc tagagttacc ccatttaatt ctagagtcta tctagagtct agaacgcaag    120

gatctgagtc tagaacgcaa ggatctcttg caaggatctc ttggaatgac aaatggaatg    180

acaaatgata ggtacctaaa taggtaccta aaatgtaaca tgaaattata tttcccttta    240

ggctgtgata tttcccttta ggctgtgata gtttt                              275
```

<210> SEQ ID NO 5
<211> LENGTH: 275
<212> TYPE: DNA
<213> ORGANISM: Homo sapiens

<400> SEQUENCE: 5

```
atacaagtac tggttgaacc tgacccaagt actggttgaa cctgaccact gtactggttg     60

aacctgacca cttcaggttg aacctgacca cttcaaggtt gaacctgacc acttcaaggt    120

tgcagaacct gaccacttca aggttgcagt aatgatgctc acttgttgca gtacagatgc    180

tcacttgttg cagtacaatc atgctcactt gttgcagtac aatcatgcag tacaatcatc    240

gggttaaaaa gcagtacaat catcgggtta aaaaa                              275
```

<210> SEQ ID NO 6
<211> LENGTH: 275
<212> TYPE: DNA
<213> ORGANISM: Homo sapiens

<400> SEQUENCE: 6
ataatttacc gtaagtccta catttattta ccgtaagtcc tacatttagt agtcctacat 60
ttagtatcaa gctagtacat ttagtatcaa gctagagact aagctagaga ctgaatttga 120
actcatccaa aattcatgtg ctttttcctt aaaattcatg tgctttttcc ttctaggcct 180
ttcataccaa actaatagta atagtagttt atattctctt ccaacgtagt ttatattctc 240
ttccaacaaa tatattctct tccaacaaat gcata 275

<210> SEQ ID NO 7
<211> LENGTH: 275
<212> TYPE: DNA
<213> ORGANISM: Homo sapiens

<400> SEQUENCE: 7
agttttacta cttaccaggg tactgggtac tgtataaatc cttgtgctaa taaatccttg 60
tgctaaattt tgctagctat agagtatgtg gtccctgctg aatactgtat ctctatgtta 120
cataggttac atagaaagcc ctaggagact ctcctgttat ctgaacaact atttggaaca 180
actatttgct gtactgataa ggaaacagca tagtctcatt cacttaacac attttggtca 240
ttcgggaaca aacaaaatac cctctctact tttat 275

<210> SEQ ID NO 8
<211> LENGTH: 275
<212> TYPE: DNA
<213> ORGANISM: Homo sapiens

<400> SEQUENCE: 8
aactcaggag aatcttcttt acaattatta acattgatct gctgacaaaa acattgatct 60
gctgacaaaa cctggtgatc tgctgacaaa acctgggaat acctgggaat ttgggttgtg 120
tatgcttggg ttgtgtatgc gaatgtttca gtgtatgcga atgtttcagt gcctcgaatg 180
tttcagtgcc tcagacaaat gtttcagtgc ctcagacaaa tgtgtcagtg cctcagacaa 240
atgtgtattt tgcctcagac aaatgtgtat ttaac 275

<210> SEQ ID NO 9
<211> LENGTH: 275
<212> TYPE: DNA
<213> ORGANISM: Homo sapiens

<400> SEQUENCE: 9
acatttcaga catatccaaa gggaaaagaa gttgaactat gactggagta ggagtaaacc 60
atgtattccc ttatcgtaaa ccatgtattc ccttatcttt gtaatttgca ttactctggt 120
ggattgcatt actctggtgg attgttctag ctggtggatt gttctagtac tgtatgattg 180
ttctagtact gtattgggct tgttctagta ctgtattggg cttctgtatt gggcttcttc 240
gttaatagat gggcttcttc gttaatagat tattt 275

<210> SEQ ID NO 10
<211> LENGTH: 275
<212> TYPE: DNA
<213> ORGANISM: Homo sapiens

<400> SEQUENCE: 10
ctggtctatg cccttcagtg aacagatgcc cttcagtgaa cagttgtata aaccttgtct 60
tgtcaacctt gctgatcttg tcaaccttgc tgatccagct tcttattatt acaccttgtc 120
ttgctaacaa caatgtttct ataagtccaa gtttctataa gtccaacttc ctttacaact 180
tcctttatta atgtttccat aatgtttcca tttagcctca aaaatcctga tttacttttc 240
ccataagttt atttctgcct tgaagcctag aaatt 275

<210> SEQ ID NO 11
<211> LENGTH: 275
<212> TYPE: DNA
<213> ORGANISM: Homo sapiens

<400> SEQUENCE: 11
tatggttcat ttgcagtgac ttttagactt ttaaggcagt actgtttagc ggcagtactg 60
tttagcactt tgatagtttt gctaaattcg aataatgttt tatatactct gtatcaagtc 120
aaaataatat ctttggccat tttgctaaga ctttggccat tttgctaaga aacaaatgtc 180
aaactgatgt cacagtagtt gtcacagtag tttttgttag ctttatgtta gctttaaatc 240
atttttgctt aaaactatgc tgtttatatt gtcat 275

<210> SEQ ID NO 12
<211> LENGTH: 275
<212> TYPE: DNA
<213> ORGANISM: Homo sapiens

<400> SEQUENCE: 12
tattcatctt agttctgaaa acatggagtt aatcatgtta ctgaatctaa tttgcaatat 60
tagcctgcct gtatttatta gcctgcctgt atttttcatg tcatgtaaac cttttgtaca 120
ttgaaaagaa cgtttgtttt caggctcaga aacgtttgtt ttcaggctca gacctggctc 180
agaccttaag aactgatggt accttaagaa ctgatggtct tttcttacac aaaagtctaa 240
gcagttctga aacactacag tgacattggg tcatt 275

<210> SEQ ID NO 13
<211> LENGTH: 275
<212> TYPE: DNA
<213> ORGANISM: Homo sapiens

<400> SEQUENCE: 13
ggaattttgg gttattctct aaatgttttg ggttattctc taaatgacta gtgtgcttta 60
gaagtttaac tgtgattaac tgtgagaagg aaggcataat gaaggcataa ttcctggtcg 120
caggactggt cgcaggagga aacttaaaat attggtagta agattaatca tcctaaatca 180
tcctaaactt gggaatccac taaacttggg aatccaccac tgaaggggaa tccaccactg 240
aagcataaat ttgccttgta ataaacttgt gaaat 275

<210> SEQ ID NO 14
<211> LENGTH: 275
<212> TYPE: DNA
<213> ORGANISM: Homo sapiens

<400> SEQUENCE: 14
ttttgggtta ttctctaaat gactagtgtg ctttagaagt ttaactgtga gaaggcataa 60
ttcctggtcg caggactggt cgcaggagga aacttaaaat ttgttacatt gctgtgtctc 120
ctacatgtgt ctcctacagt ccctagaact tccctagaac tgtgacttgc ctttaaatca 180
tcctaaactt gggaatccac taaacttggg aatccaccac tgaaggggaa tccaccactg 240
aagcataaat ttgccttgta ataaacttgt gaaat 275

<210> SEQ ID NO 15

<211> LENGTH: 275
<212> TYPE: DNA
<213> ORGANISM: Homo sapiens

<400> SEQUENCE: 15

```
tacagagtgg atgaccacac tagcaggatg accacactag cacagaagag gtgattcctc     60

cccttggcgg gagaggcggg agagctctct cagtgtgaac gagctctctc agtgtgaaca    120

tgcctcggaa atcaggaagc caccagctgt atggagagtg ccttgctttt atttctcaga    180

cagcagagtt ttccaaagtt tttctgctcc tctaacagca ttgctcagca ttgctcttta    240

gtgtgtgtta ttagtgtgtg ttaacctgtg gtttg                               275
```

<210> SEQ ID NO 16
<211> LENGTH: 275
<212> TYPE: DNA
<213> ORGANISM: Homo sapiens

<400> SEQUENCE: 16

```
tctaccattt actaattatg tgactcaaat atttgacccc tctgagactt atatttgacc     60

cctctgagac ttggattgac ccctctgaga cttggatttc cccctctgag acttggattt    120

cacatcctct gagacttgga tttcacatct ttaagtgtaa aaagcttggt tcacaagtgt    180

aaaaagcttg gttcacagta aaatatgtac ttcctttaag gaaatgatac agtagattat    240

taagcacctt acagtagatt attaagcacc ttgct                               275
```

<210> SEQ ID NO 17
<211> LENGTH: 275
<212> TYPE: DNA
<213> ORGANISM: Homo sapiens

<400> SEQUENCE: 17

```
tctaccattt actaattatg tgactgtcaa atatttgacc cctctgagac atatttgacc     60

cctctgagac ttggacccct ctgagacttg gatttcacat agtgtaaaaa gcttggttca    120

cagtaaaagc ttggttcaca gtaggtggca ataaatatgt acttccttta aggaaatatt    180

cataaggaga caacacacaa gatacagtag attattaagc accttacagt agattattaa    240

gcaccttgct taagcacctt gctttgatta aaaag                               275
```

<210> SEQ ID NO 18
<211> LENGTH: 275
<212> TYPE: DNA
<213> ORGANISM: Homo sapiens

<400> SEQUENCE: 18

```
aagtcaggta atatacctgg tttacagtca ggtaatatac ctggtttact aataatttgt     60

acaatggttt attccataat ttgtacaatg gtttattccc gtttattccc aagtatgcct    120

taagcttatt cccaagtatg ccttaagcag tcccaagtat gccttaagca gaacacccaa    180

gtatgcctta agcagaacaa tgtattttgc atactcaagg tgagagtatt ttgcatactc    240

aaggtgagaa attttgcata ctcaaggtga gaatt                               275
```

<210> SEQ ID NO 19
<211> LENGTH: 275
<212> TYPE: DNA
<213> ORGANISM: Homo sapiens

<400> SEQUENCE: 19

```
gaagcactga tcacctgtta gcattaagca ctgatcacct gttagcattg gcactgatca     60
```

```
cctgttagca ttgccactga tcacctgtta gcattgccat tgatcacctg ttagcattgc    120

cattcatata aagcttttttg gtaatatgtt attaaaatga caagcactat atcactgagg    180

agaaaacaat tccttagaag gaggagaaaa caattcctta gaagttccca tgtgtaggta    240

ttgaaaaagt ccatgtgtag gtattgaaaa agttt                              275


<210> SEQ ID NO 20
<211> LENGTH: 275
<212> TYPE: DNA
<213> ORGANISM: Homo sapiens

<400> SEQUENCE: 20

ataaacctgt accttagtga atattaaacc tgtaccttag tgaatatttt tttagattag     60

ggtaatacag acactgatta gggtaataca gacactgaag ctgaagatta tttgagaact    120

gtactagatt atttgagaac tgtacttggc actgtacttg gcataaactc atttcgtact    180

tggcataaac tcatttcatt ggcataaact catttcattg ttatatattt taacctatgg    240

aaaattctgt aaattctgtg ttctcctaat attat                              275


<210> SEQ ID NO 21
<211> LENGTH: 275
<212> TYPE: DNA
<213> ORGANISM: Homo sapiens

<400> SEQUENCE: 21

ataaacctgt accttagtga atattaaacc tgtaccttag tgaatatttt gattagggta     60

atacagacac tgaagagatt atttgagaac tgtacttggc ttgagaactg tacttggcat    120

aaactgtact tggcataaac tcatttcatt ggcataaact catttcattg ttataacttc    180

tattccagat gcctttgagt aacctatgga aaattctgtg ttctcaaatt ctgtgttctc    240

ctaatattat ctgtgttctc ctaatattat tgctt                              275


<210> SEQ ID NO 22
<211> LENGTH: 275
<212> TYPE: DNA
<213> ORGANISM: Homo sapiens

<400> SEQUENCE: 22

tttttacact gtcgatgttt ccaattttac actgtcgatg tttccaatgc tacactgtcg     60

atgtttccaa tgcatttcca atgcatcttc catgatgcat tatttaaatt agacattacc    120

agtaaaaatt agacattacc agtaatttca aaatttctaa attcataggg tagaacatag    180

ggtagaatca cctgtaaaag agggtagaat cacctgtaaa agcttacctg taaaagcttg    240

tttgatttct ctgtaaaagc ttgtttgatt tctta                              275


<210> SEQ ID NO 23
<211> LENGTH: 275
<212> TYPE: DNA
<213> ORGANISM: Homo sapiens

<400> SEQUENCE: 23

taaggtcaat gccagagacg gaagcaggtc aatgccagag acggaagcct tcaatgccag     60

agacggaagc cttttcaatg ccagagacgg aagccttttt aatgccagag acggaagcct    120

ttttcaaata acttatatca tcagcatacc atcatcagca tacctttatt gtgatcatca    180

gcataccttt attgtgatct cagcatacct ttattgtgat ctatcgcata cctttattgt    240
```

gatctatcaa catacctttta ttgtgatcta tcaat 275

<210> SEQ ID NO 24
<211> LENGTH: 275
<212> TYPE: DNA
<213> ORGANISM: Homo sapiens

<400> SEQUENCE: 24
cttccctcat ctcctattat atattgaaat tccctcttaa gctcattgtg aattccctct 60
taagctcatt gtgtttcatt gtgttttcac ccagttcact attgtgtttt cacccagttc 120
actagaccca gttcactaga ccaacagcaa ttcactagac caacagcaat accaggcaat 180
accagtacca gagttatgtt ttagaaagtc tactagctgt ccacaagtct actagctgtc 240
cacaaagtcg gctgtccaca aagtcgtagt tcatt 275

<210> SEQ ID NO 25
<211> LENGTH: 275
<212> TYPE: DNA
<213> ORGANISM: Homo sapiens

<400> SEQUENCE: 25
gaggtgggag gtaacagcac aatatgggag gtaacagcac aatatctttg ctttgaacta 60
tatacatcct tgatgacatc cttgatgtat aatttgtcag gatgtataat ttgtcaggag 120
cttgagtcag gagcttgact tgattgtata attcatattt acacgagaac ctaattttac 180
acgagaacct aatataactg cctaatataa ctgccttgtc tttttaatat aactgccttg 240
tctttttcag ttgtcttttt caggtaatag cctgc 275

<210> SEQ ID NO 26
<211> LENGTH: 275
<212> TYPE: DNA
<213> ORGANISM: Homo sapiens

<400> SEQUENCE: 26
aacttcatat tggccaacac cagggacttc atattggcca acaccagggt cttcatattg 60
gccaacacca gggttttcat attggccaac accagggttg tcatattggc caacaccagg 120
gttgtatatt ggccaacacc agggttgtat tattggccaa caccagggtt gtattttggc 180
caacaccagg gttgtattct tggccaacac cagggttgta ttctaggcca acaccagggt 240
tgtattctat gccaacacca gggttgtatt ctatg 275

<210> SEQ ID NO 27
<211> LENGTH: 275
<212> TYPE: DNA
<213> ORGANISM: Homo sapiens

<400> SEQUENCE: 27
gcagactcct cttgcaaggc gtaccagact cctcttgcaa ggcgtacctc ctcttgcaag 60
gcgtacctcc aaacattgca aggcgtacct ccaaacataa aaggcgtacc tccaaacata 120
attgaggcgt acctccaaac ataattgatt cactcaagca atcctgagga atactactca 180
agcaatcctg aggaatactg tcaagcaatc ctgaggaata ctgaggagga atactgaggg 240
agggcctggc ggaatactga gggagggcct ggcta 275

<210> SEQ ID NO 28
<211> LENGTH: 275
<212> TYPE: DNA
<213> ORGANISM: Homo sapiens

<400> SEQUENCE: 28

```
ttcagaaata taagagcggc agccaagagc ggcagccaga ccaaccagtt agcggcagcc     60
agaccaacca gtttttcttg atgtgaacct gaccctactc tgaacctgac cctactcctt    120
tagaactgac cctactcctt tagaagacag taaatagctt taacccaaac tgttccaaga    180
gacattaaca cagttctgta gggaaatgtg gcatactgta tccttgagat atcctgcagt    240
aaagacacaa gcagtaaaga cacaagatac cttgt                               275
```

<210> SEQ ID NO 29
<211> LENGTH: 275
<212> TYPE: DNA
<213> ORGANISM: Homo sapiens

<400> SEQUENCE: 29

```
cttggcaacc atattgtcac ctgtaaccat attgtcacct gtacctgtca cctgtacctg     60
tcacacatct tgaaagtacc tgtcacacat cttgaaaaat gactaatttt cccttacagt    120
tcctgtttcc cttacagttc ctgcttggtc tgcttggtcc cacccactga agtagaagta    180
gctcatcgta gtgcgggccg gctcatcgta gtgcgggccg tattagggta cgttagactc    240
agatggaaaa attagctatg tgattgagag ttatt                               275
```

<210> SEQ ID NO 30
<211> LENGTH: 275
<212> TYPE: DNA
<213> ORGANISM: Homo sapiens

<400> SEQUENCE: 30

```
gtatcctggt gaatgtctgt tcagctatcc tggtgaatgt ctgttcagct acatgtactt     60
tataagtatt ggtttcatgt actttataag tattggtttg tactttataa gtattggttt    120
gggtgacttt ataagtattg gtttgggtgt tttataagta ttggtttggg tgttcttata    180
agtattggtt tgggtgttcc tataagtatt ggtttgggtg ttcctataag tattggtttg    240
ggtgttcctt taagtattgg tttgggtgtt ccttc                               275
```

<210> SEQ ID NO 31
<211> LENGTH: 275
<212> TYPE: DNA
<213> ORGANISM: Homo sapiens

<400> SEQUENCE: 31

```
cggatgatgc aatataggag agaatggatg atgcaatata ggagagaata gatgatgcaa     60
tataggagag aataagatgc aatataggag agaataaagc agcaggtctt cgagctagat    120
tgacagcagg tcttcgagct agattgacag caggtcttcg agctagattg acagaaggtc    180
ttcgagctag attgacagaa gaggggagga gcctgaagtg tatttagggg aggagcctga    240
agtgtatttt caccagctgg taaagttttc aaata                               275
```

<210> SEQ ID NO 32
<211> LENGTH: 275
<212> TYPE: DNA
<213> ORGANISM: Homo sapiens

<400> SEQUENCE: 32

```
attcagaatt agtttaatgc cttaattcag aattagttta atgccttaat ttagggtcaa     60
gggtgtcctc cactctaggg tcaagggtgt cctccactct gggtcaaggg tgtcctccac    120
```

```
tcttttcaag ggtgtcctcc actctttaac agctgctgga cagacacatt agagcgctgc    180

tggacagaca cattagagca cacattagag cagctgtttg ttattattag agcagctgtt    240

tgttattgat ttagagcagc tgtttgttat tgata                               275


<210> SEQ ID NO 33
<211> LENGTH: 275
<212> TYPE: DNA
<213> ORGANISM: Homo sapiens

<400> SEQUENCE: 33

tgctgaatac gctgaagtaa atcctaatac gctgaagtaa atccttgttc gctgaagtaa     60

atccttgttc actgatgaag taaatccttg ttcactgaag tgaagtcttt caattgagct    120

ggttggaagt ctttcaattg agctggttga ttgaaaaatg ctcagttcta actaaaacta    180

atgaaatgga tttcccagta taatgaaatg gatttcccag taggggcata tcacctgtat    240

agtagttata tcacctgtat agtagttata tgcat                               275


<210> SEQ ID NO 34
<211> LENGTH: 275
<212> TYPE: DNA
<213> ORGANISM: Homo sapiens

<400> SEQUENCE: 34

aaagaagtcc gggagatgaa tggctggatg tcagtgcacg gttagtgttt agtgcacggt     60

tagtgtttga gcagacagag ggcagacttg taaagtacct aagtacctgt agtgaaaaga    120

atgtgggacc cgattagcag aaaggtgttt gtgtttgcac atactttata caaaagaaat    180

gaacgtggac ttttacacat gaacgtggac ttttacacat gtgcatattt ttctggaggc    240

tatatggatt aaatcatttt caatcagcgt ttggt                               275


<210> SEQ ID NO 35
<211> LENGTH: 275
<212> TYPE: DNA
<213> ORGANISM: Homo sapiens

<400> SEQUENCE: 35

catattaagt agtaacagaa gtctgaacag aagtctgaac aattggataa gtctgaacaa     60

ttggataaat ttgacgataa atttgacttc caagacagct atttgacttc caagacagct    120

aaactaaact acactacact gttatagtta tacactacac tgttatagtt aatctgttat    180

agttaatctg acaaaaatgt gttaatctga caaaaatgtc ctcaataaag catctgttta    240

attcaacctt aaagcatctg tttaattcaa ccttt                               275


<210> SEQ ID NO 36
<211> LENGTH: 275
<212> TYPE: DNA
<213> ORGANISM: Homo sapiens

<400> SEQUENCE: 36

tttttgctat gttagtctgc ataactaaaa ttttcctgca tagctacaat attttcctgc     60

atagctacaa tcctgctgca tagctacaat cctgtggtgt gctacaatcc tgtggtgtgt    120

caccagtgtc accataaagg tggaccctgt aaggtggacc ctgtgtgaat gagaagtgga    180

ccctgtgtga atgagaaaat acatggccag tcttttacaa gttgagtctt ttacaagttg    240

agtaggcata acaaagtttt gtggccactt atttt                               275
```

<210> SEQ ID NO 37
<211> LENGTH: 275
<212> TYPE: DNA
<213> ORGANISM: Homo sapiens

<400> SEQUENCE: 37
aaataaaacc agtttgcagg tgcacataaa accagtttgc aggtgcacaa gcaggtgcac 60
aaactatgag ggtcttgcac aaactatgag ggtcttgtat tcttgtatcc acgtaacaca 120
ggtagttgta tccacgtaac acaggtagtt gtactgtgta aagatgcata gtcatcatag 180
tcatctcatt tggttggctt tctcatttgg ttggctttgt accttccttt tttagccttg 240
gcttttgttg tagccttggc ttttgttgaa ctaga 275

<210> SEQ ID NO 38
<211> LENGTH: 275
<212> TYPE: DNA
<213> ORGANISM: Homo sapiens

<400> SEQUENCE: 38
aatatctaaa tatgtctcac atattattac ctaattctgt ggcaaaaatg aattctgtgg 60
caaaaatggt gcctcctgtg gcaaaaatgg tgcctctgat tgtggcaaaa atggtgcctc 120
tgatggatgt tgtgatatag tattgtcagt gttgtgatat agtattgtca gtgtggtgat 180
atagtattgt cagtgtgtac tagtattgtc agtgtgtaca tatatcttat gaaccataac 240
aaatgtagct atgaaccata acaaatgtag ctttt 275

<210> SEQ ID NO 39
<211> LENGTH: 275
<212> TYPE: DNA
<213> ORGANISM: Homo sapiens

<400> SEQUENCE: 39
taatcctcaa atatactgta ccattggaga agttttattc attacctaat attacctaat 60
tctgtggcaa aaatgctgtg gcaaaaatgg tgcctctgat aaatggtgcc tctgatgttg 120
tgatagcctc tgatgttgtg atatagtatt gtgatatagt attgtcagtg tgtacaaaac 180
ctgtgtaaac ctctgtcctt gtaaacctct gtccttatga accatatgaa ccataacaaa 240
tgtagctttt gctttttaaa gtccattgta ttgtt 275

<210> SEQ ID NO 40
<211> LENGTH: 275
<212> TYPE: DNA
<213> ORGANISM: Homo sapiens

<400> SEQUENCE: 40
actcttcact aggattccct atatacttca ctaggattcc ctatatatat tctagatatt 60
tactatagtg cagaagatat ttactatagt gcagaagcaa tatttactat agtgcagaag 120
caacagatta tgttttatct agcaaatttg tatgttttat ctagcaaatt tgtaagtgct 180
ttctatggtt attaaaagac tgctttctat ggttattaaa agactgctat actcttcact 240
aggattccct ctatactctt cactaggatt cccta 275

<210> SEQ ID NO 41
<211> LENGTH: 275
<212> TYPE: DNA
<213> ORGANISM: Homo sapiens

<400> SEQUENCE: 41

```
cttcactagg attccctata tatatatatg cctgttatag atatctagat gatatttact     60

atagtgcaga agcaagatta tgttttatct agcaaatttg tttcatttaa ctttccaggc    120

ttttaaatta cttttagtgc tttctatggt gtgctttcta tggttattaa aagacccatt    180

ttataagatt tctctccata gatttctctc catatatatt tctattataa ctgctatact    240

cttcactagg ctatactctt cactaggatt cccta                               275


<210> SEQ ID NO 42
<211> LENGTH: 275
<212> TYPE: DNA
<213> ORGANISM: Homo sapiens

<400> SEQUENCE: 42

ctcctgaaac gtaggtgaga acaaagaaac gtaggtgaga acaaagtgat acgtaggtga     60

gaacaaagtg atggatgatg gagtgagaca ttgtggcctg agtgagacat tgtggcctgg    120

aagtcgtgag acattgtggc ctggaagtct acaactgcat actaatcttt taaagactgc    180

atactaatct tttaaagcct ctgcatacta atcttttaaa gccttttaaa gcctttaaca    240

gttgctttta taaagccttt aacagttgct tttaa                               275


<210> SEQ ID NO 43
<211> LENGTH: 275
<212> TYPE: DNA
<213> ORGANISM: Homo sapiens

<400> SEQUENCE: 43

gaaatgttag tatctcaatt acaccgttag tatctcaatt acaccaactg agtatctcaa     60

ttacaccaac tgtgcatctc aattacacca actgtgcaaa tagtagatgg atactgaata    120

ctcagatgga tactgaatac tcaggcccac atactcaggc ccacttaaat tattatactc    180

aggcccactt aaattattaa gtttttgtct ttatgctatg tacaggtctt tatgctatgt    240

acagagaaat gctatgtaca gagaaatgtg ataat                               275


<210> SEQ ID NO 44
<211> LENGTH: 275
<212> TYPE: DNA
<213> ORGANISM: Homo sapiens

<400> SEQUENCE: 44

ataatttgaa ggttggcaga ccagtaattt gaaggttggc agaccagttg ttgaaggttg     60

gcagaccagt tgcgcaaggt tggcagacca gttgcgctga ttggcagacc agttgcgctg    120

attacggcag accagttgcg ctgattactc agaccagttg cgctgattac tcttaccagt    180

tgcgctgatt actcttagag gttgcgctga ttactcttag agaaggcgct gattactctt    240

agagaagaag cgctgattac tcttagagaa gaaga                               275


<210> SEQ ID NO 45
<211> LENGTH: 275
<212> TYPE: DNA
<213> ORGANISM: Homo sapiens

<400> SEQUENCE: 45

aatatggtta gttccagagt gcaaatttaa aattccatac acgtttgcag catttggata     60

ctttgaaaga tgacattgtt aatgaatgac tagcccaatt gaatgactag cccaattatc    120

cttattgact agcccaatta tccttataaa gctttgatat catactactc tgcctttgat    180

atcatactac tctgcctttg atatcatact actctgcctt tgtgggtggg cacatatgta    240
```

gacactacta gggcacatat gtagacacta ctaaa 275

<210> SEQ ID NO 46
<211> LENGTH: 200
<212> TYPE: DNA
<213> ORGANISM: Homo sapiens

<400> SEQUENCE: 46
tgactgggaa ttgttactgt tgtacgactg ggaattgtta ctgttgtact actgggaatt 60
gttactgttg tacttctggg aattgttact gttgtactta tgggaattgt tactgttgta 120
cttatgggaa ttgttactgt tgtacttatt ggaattgtta ctgttgtact tattcgtaca 180
atttggtgtt tgtattagct 200

<210> SEQ ID NO 47
<211> LENGTH: 275
<212> TYPE: DNA
<213> ORGANISM: Homo sapiens

<400> SEQUENCE: 47
tgcactttaa ctgacttaag tggcacttta actgacttaa gtggcattaa taactgactt 60
aagtggcatt aaacataagt ggcattaaac atttgagagc acatttgaga gctaactata 120
ttttttataa gactactata caaactacag taagactact atacaaacta cagaggacta 180
ctatacaaac tacagagttt aactacagag tttatgattt aaggtcagag tttatgattt 240
aaggtactta tactttaaat aaaggtgact gggaa 275

<210> SEQ ID NO 48
<211> LENGTH: 275
<212> TYPE: DNA
<213> ORGANISM: Homo sapiens

<400> SEQUENCE: 48
aaataatgca tccagcagta caataataat gcatccagca gtacaataaa atgcatccag 60
cagtacaata aaagttgcat ccagcagtac aataaaagta atttaatgac atgcctatat 120
gagaatttaa tgacatgcct atatgagaag atgaatatat ggcatttgca gattttgaat 180
atatggcatt tgcagatttt gcagattttt atattagttg ctttgcagat ttttatatta 240
gttgctttgt agatttttat attagttgct ttgtt 275

<210> SEQ ID NO 49
<211> LENGTH: 275
<212> TYPE: DNA
<213> ORGANISM: Homo sapiens

<400> SEQUENCE: 49
atgcaatatt tgtaaggctt gttccatatt tgtaaggctt gttccaatgc aaggcttgtt 60
ccaatgccac atacttgttc caatgccaca tacttgcagc aatgccacat acttgcagct 120
cccattgcag ctcccattct atgtgtcatc agctcccatt ctatgtgtca tcaattatgt 180
gtcatcaata gtgtcctatg gtgtcatcaa tagtgtccta tgcaacatca atagtgtcct 240
atgcaataaa attatttgca ggtctttaaa tcatt 275

<210> SEQ ID NO 50
<211> LENGTH: 275
<212> TYPE: DNA
<213> ORGANISM: Homo sapiens

<400> SEQUENCE: 50
gcttggatgt aaaacgtaat agaaaaaaag ggagagctag gaaatggact gaacttgaca 60
gctagcagaa ttggtgcaga attggtttcc attagacatt ggtttccatt agacattact 120
cccagttcca ttagacatta ctcccaggag tactcccagg agctatatta catagtccca 180
ggagctatat tacatagtaa aataggaact ttgaattacc ctctggaact ttgaattacc 240
ctctgtgcta aattaccctc tgtgctactt ttatt 275

<210> SEQ ID NO 51
<211> LENGTH: 275
<212> TYPE: DNA
<213> ORGANISM: Homo sapiens

<400> SEQUENCE: 51
tagtctttgg tgcttggatg taaaaaaaag ggagagctag gaaatggact gaacttgaca 60
gctagcagaa ttggtgcaga attggtttcc attagacatt ggtttccatt agacattact 120
cccagtactc ccaggagcta tattacatag ttatacatcc tacatgaccc attcaacaaa 180
gctgttttac tactaactta aataggaact ttgaattacc ctctggaact ttgaattacc 240
ctctgtgcta aattaccctc tgtgctactt ttatt 275

<210> SEQ ID NO 52
<211> LENGTH: 275
<212> TYPE: DNA
<213> ORGANISM: Homo sapiens

<400> SEQUENCE: 52
gctccaactg ttggacaaaa taaagggatt gtgccagacc ttgtgttttt tgtgccagac 60
cttgtgtttt ttgatgtgtt ttttgattcg aactttgcca ttttgattcg aactttgcca 120
aggccttgcc aaggcctgga acgctgaaga gcctggaacg ctgaagaata atacttcttt 180
ccaaaaagca ttaagaggtt tgtttgtctg tttcctttat cctctctgtt tcctttatcc 240
tcttggtaaa aagatttaat gtttgggtga tacaa 275

<210> SEQ ID NO 53
<211> LENGTH: 275
<212> TYPE: DNA
<213> ORGANISM: Homo sapiens

<400> SEQUENCE: 53
agtgtttatc agcagactgt aaaggagact gtaaaggcaa gtaggctctg tttgtaaatt 60
ccctccaacc tgtacgtaaa ttccctccaa cctgtacaac ccctccctca aatttgagta 120
gccaactcaa atttgagtag ccaagtatct ttgagtagcc aagtatctag ctttgatcta 180
gctttgtgta attagacagc gctttgtgta attagacagc ttcaaaatta gacagcttca 240
agtatgtatt ttgagttgga aatgatgctt agatt 275

<210> SEQ ID NO 54
<211> LENGTH: 275
<212> TYPE: DNA
<213> ORGANISM: Homo sapiens

<400> SEQUENCE: 54
gttcctggac cccacaagac ttgattagct tatgtgacaa ccctcatctt atccccatcc 60
cttctgaaag taggagttgg agctcttgca atggaattca gaacagactc tggagtgtcc 120
atttatctgg agtgtccatt tagactacac tagactacac taactagact tttaagtgtg 180
gtttggtgca agtcagaata aaattctggc tagttgaatc cacaattcat ttatatacag 240
gcttcccttt aataaacacg tttatgccta tcagc 275

<210> SEQ ID NO 55
<211> LENGTH: 275
<212> TYPE: DNA
<213> ORGANISM: Homo sapiens

<400> SEQUENCE: 55
caggcttcct agaggtgtgc tatacaggtg tgctatacca tgcgtctgtc ataccatgcg 60
tctgtcgttg tgcttacagt tctttggtaa gcattgtcgt ggtaagcatt gtcgtatctg 120
gtgatcattg tcgtatctgg tgatggatta tgatggatta acatatagcc tttgttctaa 180
taaaatagtc gccttcgttt taaaatagtc gccttcgttt tctgtatctt tctcttacaa 240
tctgttttag gacatctttg cttatgaaac ctgta 275

<210> SEQ ID NO 56
<211> LENGTH: 275
<212> TYPE: DNA
<213> ORGANISM: Homo sapiens

<400> SEQUENCE: 56
agaggagaga acacgtctta caggaagaga acacgtctta caggatggaa aagtgtgtag 60
ctaggttatt tcggagtagc taggttattt cggagtgtta ggttatttcg gagtgttatt 120
tatctgtttt tgattcttga gactgtgagg cttggttgac ttctctgccc ttaaagttga 180
cttctctgcc cttaaagtaa tagtgaaatt ggttccatca gagatgttcc atcagagata 240
acctcgagtt catcagagat aacctcgagt tcttg 275

<210> SEQ ID NO 57
<211> LENGTH: 275
<212> TYPE: DNA
<213> ORGANISM: Homo sapiens

<400> SEQUENCE: 57
attagatggt gatttgacgt ctgggttaat ttactgtagg actagtggca taggactagt 60
ggcagtgagt ctcatgtggc agtgagtctc atattgctgt agtgagtctc atattgctgt 120
catatagtag cctaaagacc acgctttgag cacgctttga gaaactcgta aaggtgaaac 180
tcgtaaaggt ttgtcataga taattttaag ctttagttgc ctactaagta ggatgcagta 240
caagtttgtc gatgcagtac aagtttgtcc tttac 275

<210> SEQ ID NO 58
<211> LENGTH: 275
<212> TYPE: DNA
<213> ORGANISM: Homo sapiens

<400> SEQUENCE: 58
aaaaaaccct gtgccttaca caatgaaacc ctgtgcctta cacaatgtgt ccctgtgcct 60
tacacaatgt gtatacacaa tgtgtatatt gagttgatac aaaaggtgat tgagacacag 120
cctctaaagg tgattgagac acagcctctg ctctgtcctg agcttagtct agtagctgag 180
cttagtctag taggaggtga cttagtctag taggaggtga cagatctagt aggaggtgac 240
agatttgtaa aataatagat ttgaagttgc tgagc 275

<210> SEQ ID NO 59

<211> LENGTH: 275
<212> TYPE: DNA
<213> ORGANISM: Homo sapiens

<400> SEQUENCE: 59
aaaaaaccct gtgccttaca caatgaaacc ctgtgcctta cacaatgtgt ggtattatac 60
aatcattcat tcagcagcaa acattcactt actgagcacc actgagcacc tactaatgtt 120
ccaggcctac taatgttcca ggtactgatt aaaggtgatt gagacacagc ctctgacaca 180
gcctctgtcc tgagcttagt ctctgtcctg agcttagtct agtagctagt aggaggtgac 240
agatttgtaa aataatagat ttgaagttgc tgagc 275

<210> SEQ ID NO 60
<211> LENGTH: 275
<212> TYPE: DNA
<213> ORGANISM: Homo sapiens

<400> SEQUENCE: 60
atactgactt gtttgcattg ggcatgcata tatactactc ttgcgagcag tactactctt 60
gcgagcagga ggcctcgagc aggaggcctg aaatctccta agcctggcaa caagggaaat 120
cccgaaaatc ccgagattgt aggcaagagg gatgctttca aaaagcctgg agggaagtgg 180
agatgattat gtttaacgca atgtttaacg cattccttct ttggtgagct gctagcatag 240
tatggattaa aatagccaga ctatactgac ttgtt 275

<210> SEQ ID NO 61
<211> LENGTH: 275
<212> TYPE: DNA
<213> ORGANISM: Homo sapiens

<400> SEQUENCE: 61
gggaataccg agtgctcaat tttattttta tagtttctca tagtttcttc tctcatagtt 60
tcttcatggc cacagtagtt tcttcatggc cacagataaa cacagataaa cccctgaaac 120
caatcataac cctgtagttc tcactattgg ccctgtagtt ctcactattg ggtcacacta 180
ttgggtcatt aacacagtca acagtcatta aatgcaagca ggtctatgca agcaggtcta 240
gtattgacta gtctagtatt gactagccct tctgg 275

<210> SEQ ID NO 62
<211> LENGTH: 275
<212> TYPE: DNA
<213> ORGANISM: Homo sapiens

<400> SEQUENCE: 62
gaggagttct gagattgact actaagacta ctaatgtctg ccatggaagt ggagcagtta 60
tggtacgagt gtcatgagtg tcatattttt gccagttctg atttttgcca gttctgactg 120
aaggcaaagc ccaggatctt tctagcctct gatctttcta gcctctaccc agtgtcagtg 180
tcactgactt tctagctcat tagctcattg ccctagtgaa attggtacaa tgccaaatcc 240
tatcaaaggg atcaaagggt attggctgcc tgtag 275

<210> SEQ ID NO 63
<211> LENGTH: 275
<212> TYPE: DNA
<213> ORGANISM: Homo sapiens

<400> SEQUENCE: 63
atcgggctgt ggtgaccgca acaagtcggg ctgtggtgac cgcaacaagc gggagcacac 60

```
cgtttcctga ttgctagcac accgtttcct gattgctcag ccctccttgg tgattccgca    120

gtgagtcctt ggtgattccg cagtgagaga aaggcaagat tgtgtcccat tccccgcaag    180

attgtgtccc attcccccag agctccgcgc caggatggcg aggaaaggat ggcgaggaac    240

tcaataaagt tggcgaggaa ctcaataaag tgctt                               275


<210> SEQ ID NO 64
<211> LENGTH: 275
<212> TYPE: DNA
<213> ORGANISM: Homo sapiens

<400> SEQUENCE: 64

acttttgcca agcaccatac ttaaggccaa gcaccatact taagactcaa tacttaagac     60

tcaacttttt tgcaatatca gacaaagcac tgtctttaag cactagatcc cttcttctga    120

aaatcgatcc cttcttctga aaatcactgt atattttttt agcattcact gcatgagtta    180

agtctgcttt cctatccctt taagtctgct ttcctatccc ttatactgct ttcctatccc    240

ttatacagaa atcccttata cagaagctat ccatt                               275


<210> SEQ ID NO 65
<211> LENGTH: 275
<212> TYPE: DNA
<213> ORGANISM: Homo sapiens

<400> SEQUENCE: 65

cttgtcctcc aagttatggg ggatctcttg tactgacaat ctgtgttttc gtactgacaa     60

tctgtgtttt ccaggctgtg ttttccagga gttacgtcaa gttttccagg agttacgtca    120

aactaaggag ttacgtcaaa ctacctgtac gttacgtcaa actacctgta ctggtgtcaa    180

actacctgta ctggtttaaa atacatattt tgtgctaatc ttgttagtgt ttgtctagca    240

tgtttgttta gtctagcatg tttgtttaat ccttt                               275


<210> SEQ ID NO 66
<211> LENGTH: 275
<212> TYPE: DNA
<213> ORGANISM: Homo sapiens

<400> SEQUENCE: 66

ttcctccaaa acaaacgaca gcaacaaacg acagcaacga aaactcctta gacagcaacg     60

aaaactcctt aatcagaaaa ctccttaatc agaacactga tcagaacact gatccaatga    120

ggaatcagga gaacttagtg caagactaca gagaacttag tgcaagacta caggaagact    180

acaggagtta acagatggcc tacaggagtt aacagatggc cagctgagtt tatatcaaat    240

cctgaagaaa atatcaaatc ctgaagaaat aagcc                               275


<210> SEQ ID NO 67
<211> LENGTH: 275
<212> TYPE: DNA
<213> ORGANISM: Homo sapiens

<400> SEQUENCE: 67

ggcacaagaa attggagctg gagaagctgg agaagattga tgaaagtgca gtgcaggtgt     60

gtaaggaaat agaacaaata gaacagtctg ctgggagtca atctccaggg tgacggaacc    120

cagtggtgac ggaacccagt gtattacctg gtgtattacc tgctggaacc aaggagtagg    180

ttactagtga ataccccaat gttactagtg aataccccaa tggttgaata ccccaatggt    240
```

ttctccaatt ccaatggttt ctccaattat gccca 275

<210> SEQ ID NO 68
<211> LENGTH: 275
<212> TYPE: DNA
<213> ORGANISM: Homo sapiens

<400> SEQUENCE: 68
atggtgaaac aagggatgtc tgattaacaa gggatgtctg attggaagta gatatttatt 60
taggttctag gacatctagg acattagtat cagtgaggac tcagtgagga cagtaatttc 120
ctgctgtaat ttcctgcttg tttgtatttc gtatttcagt gatcacatac acttcgtgat 180
cacatacact tctttacctg acacttcttt acctgataac gtctctacct gataacgtct 240
ctcttctcta ctacttaaag gtatcccttg aattc 275

<210> SEQ ID NO 69
<211> LENGTH: 275
<212> TYPE: DNA
<213> ORGANISM: Homo sapiens

<400> SEQUENCE: 69
tttgcaaacc ctggttgctg tatttaaacc ctggttgctg tatttgttca ctggttgctg 60
tatttgttca gtgacagatt atttgcacga actggactgt gaactggact gtgtgcaacg 120 cttttttgg gagaatgatg tccccgttgt aatgatgtcc ccgttgtatg tatgatcccc 180
gttgtatgta tgagtggctt ccactgtata gaaggttttt gtagcgtagc ctgaatgtct 240
tactgtgatc cctgaatgtc ttactgtgat caatt 275

<210> SEQ ID NO 70
<211> LENGTH: 275
<212> TYPE: DNA
<213> ORGANISM: Homo sapiens

<400> SEQUENCE: 70
tgcaggagac attggtattc tgggcgcagg agacattggt attctgggca tgcactttaa 60
ctgacttaag tggcacttta actgacttaa gtggcattaa taactgactt aagtggcatt 120
aaacataagt ggcattaaac atttgagagc acatttgaga gctaactata ttttttaaga 180
ctactataca aactacagag gactactata caaactacag agtttaacta cagagtttat 240
gatttaaggt cagagtttat gatttaaggt actta 275

<210> SEQ ID NO 71
<211> LENGTH: 275
<212> TYPE: DNA
<213> ORGANISM: Homo sapiens

<400> SEQUENCE: 71
aagaatttgg cacagttact cacttgaatt tggcacagtt actcactttg tgctgaatac 60
gctgaagtaa atcctaatac gctgaagtaa atccttgttc gctgaagtaa atccttgttc 120
actgatgaag tctttcaatt gagctggttg gaagtctttc aattgagctg gttgattgaa 180
aaatgctcag ttctaactaa taatgaaatg gatttcccag taggggcata tcacctgtat 240
agtagttata tcacctgtat agtagttata tgcat 275

<210> SEQ ID NO 72
<211> LENGTH: 275
<212> TYPE: DNA
<213> ORGANISM: Homo sapiens

<400> SEQUENCE: 72

```
tccaaaagca agtagccaaa gccgtaagca agtagccaaa gccgttgcca caagtagcca     60

aagccgttgc caaactagcc aaagccgttg ccaaacccca atgggccctt tatttatgac    120

gacttggccc tttatttatg acgactttat atttatgacg actttattta ttctatatat    180

atattgggtc gtctgcttcc atatatattg ggtcgtctgc ttccctattg ggtcgtctgc    240

ttcccttgta ttttgtaata ttgaaaacga cgata                               275
```

<210> SEQ ID NO 73
<211> LENGTH: 275
<212> TYPE: DNA
<213> ORGANISM: Homo sapiens

<400> SEQUENCE: 73

```
atacaggtgc aactcaatcc ccgttgtgca actcaatccc cgttaataaa tgtaggtata     60

ggcattctac cctttgtata ggcattctac cctttgaaat taccctttga aatagctgtg    120

tcccactttg aaatagctgt gtcccaacct agaaatatcc aagttgtcct tgaatgttgt    180

ccttgaattg tctaaccatg gtctaaccat ggacataaac agttgatgga cataaacagt    240

tgtctccctt tactgtgtag aatactttga cttaa                               275
```

<210> SEQ ID NO 74
<211> LENGTH: 275
<212> TYPE: DNA
<213> ORGANISM: Homo sapiens

<400> SEQUENCE: 74

```
aagagagaac aactactgtg atcagagaac aactactgtg atcaggctat actactgtga     60

tcaggctatg tatggatgta tggaatacag tgttattttc aattagctgt gtgaaatacc    120

agtgttagct gtgtgaaata ccagtgtggt atttatttaa gcttatgtca gaccttattt    180

aagcttatgt cagacctatt aagcttatgt cagacctatt tgacacagac ctatttgaca    240

taacactata gacataacac tataaaggtt gacaa                               275
```

<210> SEQ ID NO 75
<211> LENGTH: 275
<212> TYPE: DNA
<213> ORGANISM: Homo sapiens

<400> SEQUENCE: 75

```
acatgtactt tataagtatt ggtttcatgt actttataag tattggtttg atgtacttta     60

taagtattgg tttggtgtac tttataagta ttggtttggg tactttataa gtattggttt    120

gggtgacttt ataagtattg gtttgggtgt tttataagta ttggtttggg tgttcttata    180

agtattggtt tgggtgttcc tataagtatt ggtttgggtg ttcctataag tattggtttg    240

ggtgttcctt taagtattgg tttgggtgtt ccttc                               275
```

<210> SEQ ID NO 76
<211> LENGTH: 225
<212> TYPE: DNA
<213> ORGANISM: Homo sapiens

<400> SEQUENCE: 76

```
acagccaaaa ctccacagtc aatatcagcc aaaactccac agtcaatatt agccaaaact     60

ccacagtcaa tattagccaa aactccacag tcaatattag ccaaaactcc acagtcaata    120
```

```
ttagtgatgt ttttatgtgc tctccaaatt atgtttttat gtgctctcca aattttgttt    180

ttatgtgctc tccaaatttt ttactgtttc tgattgtatg gaaat                    225


<210> SEQ ID NO 77
<211> LENGTH: 275
<212> TYPE: DNA
<213> ORGANISM: Homo sapiens

<400> SEQUENCE: 77

tctgtctttt ataaagattc caccttaaag attccacctc cagtcctctc aaagattcca     60

cctccagtcc tctctcctac tcaggccctt gaggctatta tactcaggcc cttgaggcta    120

ttaggtcagg cccttgaggc tattaggaga ggcccttgag gctattagga gatgcccctt    180

gaggctatta ggagatgctt agaactcaac aaaatcccaa tccaagaact caacaaaatc    240

ccaatccaag caacaaaatc ccaatccaag tcaaa                               275


<210> SEQ ID NO 78
<211> LENGTH: 275
<212> TYPE: DNA
<213> ORGANISM: Homo sapiens

<400> SEQUENCE: 78

gaaatcctat gcctagaaac caattacatg actgctattt agggaaggcc gggaaggcct     60

aatctttgta acttacaaag tgattgacag agtgggctct gcctctgtca cttctagttg    120

tggaattcta gttgtggaat ccttggcaag tggcaagtgt cttaaactct ttatgactct    180

ttatgccatt gagttattat attattccca tctgttatta aagaggatta aagtatatgc    240

ctcagaggga gcctcagagg gatgtttgag tgtaa                               275


<210> SEQ ID NO 79
<211> LENGTH: 275
<212> TYPE: DNA
<213> ORGANISM: Homo sapiens

<400> SEQUENCE: 79

atctacatta aagccacaag tcaccaagcc acaagtcacc ctttgctgaa ccacaagtca     60

ccctttgctg aagtcaagtc agtattagta gttggaagca agcagtgtgt tattcttgac    120

cccatgtggc acttattaag tagcttgctt aagtagcttg cttttccata attatttcca    180

taattatggc ctagcttttt agctttttaa aacctactat gaacaacacc acaagcatag    240

agttttccaa aggaaaccaa ttatactgaa tcagg                               275


<210> SEQ ID NO 80
<211> LENGTH: 275
<212> TYPE: DNA
<213> ORGANISM: Homo sapiens

<400> SEQUENCE: 80

ttttaataca acaagatcaa ctagattaat acaacaagat caactagaag gatcaactag     60

aagaattcaa ctgtccaact agaagaattc aactgtctca actagaagaa ttcaactgtc    120

tcaagtcaag gtaccccaat atatctcgca aaggtacccc aatatatctc gcaatggtac    180

cccaatatat ctcgcaattc taccccaata tatctcgcaa ttccacccaa tatatctcgc    240

aattccaaac aatatatctc gcaattccaa acttt                               275


<210> SEQ ID NO 81
<211> LENGTH: 275
```

<212> TYPE: DNA
<213> ORGANISM: Homo sapiens

<400> SEQUENCE: 81
aaaaaacttt ttggtgctcc agtgtaaaac tttttggtgc tccagtgtag actttttggt 60
gctccagtgt agggcaaata aactatcagc ttggatggtc aataaactat cagcttggat 120
ggtcagcttg gatggtcact tgaatagaag tggatggtca cttgaataga agatgtgaat 180
agaagatggt tatacacagt tttgctcttg tatggcaaaa taattgctct tgtatggcaa 240
aataattagt gtatggcaaa ataattagtg agttt 275

<210> SEQ ID NO 82
<211> LENGTH: 275
<212> TYPE: DNA
<213> ORGANISM: Homo sapiens

<400> SEQUENCE: 82
cattcacttt tgttaacagt atttctcact tttgttaaca gtatttctct tatagtggat 60
gatatacaca gtggcagtgg atgatataca cagtggcaaa acacagtggc aaaacaaaag 120
tacataaaaa tgtcactata tcttcccatt gtcactatat cttcccattt aacatatatc 180
ttcccattta acattgtttt tgtatattgg gtgtagattt ctgacattgg gtgtagattt 240
ctgacatcaa tgggtgtaga tttctgacat caaaa 275

<210> SEQ ID NO 83
<211> LENGTH: 275
<212> TYPE: DNA
<213> ORGANISM: Homo sapiens

<400> SEQUENCE: 83
gaaggtgctc actaacagag gtacaggtgc tcactaacag aggtacatta ctaacagagg 60
tacattactg caatgtaaca gaggtacatt actgcaatgt taacagttaa acaagctgtt 120
tacagcagtt aaacaagctg tttacagttt gagctattta aagcttatta tattttgcat 180
tatgtgtaca gtattggaca gcattatgtg tacagtattg gacaagtgta cagtattgga 240
caaaggattt tacagtattg gacaaaggat tttat 275

<210> SEQ ID NO 84
<211> LENGTH: 275
<212> TYPE: DNA
<213> ORGANISM: Homo sapiens

<400> SEQUENCE: 84
gctgtcctcc gtattacgtg accggctccg tattacgtga ccggcaaata tacgtgaccg 60
gcaaataaat ctcatgtaga atgcaaaatg ttggcacgtc gaatgcaaaa tgttggcacg 120
tcaaagttgg cacgtcaaaa atatgaatgt tgaatgtgta gacaactgta gttgtgacaa 180
ctgtagttgt gctcagtttg gggaagtgta ttttactctg atcaaggaag tgtattttac 240
tctgatcaaa taatgctgga atactcaaga attgc 275

<210> SEQ ID NO 85
<211> LENGTH: 275
<212> TYPE: DNA
<213> ORGANISM: Homo sapiens

<400> SEQUENCE: 85
gatatggacg ttatcattgg tctggatgga cgttatcatt ggtctggtga tggtctggtg 60

```
agatgtttca tatttattat gagttaatgc tgcctgtgtc agttaatgct gcctgtgtct    120

atggggtcta tggggttctg tcttctttga tgtcttcttt gatagccatc tattcgatag    180

ccatctattc atctggatca ctattcatct ggatcatggg acccttggtt tggagttgag    240

atatcagtct gttgagatat cagtctcgga aactt                               275


<210> SEQ ID NO 86
<211> LENGTH: 275
<212> TYPE: DNA
<213> ORGANISM: Homo sapiens

<400> SEQUENCE: 86

tcacaggggc ctcaagaatt ggtatacagg ggcctcaaga attggtatgt ctcaagaatt     60

ggtatgtatg atgtgtgatg tgatctggtc cagccagggc atgtgatctg gtccagccag    120

ggccttgatc tggtccagcc agggcctggc cagctctcta ggtttgatat gacttgctct    180

ctaggtttga tatgacttta ctctctaggt ttgatatgac tttagtttgt caatatagat    240

ggtaggaagc gtcaatatag atggtaggaa gcaga                               275


<210> SEQ ID NO 87
<211> LENGTH: 275
<212> TYPE: DNA
<213> ORGANISM: Homo sapiens

<400> SEQUENCE: 87

gatggatgca actgaagcag agtgtggtgc ccagatgtgc gctattagat gtgcgctatt     60

agatgtttct ctgattttct ctgataatgt ccccaatcat gataatgtcc ccaatcatac    120

caggggtccc caatcatacc agggagactg cagggagact ggcattgacg agaacttgac    180

gagaactcag gtggaggctt tcagctttgc aaagagccac cctagcagct gaccgcatgg    240

gtgtgagcca ctactcaata aaagcgaagg tggac                               275


<210> SEQ ID NO 88
<211> LENGTH: 275
<212> TYPE: DNA
<213> ORGANISM: Homo sapiens

<400> SEQUENCE: 88

aagatgtcat ttgcaataga gcagtgtcat ttgcaataga gcagtccatt gaattttcac     60

tggacctgtg atgtcaattt tcactggacc tgtgatgtca ctttttgtgc acagattatg    120

atgaattatc actctgcctg tgtatagtca cactctgcct gtgtatagtc agatagtata    180

gtcagatagt ccatgcgaag cagatagtcc atgcgaaggc tgtattccat gcgaaggctg    240

tatatattga ttataaagtg tgtaagttac cagtt                               275


<210> SEQ ID NO 89
<211> LENGTH: 225
<212> TYPE: DNA
<213> ORGANISM: Homo sapiens

<400> SEQUENCE: 89

aaaagactga gcatgctcac tttttaaacc ctttgtattg tagataagag aaagactgag     60

catgctcact tttttaaccc tttgtattgt agataagagg aagactgagc atgctcactt    120

ttttaacaaa ccctttgtat tgtagataag agacaaaccc tttgtattgt agatacaaac    180

cctttgtatt gtagataaga gacaaaccct ttgtattgta gataa                    225
```

<210> SEQ ID NO 90
<211> LENGTH: 275
<212> TYPE: DNA
<213> ORGANISM: Homo sapiens

<400> SEQUENCE: 90
acttaccacc actaaactgc gagagagcag actgccggta acgcgcggcc ccgctgcagt 60
ttcttgggac ataggctaaa ctgcgagaga agctaaacgt gagcgcaaag aagctacagc 120
ctggaggaca gcagactgcc ggtaacgcgc ggacttacca ccactaaact gcgagggaga 180
gactcagcaa cgacccatac ggcgggagag actcagcaac gacccgtttc ttgggacata 240
ggagcgcaaa tgcccgctgc agtttcttgg gacat 275

<210> SEQ ID NO 91
<211> LENGTH: 275
<212> TYPE: DNA
<213> ORGANISM: Homo sapiens

<400> SEQUENCE: 91
aaagtttaga tctgtccctt aataaaaatc ttaatcatta tccttctaag aggatacaaa 60
tttagtgctc ttaacatcaa aatcttaatc attatccttc atcagaaagt ttagatctgt 120
cccttatcat tatccttcta agaggataca ctaagaggat acaaatttag tgctccttaa 180
tcattatcct tctaagagga gaaagtttag atctgtccct taatatacaa atttagtgct 240
cttaacttgt ttgcttaaac taatgaacaa atatg 275

<210> SEQ ID NO 92
<211> LENGTH: 275
<212> TYPE: DNA
<213> ORGANISM: Homo sapiens

<400> SEQUENCE: 92
aaatcttaat cattatcctt ctaagaggat acaaatttag tgctcttaac atcagaaagt 60
ttagatctgt cccttccaag agttaagata tccctaatgt cctgaaagca gtaaccaaga 120
gttaacttaa tcattatcct tctaagagga gaaagtttag atctgtccct taatagttaa 180
gatatcccta atgttttgct taaccaagag ttaagatatc cctaataaga tatccctaat 240
gttttgctta tacaaattta gtgctcttaa cttgt 275

<210> SEQ ID NO 93
<211> LENGTH: 275
<212> TYPE: DNA
<213> ORGANISM: Homo sapiens

<400> SEQUENCE: 93
actctttact caggagggcc ttgcaagagt aggtgctgcc tagcagccct agcagccctt 60
cgtggccact ctttaaggtg ctgcctagca gcccttcgtg atgacacgtg tcaagatgcc 120
cttccatgtg ttcattaagg gctcaataaa ccagtatgaa ctgccgtgaa gtcaagaggt 180
cccagtatga actgccgtga tctttactca ggagggcctt gcagattacc atatgacacg 240
tgtcaagatg ttatgtgttc attaagggct caata 275